US006387890B1

(12) United States Patent
Christianson et al.

(10) Patent No.: US 6,387,890 B1
(45) Date of Patent: May 14, 2002

(54) COMPOSITIONS AND METHODS FOR INHIBITING ARGINASE ACTIVITY

(75) Inventors: David Christianson, Media, PA (US); Ricky Baggio, Waltham; Daniel Elbaum, Newton, both of MA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/545,737

(22) Filed: Apr. 10, 2000

Related U.S. Application Data

(63) Continuation-in-part of application No. PCT/US98/21430, filed on Oct. 9, 1998.
(60) Provisional application No. 60/061,607, filed on Oct. 10, 1997.

(51) Int. Cl.[7] ............................. A61K 31/69; C07F 5/02
(52) U.S. Cl. ............................................. 514/64; 562/7
(58) Field of Search ................................. 562/7; 514/64

(56) References Cited

U.S. PATENT DOCUMENTS

| | | | |
|---|---|---|---|
| 4,160,452 A | | 7/1979 | Theeuwes |
| 4,256,108 A | | 3/1981 | Theeuwes |
| 4,265,874 A | | 5/1981 | Bonsen et al. |
| 4,477,391 A | * | 10/1984 | Collins |
| 4,851,422 A | | 7/1989 | Natsugari et al. |
| 4,876,251 A | | 10/1989 | Morimmoto et al. |

OTHER PUBLICATIONS

CA:127:201930 ab of J A Chem Soc 119(34) pp. 8107–8108 by Baggio et al, Aug. 1997.*
Journal of Medicinal Chemistry by Matteson et al vol. 7 p. 640–643, 1964.*
CA:125:222375 abs of Tetrahedron Lett by Denniel et al 37(29) pp. 5111–5114, 1996.*
CA:87:6321 abs of Diss Abstr Int B 37(8) pp. 3927–8 by Hartz.*
Albina et al., 1995, J. Immunol. 155:4391–4396.
Bacon et al., 1988, J. Mol. Graph. 6:219–200.
Baker et al., 1980, Fed. Proc., Fed. Am. Soc. Exp. Biol. 39:1686.
Baker et al., 1983, Biochemistry 22:2098–2103.
Bergeron et al., 1987, J. Org. Chem. 52:1700–1703.
Biancani et al., 1985, Gastroenterology 89:867–874.
Boden, 1975, Synthesis 784.
Boucher et al., 1994, Biochem. Biophys. Res. Commun. 203:1614–1621.
Brünger et al., 1987, Science 235:458–460.
Brünger et al., 1998, Acta Crystallogr. D54:905–921.
Campos et al., 1995, J. Biol. Chem. 270:1721–1728.
Cavaili et al., 1994, Biochemistry 33:10652–10657.
Chakder and Rattan, 1997, J. Pharmacol. Exp. Ther. 282:378–384.
Chakder and Rattan, 1993, Am. J. Physiol. Gastrointest. Liver Physiol. 264:G7–G12.
Chemais et al., 1993, Biochem. Biophys. Res. Commun. 196:1558–1565.
Christianson, 1997, Prog. Biophys. Molec. Biol. 67:217–252.
Christianson et al., 1989, J. Am. Chem. Soc. 111:6412–6419.
Christianson et al., 1996, Acc. Chem. Res. 29:331–339.

(List continued on next page.)

*Primary Examiner*—Jean F. Vollano
(74) *Attorney, Agent, or Firm*—Akin, Gump, Strauss, Hauer & Feld, L.L.P.

(57) ABSTRACT

Compositions and methods for inhibiting arginase activity, including arginase activity in a mammal, are provided. Methods of making the compositions of the invention are also provided as are methods of using the compositions therapeutically. The compositions described herein are useful for alleviating or inhibiting a variety of arinase- and NO synthase-related disorders, including heart diseae, gastrointestinal motility disorders, and penile erectile dysfunction in humans.

26 Claims, 34 Drawing Sheets

OTHER PUBLICATIONS

Corraliza et al., 1995, Biochem. Biophys. Res. Commun. 206:667–673.
Curley et al., 1997, J. Am. Chem. Soc. 119:1529–1538.
Daghigh et al., 1994, Biochem. Biophys. Res. Commun. 202:174–180.
Denniel et al., 1996, Tetrahedron Letters 37:5111–5114.
Esnouf, 1997, J. Mol. Graphics 15:132–134.
Feldman et al., 1993, J. Med. Chem. 36:491–496.
Fisher et al., 1995, Methods Enzymol. 259:194–221.
Furchgott, 1995, Annu. Rev. Pharmacol. Toxicol., 35:1–27.
Gotoh et al., 1996, FEBS Lett. 395:119–122.
Griffith and Stuehr, 1995, Annu. Rev. Physiol. 57:707–736.
Gross et al., 1990, Biochem. Biophys. Res. Commun. 170:96–103.
Herzfeld et al., 1976, Biochem. J. 153:469–478.
Hibbs et al., 1987, J. Immunol. 138:550–565.
Ikemoto et al., 1993, Clin. Chem. 39:794–799.
Jabri et al., 1995, Science 268:998–1004.
Jenkinson et al., 1996, Comp. Biochem. Physiol. 114B:107–132.
Jones et al., 1991, Acta. Crystallogr. A47:110–119.
Kanyo et al., 1992, J. Mol. Biol. 224:1175–1177.
Kanyo et al., 1996, Nature 383:554–557.
Keller et al., 1991, Cell. Immunol. 134:249–256.
Kettner et al., 1984, J. Biol. Chem. 259: 15106–15114.
Khangulov et al., 1995, Biochemistry 34:2015–2025.
Khangulov et al., 1998, Biochemistry 37:8539–8550.
Kim et al., 1991, J. Clin. Invest. 88:112–118.
Klatt et al., 1993, J. Biol. Chem. 268:14781–14787.
Knight et al., 1989, J. Chem. Soc., Dalton Trans.275–281.
Kraulis et al., 1991, J. Appl. Crystallogr. 24:946–950.
Kuhn et al., 1991, Arch. Biochem. Biophys. 286:217–221.
Lambert et al., 1991, Life Sci. 48:69–75.
Langle et al., 1995, Transplantation 59:1542–1549.
Langle et al., 1997, Transplantation 63:1225–1233.
Leu and Wang, 1992, Cancer 70:733–736.
Mancuso et al., 1978, J. Org. Chem. 43:2480–2482.
Matteson, 1960, J. Am. Chem. Soc. 82:4228–4233.
McNeil et al., 1980, J. Am. Chem. Soc. 102:1859–1865.
Merritt et al., 1994, Acta Crystallogr. D50:869–873.
Merritt et al., 1997, Methods Enzymol. 277:505–524.
Moody et al., 1997, J. Urol. 158:942–947.
Modelell et al., 1995, Eur. J. Immunol. 25:1101–1104.
Mourami and Rattan, 1988, Am. J. Physiol. 255:G571–G578.
Narayanan et al., 1994, FASEB J. 8:A360.
Narayanan et al., 1994, J. Med. Chem. 37:885–887.
Navaza, 1994, Acta Crystallogr. A50:157–163.
Zorgniotti et al., 1994, J. Impotence Res. 6:33–35.

* cited by examiner

Fig. 10A
Fig. 10C
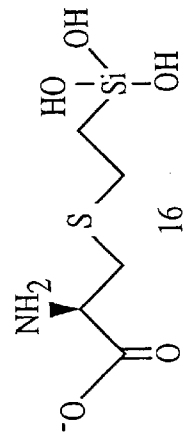
Fig. 10B
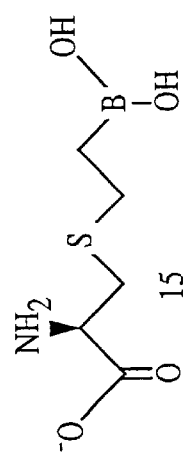
Fig. 10D
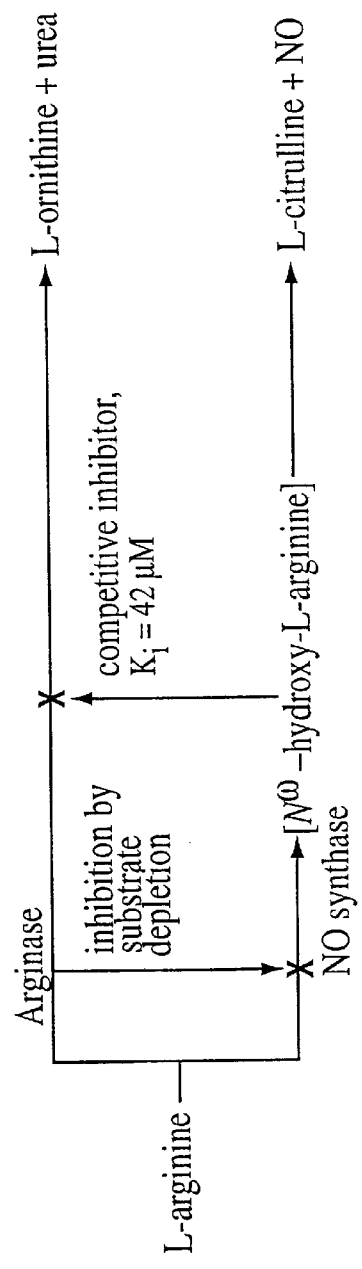
Fig. 11A

| INHIBITOR | n | X |
|---|---|---|
| 7 | 1 | CH$_2$ |
| 12 | 0 | CH$_2$ |
| 15 | 1 | S |

# COMPOSITIONS AND METHODS FOR INHIBITING ARGINASE ACTIVITY

CROSS-REFERENCE TO RELATED APPLICATIONS

This application is a continuation-in-part of international patent application PCT/US98/21430, filed Oct. 9, 1998. This application is also entitled to priority pursuant to 35 U.S.C. §119(e) to U.S. provisional patent application No. 60/061,607, which was filed on Oct. 10, 1997.

STATEMENT REGARDING FEDERALLY SUPPORTED RESEARCH OR DEVELOPMENT

This research was supported in part by U.S. Government funds (U.S. National Institutes of Health grants number GM45614 and DK44841), and the U.S. Government may therefore have certain rights in the invention.

BACKGROUND OF THE INVENTION

The invention relates generally to enzyme inhibitors, more particularly to inhibitors of the enzyme designated arginase.

Each individual excretes roughly ten kilograms of urea per year, as a result of the hydrolysis of arginine in the final cytosolic step of the urea cycle (Krebs et al., 1932, Hoppe-Seyler's Z. Physiol. Chem. 210:33–66). The activity of the liver enzyme, arginase, permits disposal of nitrogenous wastes which result from protein catabolism (Herzfeld et al., 1976, Biochem. J. 153:469–478). In tissues which lack a complete complement of the enzymes which catalyze the reactions of the urea cycle, arginase regulates cellular concentrations of arginine and ornithine, which are used for biosynthetic reactions (Yip et al., 1972, Biochem. J. 127:893–899). Arginine is used, by way of example, in the synthesis of nitric oxide. In macrophages, arginase activity is reciprocally coordinated with the activity of the enzyme, nitric oxide synthase. Reciprocal coordination of the activities of arginase and nitric oxide (NO) gynthage modulates NO-dependent cytotoxicity (Corraliza et al., 1995, Biochem. Biophys. Res. Commun. 206:667–673; Daghigh et al., 1994, Biochem. Biophys. Res. Commun. 202:174–180; Chénais et al., 1993, Biochem. Biophys. Res. Commun. 196:1558–1565; Klatt et al., 1993, J. Biol. Chem. 268:14781–14787; Keller et al., 1991, Cell. Immunol. 134:249–256; Albina et al., 1995, J. Immunol. 155:4391–4396).

Synthesis and evaluation of non-reactive arginine analogs for use as enzyme inhibitors or receptor antagonists is a rapidly growing area of medicinal chemical research (Griffith et al., 1995, Annu. Rev. Physiol. 57:707–736; Gross et al., 1990, Biochem. Biophys. Res. Commun. 170:96–103; Hibbs et al., 1987, J. Immunol. 138:550–565; Lambert et al., 1991, Life Sci. 49:69–79; Olken et al., 1992, J. Med. Chem. 35:1137–1144; Feldman et al., 1993, J. Med. Chem. 36:491–496; Narayanan et al., 1994, FASEB J. 8:A360; Narayanan et al., 1994, J. Med. Chem. 37:885–887; Moore et al., 1994, J. Med. Chem. 37:3886–3888; Moynihan et al., 1994, J. Chem. Soc. Perkin Trans.769–771; Robertson et al., 1995, J. Bioorganic Chem. 23:144–151).

To date, the X-ray crystal structure of one of the enzymes of mammalian arginine catabolism, namely rat liver arginase, is available (Kanyo et al., 1996, Nature 383:554–557). Rat liver arginase is a trimeric metalloenzyme which contains a bi-nuclear manganese cluster in the active site of each subunit. This bi-nuclear cluster is required for maximal catalytic activity (Reczkowski et al., 1992, J. Am. Chem. Soc. 114:10992–10994).

As noted herein, arginase catalyzes divalent cation-dependent hydrolysis of L-arginine to form L-ornithine and urea. The enzyme is currently known to serve three important functions: production of urea, production of ornithine, and regulation of substrate arginine levels for nitric oxide synthase (Jenkinson et al., 1996, Comp. Biochem. Physiol. 114B:107–132; Kanyo et al., 1996, Nature 383:554–557; Christianson, 1997, Prog. Biophys. Molec. biol. 67:217–252). Urea production provides a mechanism to excrete nitrogen in the form of a highly soluble, non-toxic compound, thus avoiding the potentially dangerous consequences of high ammonia levels. L-ornithine is a precursor for the biosynthesis of polyamines, spermine, and spermidine, which have important roles in cell proliferation and differentiation. Finally, arginase modulates production of nitric oxide by regulating the levels of arginine present within tissues.

Since both NO synthase and arginase compete for the same substrate, the possibility of reciprocal regulation of both arginine metabolic pathways has recently been explored (Modelell et al., 1995, Eur. J. Immunol. 25:1101–1104; Wang et al., 1995, Biochem. Biophys. Res. Commun. 210:1009–1016). Furthermore, $N^\omega$-hydroxy-L-arginine (L-HO-Arg), an intermediate in the NO synthase reaction (Pufahl et al., 1992, Biochemistry 31:6822–6828; Klau et al, 1993, J. Biol. Chem. 268:14781–14787; Furchgom, 1995, Annu. Rev. Pharmacol. Toxicol., 35:1–27; Yamaguchi et al., 1992, Fur. J. Biochem., 204:547–552; Pufahl et al., 1995, Biochemisty 34:1930–1941), is an endogenous arginase inhibitor (Chenais et al., 1993, Biochem. Biophys. Res. Commun., 196:1558–1565; Buga et al., 1996, Am. J. Physiol. Heart Circ. Physiol. 271:H1988–H1998 Daghigh et al., 1994, Biochem. Biophys. Res. Commun, 202;174–180; Boucher et al., 1994, Biochem. Biophys. Res. Commun. 203:1614–1621). The phenomenon of reciprocal regulation between arginase and NO synthase has only recently been examined (Chakder and Rattan, 1997, J. Pharmacol. Exp. Ther. 282:378–384; Langle et al., 1997, Transplantation 63:1225–1233; Langle et al., 1995, Transplantation 59:1542–1549). In the internal anal sphincter (IAS), it was shown that exogenous administration of arginase attenuates NO synthase-mediated non-adrenergic and non-cholinergic (NANC) nerve-mediated relaxation (Chakder and Rattan, 1997, J. Pharmacol. Exp. Ther. 282:378–384).

An excess of arginase has recently been associated with a number of pathological conditions that include gastric cancer (Wu et al., 1992, Life Sci. 51:1355–1361; Leu and Wang, 1992, Cancer 70:733–736; Straus et al., 1992, Clin. Chim. Acta 210:5–12; Ikemoto et al, 1993, Clin. Chem. 39:794–799; Wu et al., 1994, Dig. Dis. Sci. 39:1107–1112), certain forms of liver injury (Ikemoto et al., 1993, Clin. Chem. 39:794–799), and pulmonary hypertension following the orthotopic liver transplantation (Langle et al., 1997, Transplantation 63:1225–1233; Langle et al., 1995, Transplantation 59:1542–1549). Furthermore, high levels of arginase can cause impairment in NANC-mediated relaxation of the IAS (Chakder and Rattan, 1997, J. Pharmacol. Esp. Ther. 282:378–384). Previous studies have demonstrated that arginase pre-treatment causes significant suppression of the NANC nerve-mediated relaxation of the IAS (Chakder and Rattan 1997, J. Pharmacol. Exp. Ther. 282:378–384) that is mediated primarily via the L-arginine-NO synthase pathway (Rattan and Chakder, 1992, Am. J. Physiol. Gastrointest. Liver Physiol. 262: G107–G112; Rattan and Chakder, 1992, Gastroenterology 103:43–50). Impairment in NANC relaxation by excess arginase may be related to L-arginine depletion (Wang et al., 1995, Eur. J. Immunol. 25:1101–1104). Furthermore, suppressed relaxation could be restored by the arginase inhibitor L-HO-Arg. It is possible, therefore, that patients with certain conditions associated with an increase in arginase activity may stand to benefit from treatment with arginase inhibitors. However, an arginase inhibitor such as L-OH-Arg can not be selective since it also serves as a NO synthase substrate (Pufahl et al., 1992, Biochemistry 31:6822–6828; Furchgott, 1995, Annu. Rev. Pharmacol. Toxicol. 25:1–27; Pufahl et al, 1995, Biochemistry 34:1930–1941; Chemais et al., 1993, Biochem. Biophys. Res. Commun. 196:1558–1565; Boucher et al., 1994, Biochem. Biophys. Res. Commun. 203:1614–1621; Griffith and Stuehr, 1995, Annu. Rev. Physiol. 57:707–736). Because of this, the exact role of arginase in pathophysiology and the potential therapeutic actions of arginase inhibitors remains undetermined.

Erectile dysfunction afflicts one-half of the male population over the age of forty. This malady often results from defects in the complex cascade of enzyme-catalyzed reactions governing blood flow into and out of the corpus cavemosum, a chamber of muscular, spongy tissue that becomes engorged with blood in the erect penis. Defects that compromise cavemosal blood flow often occur as secondary complications related to other health conditions, such as heart disease, hypertension, diabetes, use of certain medications, and the like.

A need remains for inhibitors of arginase activity, which are useful for treating diseases or disorders characterized either by abnormally high arginase activity in a tissue of a mammal or by abnormally low nitric oxide synthase activity in a tissue of the mammal.

SUMMARY OF THE INVENTION

The invention include a composition comprising an arginase inhibitor having the structure $$HOOC\text{—}CH(NH_2)\text{—}X^1\text{—}X^2\text{—}X^3\text{—}X^4\text{—}B(OH)_2$$

wherein each of $X^1$, $X^2$, $X^3$, and $X^4$ is selected from the group consisting of —(CH$_2$—)—, —S—, —O—, —(NH)—, and —(N-alkyl)—, except $X^2$ is not —S— when each of $X^1$, $X^3$, and $X^4$ is —(CH$_2$)—. In a preferred embodiment, the inhibitor is 2(S)-amino-6-boronohexanoic acid (ABHA), which has the structure $$HOOC\text{—}CH(NH_2)\text{—}CH_2\text{—}CH_2\text{—}CH_2\text{—}CH_2\text{—}CH_2\text{—}B(OH)_2.$$

The composition can further comprise a pharmaceutically acceptable carrier.

Also included in the invention is a pharmaceutical composition comprising a pharmaceutical acceptable carrier and an arginase inhibitor having the structure $$HOOC\text{—}CH(NH_2)\text{—}X^1\text{—}X^2\text{—}X^3\text{—}X^4\text{—}B(OH)_2$$

wherein each of $X^1$, $X^2$, $X^3$, and $X^4$ is selected from the group consisting of —(CH$_2$)—, —S—, —O—, —(NH)—, and —(N-alkyl)—. For example, the structure can be one of $$HOOC\text{—}CH(NH_2)\text{—}CH_2\text{—}CH_2\text{—}CH_2\text{—}CH_2\text{—}B(OH)_2$$

and $$HOOC\text{—}CH(NH_2)\text{—}CH_2\text{—}S\text{—}CH_2\text{—}CH_2\text{—}B(OH)_2.$$

The invention further includes a method of inhibiting arginase. This method comprises contacting the arginage with a compound having the structure $$HOOC\text{—}CH(NH_2)\text{—}X^1\text{—}X^2\text{—}X^3\text{—}X^4\text{—}B(OH)_2.$$

wherein each of $X^1$, $X^2$, $X^3$, and $X^4$ is selected from the group consisting of —(CH$_2$)—, —S—, —O—, —(NH)—, and —(N-alkyl)—. The arginase can, for example, be a yeast arginase or a mammalian arginase. When the arginase is mammalian arginase, the arginase is human arginase such as a human type II arginase (e.g. human penile arginase).

Also included in the invention is a method of inhibiting arginase in a mammal. This method comprises administering to the mammal (e.g. a human) a composition comprising a pharmaceutically acceptable carrier and an arginase inhibitor having the structure $$HOOC\text{—}CH(NH_2)\text{—}X^1\text{—}X^2\text{—}X^3\text{—}X^4\text{—}B(OH)_2$$

wherein each of $X^1$, $X^2$, $X^3$, and $X^4$ is selected from the group consisting of —(CH$_2$)—, —S—, —O—, —(NH)—, and —(N-alkyl)—. The structure can, for example, be either of $$HOOC\text{—}CH(NH_2)\text{—}CH_2\text{—}CH_2\text{—}CH_2\text{—}CH_2\text{—}B(OH)_2$$

and $$HOOC\text{—}CH(NH_2)\text{—}CH_2\text{—}S\text{—}CH_2\text{—}CH_2\text{—}B(OH)_2.$$

When the mammal is a human, the human can be one who comprises either a tissue which exhibits an abnormally high level of arginase activity or a tissue which exhibits an abnormally low level of nitric oxide synthase activity.

Also included in the invention is a method of treating an arginase-related disorder in a human. This method comprises administering to the human a composition comprising a pharmaceutically acceptable carrier and an arginase inhibitor having the structure $$HOOC\text{—}CH(NH_2)\text{—}X^1\text{—}X^2\text{—}X^3\text{—}X^4\text{—}B(OH)_2$$

wherein each of $X^1$, $X^2$, $X^3$, and $X^4$ is selected from the group consisting of —(CH$_2$)—, —S—, —O—, —(NH)—, and —(N-alkyl)—. The disorder can, for example, be one selected from the group consisting of a disorder associated with an abnormally low level of nitric oxide synthase activity in a tissue of the human and a disorder associated with an abnormally high level of arginine activity in a tissue of the human. Examples of such disorders include heart disease, systemic hypertension, pulmonary hypertension, erectile dysfunction, autoimmune encephalomyelitis, chronic renal failure, gastrointestinal motility disorders, gastric cancers, reduced (or insufficient) hepatic blood flow, and cerebral vasospasm.

The invention further includes a method of relaxing smooth muscle in a mammal. This method comprises administering to the mammal a composition comprising a pharmaceutically acceptable carrier and an arginase inhibitor having the structure $$HOOC\text{—}CH(NH_2)\text{—}X^1\text{—}X^2\text{—}X^3\text{—}X^4\text{—}B(OH)_2$$

wherein each of $X^1$, $X^2$, $X^3$, and $X^4$ is selected from the group consisting of —(CH$_2$)—, —S—, —O—, —(NH)—, and —(N-alkyl)—. The smooth muscle which is relaxed according to this method can be one of a gastrointestinal smooth muscle, anal sphincter smooth muscle, esophageal sphincter muscle, corpus cavernosum, sphincter of Oddi, arterial smooth muscle, heart smooth muscle, pulmonary smooth muscle, kidney smooth muscle, uterine smooth muscle, vaginal smooth muscle, cervical smooth muscle, placental smooth muscle, and ocular smooth muscle.

In addition, the invention includes a method of making a compound having the structure

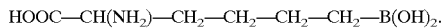

This method comprises contacting a molecule of the tert-butyl ester of 2(S)-N-(tert-butyloxycarbonyl)-6-[(1S,2S,3R,5S)-(+)-pinanedioxaboranyl]-hexanoic acid in an organic solvent (e.g. $CH_2Cl_2$) with $BCl_3$.

Also included in the invention is a method of making a compound having the structure

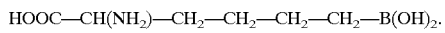

This method comprises the steps of
(a) mixing a solution of the tert-butyl ester of 2(S)-N-(tert-butyloxycarbonyl)-glutamic acid in tetrahydrofuran with triethylamine and ethyl chloroformate to produce a first mixture, removing the resulting trimethylammonium hydrochloride salt by filtration, and treating the remaining mixture with an aqueous solution of sodium borohydride to provide a first compound, wherein the first compound is the tert-butyl ester of 2(S)-N-(tert-butyloxycarbonyl)-5-hydroxypontanoic acid;
(b) subjecting the first compound to Swern oxidation to produce a second compound;
(c) subjecting the second compound to a Wittig reaction in the presence of triphenylphosphonium methylide to produce a third compound;
(d) mixing a solution of $BH_3$ with the third compound in the presence of tetrahydrofuran to produce a second mixture,
(e) adding (1S,2S,3R,5S)-(+)-pinanediol to the second mixture to produce a fourth compound, wherein the fourth compound is the tert-butyl ester of 2(S)-N-(tert-butyloxycarbonyl)-6-[(1S,2S,3R,5S)-(+)-pinanedioxaboranyl]-hexanoic acid; and
(f) mixing the fourth compound with $BCl_3$ in the presence of $CH_2Cl_2$ to produce the compound.

Also included in the invention is a method of identifying an arginase inhibitor antagonist, the method comprising the steps of
(a) inducing relaxation of a muscle in vitro;
(b) reversing the relaxation by contacting the muscle with arginase;
(c) adding an arginase inhibitor to the muscle so reversed to renew relaxation of the muscle in the presence or absence of a test compound; and
(d) measuring the level of renewed relaxation of the muscle, wherein a lower level of renewed relaxation of the muscle in the presence of the test compound, compared with the level of renewed relaxation of the muscle in the absence of the test compound, is an indication that the test compound is an arginase inhibitor antagonist.

In another aspect, the invention relates to a method of alleviating erectile dysfunction in a human. In this method, a pharmaceutical composition is administered to the human, the composition comprising an arginase inhibitor having the structure

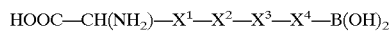

wherein each of $X^1$, $X^2$, $X^3$, and $X^4$ is selected from the group consisting of —($CH_2$)—, —S—, —O—, —(NH)—, and —(N-alkyl)—. Preferably, the arginase inhibitor is ABHA.

BRIEF DESCRIPTION OF THE DRAWINGS

FIG. 3, comprising In FIG. 3A, the hydrogen bond between Oδ2 of $Mn^{2+}_A$ ligand Asp 128 and bridging solvent, which is represented by a sphere, is indicated by a dashed line. In FIG. 3B, the manganese coordination interactions are depicted, with coordination bond lengths indicated in angstroms.

FIG. 8, comprising

FIG. 10 is a diagram of Scheme 1 depicting the chemical structures of compounds 7 (ABHA), 12, 15 (BEC), and 16.

FIG. 11A is a scheme illustrating the reciprocal coordination of NO synthase and arginase activities.

FIG. 13, comprising

FIG. 14 comprising

FIGS. 15A and 15B, is two graphs depicting the titration of arginase by ABHA ("7") in a solution comprising 100 micromolar $MnCl_2$ and 50 millimolar bicine (pH 8.5) at 25° C. FIG. 15A contains the raw data obtained by titration of 0.0358 millimolar arginase with 30×2.5 microliters injections of 1.5 millimolar ABHA. In FIG. 15B, the area under each peak was integrated and plotted against [ABHA]/[arginase]. The solid line represents the best fit of the experimental data using non-linear least squares fitting, indicating a stoichiometry (n) of 1.07 moles of bound ABHA per mole of arginase monomer, an association constant ($K_a$) of 8.89×10$^6$ inverse molar, and an enthalpy change ($\Delta H$) of –12.97 kilocalories per mole.

FIGS. 16A and 16B, is a pair graphs depicting the titration of arginase by compound 15 in a solution comprising 100 micromolar $MnCl_2$ and 50 millimolar bicine (pH 8.5) at 25° C. FIG. 16A depicts the raw data obtained by titration of 0.0358 millimolar arginase with 40×2.5 microliters injections of 1.5 millimolar compound 15. In FIG. 16B the area under each peak was integrated and plotted against [15]/[arginase]. The solid line represents the best fit of the experimental data using non-linear least squares fitting, indicating a stoichiometry (n) of 0.964 moles of bound 15 per mole of arginase, an association constant ($K_a$) of 4.50×10$^5$ inverse molar, and an enthalpy change ($\Delta H$) of –12.75 kilocalories per mole.

FIG. 28, comprising

FIG. 29, comprising FIG. 29A is an Omit electron density map, generated using BOBSCRIPT and Raster3D software (Esnouf, 1997, J. Mol. Graphics 15:132–134; Merritt et al., 1997, Methods Enzymol. 277:505–524) of ABHA in the arginase active site averaged over the two monomers in the asymmetric unit and averaged over the two twin domains A and B, as described herein. The map in FIG. 29A is contoured at 7.7σ and selective active site residues are indicated. Atoms are color-coded as follows: C (yellow), O (red), N (blue, and B (pale green). Water molecules in FIG. 29A are shown as red spheres. FIG. 29B is a summary of arginase-ABNA interactions. FIG. 29C is a diagram which illustrates stabilization of the tetrahedral intermediate (and flanking transition states) in the arginase mechanism, based on the binding mode of ABHA.

FIGS. 30A, 30B, and 30C, illustrates the effect of ABHA on NANC nerve-mediated relaxation in penile corpus cavernosum smooth muscle tissue. FIG. 30A illustrates representative polygraph tracing of responses to EFS in the absence and presence of 1 millimolar ABHA. In FIG. 30A, tissue tone is represented as grams of tension on the ordinate. In the absence of electrical stimulation, ABHA caused moderate relaxation, due to basal activity of NO synthase. FIG. 30B is a bar graph which summarizes data gathered in organ bath experiments. All responses in the presence of ABHA were significantly greater ($p \leq 0.05$), with the exception of the response obtained at 1 Hertz in the presence of 0.1 millimolar ABHA. FIG. 30C is a bar graph which illustrates increase in relaxation caused by ABHA, relative to control responses. Enhancement by ABHA was statistically significant ($p \leq 0.05$) at all concentrations and frequencies tested.

DETAILED DESCRIPTION

The invention is based upon the discovery of compounds which inhibit the enzymatic activity of arginase. These compounds, which were not previously known to inhibit this enzyme (and at least some of which were apparently not previously known to have any use), are useful for a variety of applications in medicine and research.

Compositions and methods for inhibiting the activity of arginase including, but not limited to, yeast and mammalian arginase, are described herein. Inhibition of mammalian arginase activity using the Moronic acid-based arginine analog 2(S)-amino-6-boronohexanoic acid (ABHA) is also described herein, as is inhibition of arginase using the boronic acid based arginine analog S-(2-boronoethyl)-L-cysteine (BEC).

The compositions described herein can be used to inhibit arginase activity in vitro or in vivo, for example, in a human. These compositions can also be used to treat a disorder characterized either by abnormally high arginase activity in a tissue of a mammal or by abnormally low nitric oxide synthase activity in a tissue of the mammal, preferably a human.

The composition of the invention comprises an arginase inhibitor having the structure

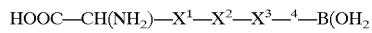
HOOC—CH(NH$_2$)—X$^1$—X$^2$—X$^3$—$^4$—B(OH)$_2$ wherein each of X$^1$, X$^2$, X$^3$, and X$^4$ is selected from the group consisting of —(CH$_2$)—, —S—, —O—, —(NH)—, and —(N-alkyl)—, except X$^2$ is not —S— when each of X$^1$, X$^3$, and X$^4$ is —(CH$_2$)—.

In one aspect, the arginase inhibitor has the structure

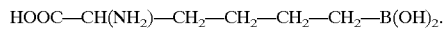
HOOC—CH(NH$_2$)—CH$_2$—CH$_2$—CH$_2$—CH$_2$—B(OH)$_2$.

Figure 8B:
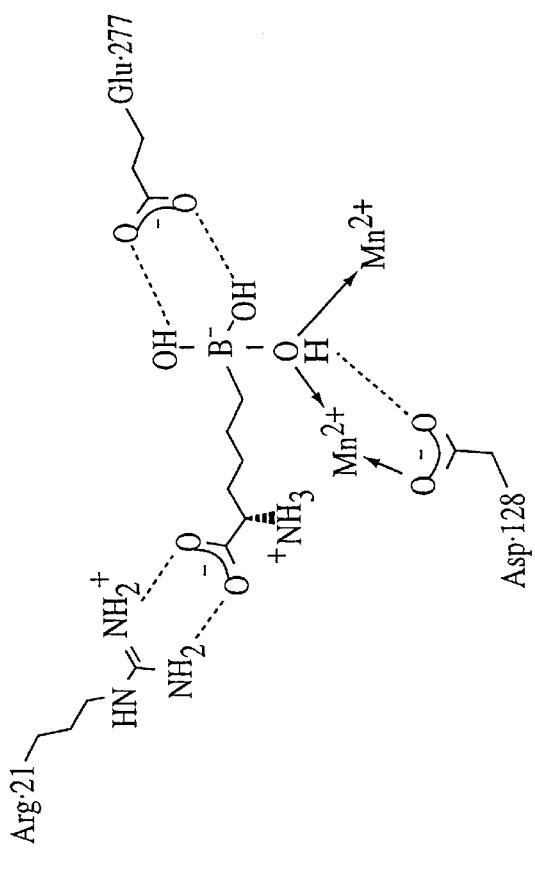
FIGS. 8A and 8B, is a pair of images which illustrate the similarity between the interaction of arginase with the proposed tetrahedral intermediate of arginase-catalyzed arginine hydrolysis, depicted in FIG. 8A, and the interaction of arginase with the proposed the proposed tetrahedral conformation of hydrated ABHA, depicted in FIG. 8B.

This compound is 2(S)-amino-6-boronohexanoic acid (ABHA). ABHA is alternatively referred to herein as compound 7. Data presented herein confirm that ABHA is a potent inhibitor of arginase activity. The conformation of the hydrated form of ABHA resembles a transition state intermediate postulated to be formed during the arginine hydrolysis reaction catalyzed by arginase. The tetrahedral structure around the boron atom of hydrated arginase (e.g. ABHA, as depicted in FIG. 8B) closely resembles the tetrahedral intermediate formed by hydroxyl ion nucleophilic attack at the guanidinium carbon of arginine.

In a preferred embodiment, the composition of the invention further comprises a pharmaceutically acceptable carrier, go as to render the composition suitable for administration to a human or another mammal.

Also included in the invention is a composition comprising a pharmaceutical acceptable carrier and an arginase inhibitor having the structure

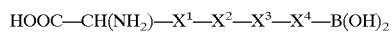
HOOC—CH(NH$_2$)—X$^1$—X$^2$—X$^3$—X$^4$—B(OH)$_2$ wherein each of X$^1$, X$^2$, X$^3$, and X$^4$ is selected from the group consisting of —(CH$_2$)—, —S—, —O—, —(NH)—, and —(N-alkyl)—.

Preferred compositions which also include a pharmaceutically acceptable carrier, include ABHA and a compound having the structure

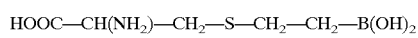
HOOC—CH(NH$_2$)—CH$_2$—S—CH$_2$—CH$_2$—B(OH)$_2$

This inhibitor is S-(2-boronoethyl)-L-cysteine (BEC). BEC is also referred to herein as compound 15.

Any physiologically acceptable anion can be used as a counter-ion when an arginase inhibitor described herein is prepared in the form of a salt. Physiologically acceptable anions are known in the art, and include, for example, chloride, acetate, and citrate.

The invention includes a method of inhibiting arginase, the method comprising contacting a composition comprising an arginase inhibitor described herein with an arginase enzyme, such as a yeast arginase enzyme or a mammalian arginase enzyme. When the enzyme is a mammalian arginase, the arginase is preferably a human arginase enzyme, and more preferably a human type II (i.e. non-hepatic type) arginase.

"Inhibition" of arginase by an arginase inhibitor means reduction in the level of arginase activity in the presence of the inhibitor, compared with the level of arginase activity in the absence of the inhibitor.

Arginase can be inhibited in yeast by contacting the yeast with the composition of the invention. Inhibition of arginase in yeast serves to minimize urea production during fermentation of alcoholic beverages.

In addition, the compositions of the invention are useful as anti-fungicides in agriculturally or otherwise economically important plant life. The composition of the invention can be administered to the plant by spraying or other means well known in the art of plant biology.

Arginase activity can be inhibited in a mammal, for example, by administering a pharmaceutical composition comprising an arginase inhibitor described herein to the mammal.

Thus, the composition of the invention can be used to treat a disorder in a mammal, wherein the disorder is associated with expression of an abnormally high level of arginase activity in a tissue of the mammal. Because NO synthase activity is regulated in a reciprocal fashion with respect to arginase activity in mammals, more particularly humans, the composition of the invention can be used to treat a disorder in a mammal, wherein the disorder is associated with expression of an abnormally low level of NO synthase activity in a tissue of the mammal. Since the reciprocal interaction of arginase and NO synthase has implications for the function of smooth muscle as described in further detail herein in Example 4, the use of the compounds described herein for the regulation of smooth muscle activity in an animal is also contemplated in the invention. Of course, a composition which comprises an arginase inhibitor described herein can also be used to inhibit arginase in a mammal having normal levels of arginase and NO synthase activity, particularly where the physiological which is desired to be effected is one which is affected by arginase or NO synthase activity, or where a disorder which is not caused by aberrant arginase or NO synthase activity levels can nonetheless be alleviated or inhibited by inhibiting arginase activity (e.g. certain forms of erectile dysfunction).

An "abnormally high level of arginase activity" means a level of arginase activity which exceeds the level found in normal tissue when the normal tissue does not exhibit an arginase related disorder phenotype.

An "abnormally low level of NO synthase activity" means a level of NO synthase activity which is lower than that found in normal tissue when the normal tissue does not exhibit an NO synthase related disorder phenotype.

An increase in arginase activity has been associated with the pathophysiology of a number of conditions including impairment in non-adrenergic and non-cholinergic (NANC) nerve-mediated relaxation of gastrointestinal smooth muscle. An arginase inhibitor can be used to alleviate such impairment by administering the inhibitor to a mammal experiencing such impairment or a mammal which is anticipated to experience such impairment (e.g. a human afflicted with a gastrointestinal motility disorder).

Thus, the invention includes a method of enhancing smooth muscle relaxation comprising contacting the smooth muscle with an arginase inhibitor. The smooth muscle is preferably within the body of an animal and the arginase inhibitor is preferably ABHA or BEC. The type of smooth muscle to be relaxed includes, but is not limited to, gastrointestinal smooth muscle, anal sphincter smooth muscle, esophageal sphincter muscle, sphincter of Oddi, arterial smooth muscle, heart smooth muscle, pulmonary smooth muscle, kidney smooth muscle, uterine smooth muscle, vaginal smooth muscle, cervical smooth muscle, placental smooth muscle, and ocular smooth muscle. When the smooth muscle is gastrointestinal smooth muscle, the type of gastrointestinal smooth muscle includes, but is not limited to, the internal anal sphincter muscle.

In an important embodiment, the invention relates to use of an arginase inhibitor described herein for enhancing penile erectile function in a mammal (preferably a human) or for alleviating erectile dysfunction in a mammal.

NO is an important regulator of erectile function and mediates NANC neurotransmission in penile corpus cavernosum smooth muscle, leading to rapid relaxation, which in turn leads to erection. NO synthase, which catalyzes oxidation of L-arginine to form L-citrulline and NO, is for this reason a key enzyme in penile smooth muscle physiology.

Arginase catalyzes hydrolysis of L-arginine to form L-ornithine and urea. Arginase regulates NO synthase activity by affecting the amount of L-arginine available for oxidation catalyzed by NO synthase activity. Thus, inhibition of arginase activity can enhance NO synthase activity, thereby enhancing NO-dependent smooth muscle relaxation in the corpus cavernosum and enhancing penile erection.

When the smooth muscle in within the body of the animal, the invention includes a method of alleviating (e.g. reducing the incidence or severity) or inhibiting (e.g. reducing the likelihood of developing, or preventing) an arginase-related disorder in an animal. In a preferred embodiment, the animal is a human.

Disorders which are associated with either an abnormally high level of arginase activity in a tissue of a mammal or an abnormally low level of nitric oxide synthase activity in a tissue of the mammal are known in the art. Disorders to be treated using the compositions of the invention include, but are not limited to, heart disease, systemic hypertension, pulmonary hypertension, erectile dysfunction, autoimmune encephalomyelitis, chronic renal failure, gastrointestinal motility disorders, gastric cancers, reduced hepatic blood flow, and cerebral vasospasm.

To alleviate an arginase-related disorder in a mammal, an arginine inhibitor described herein is administered to a mammal afflicted with the disorder. The inhibitor is preferably administered in combination with one or more pharmaceutically acceptable carriers, as described in further detail herein. The inhibitor (preferably in combination with a carrier) can also be administered to a mammal afflicted with a disorder characterized by aberrant NO synthase activity, or to one which exhibits normal (i.e. non-diseased) levels of arginase and NO synthase activities, but in which inhibition of arginase activity is desired. The invention also contemplates use of an arginase inhibitor in an in vitro arginase inhibition/smooth muscle relaxation functional assay, for the purpose of identifying compounds which affect smooth muscle function. Compounds so identified are considered to be candidate arginase inhibitor antagonists, in that, as described in further detail below, these compounds are identified by their ability to counteract the ABHA or BEC mediated inhibition of arginase activity. For example, there is described herein in Example 4 an assay for smooth muscle activity using the internal anal sphincter muscle and one on the preferred arginase inhibitors of the invention ABHA. In this assay, strips of the internal anal sphincter muscle obtained from a mammal (e.g. an adult opossum) are induced to relax by NANC nerve-mediated relaxation using electrical field stimulation (EFS); relaxation is reversed by contacting the muscle strips with arginase; and reversal of relaxation is accomplished by contacting the muscle with an arginase inhibitor. To identify an arginase inhibitor antagonist, the muscle strips are then subsequently contacted with a test compound. The effect of the test compound on subsequent reversal of muscle relaxation is assessed. Any significant reversal of the relaxation state of the muscle in the presence of the test compound, compared with the relaxation state of the muscle in the absence of the test compound, is an indication that the test compound is an arginase inhibitor antagonist.

An "arginase inhibitor antagonist" means a compound which reduces or prevents inhibition of arginase by an arginase inhibitor.

The invention encompasses preparation and use of pharmaceutical compositions comprising an arginase inhibitor described herein as an active ingredient. Such a pharmaceutical composition can consist of the active ingredient alone, in a form suitable for administration to a subject, or the pharmaceutical composition can comprise the active ingredient and one or more pharmaceutically acceptable carriers, one or more additional ingredients, or some combination of these. Administration of one of these pharmaceutical compositions to a subject is useful for inhibiting arginase activity and thereby treating a disease or disorder associated with arginase enzyme activity, as described elsewhere in the present disclosure. The active ingredient can be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient can be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein can be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, goose, and turkeys, fish including farm-raised fish and aquarium fish, and crustaceans such as farm-raised shellfish.

Pharmaceutical compositions that are useful in the methods of the invention can be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which thee composition is to be administered. By way of example, the composition can comprise between 0.1% and 100% (w/w) active ingredient.

In addition to the active ingredient, a pharmaceutical composition of the invention can further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention can be made using conventional technology.

A formulation of a pharmaceutical composition of the invention suitable for oral administration can be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulfate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pregelatinized maize starch, polyvinylpyrrolidone, and hydroxypropyl methylcellulose. Known lubricating agents include, but are not limited to, magnesium stearate, stearic acid, silica, and talc.

Tablets can be non-coated or they can be coated using known methods to achieve delayed disintegration in the gastrointestinal tract of a subject, thereby providing sustained release and absorption of the active ingredient. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Hard capsules comprising the active ingredient can be made using a physiologically degradable composition, such as gelatin. Such hard capsules comprise the active ingredient, and can further comprise additional ingredients including, for example, an inert solid diluent such as calcium carbonate, calcium phosphate, or kaolin.

Soft gelatin capsules comprising the active ingredient can be made using a physiologically degradable composition, such as gelatin. Such soft capsules comprise the active ingredient, which can be mixed with water or an oil medium such as peanut oil, liquid paraffin, or olive oil.

Liquid formulations of a pharmaceutical composition of the invention which are suitable for oral administration can be prepared, packaged, and sold either in liquid form or in the form of a dry product intended for reconstitution with water or another suitable vehicle prior to use.

Liquid suspensions can be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions can further comprise one or more additional ingredients including, but not limited to, suspending agents, dispersing or wetting agents, emulsifying agents, demulcents, preservatives, buffers, salts, flavorings, coloring agents, and sweetening agents. Oily suspensions can further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents can be prepared in substantially the same manner as liquid suspensions, the primary difference being that the active ingredient is dissolved, rather than suspended in the solvent. Liquid solutions of the pharmaceutical composition of the invention can comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention can be prepared using known methods. Such formulations can be administered directly to a subject, used, for example, to form tablets, to fill capsules, or to prepare an aqueous or oily suspension or solution by addition of an aqueous or oily vehicle thereto. Each of these formulations can further comprise one or more of dispersing or wetting agent, a suspending agent, and a preservative. Additional excipients, such as fillers and sweetening, flavoring, or coloring agents, can also be included in these formulations.

A pharmaceutical composition of the invention can also be prepared, packaged, or sold in the form of oil-in-water emulsion or a water-in-oil emulsion. The oily phase can be a vegetable oil such as olive or arachis oil, a mineral oil such as liquid paraffin, or a combination of these. Such compositions can further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions can also contain additional ingredients including, for example, sweetening or flavoring agents.

A pharmaceutical composition of the invention can be prepared, packaged, or sold in a formulation suitable for rectal administration. Such a composition can be in the form of, for example, a suppository, a retention enema preparation, and a solution for rectal or colonic irrigation.

Suppository formulations can be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations can further comprise various additional ingredients including, but not limited to, antioxidants and preservatives.

Retention enema preparations or solutions for rectal or colonic irrigation can be made by combining the active ingredient with a pharmaceutically acceptable liquid carrier. As is well known in the art, enema preparations can be administered using, and can be packaged within, a delivery device adapted to the rectal anatomy of the subject. Enema preparations can farther comprise various additional ingredients including, but not limited to, antioxidants and preservatives.

A pharmaceutical composition of the invention can be prepared, packaged, or sold in a formulation suitable for vaginal administration. Such a composition can be in the form of, for example, a suppository, an impregnated or coated vaginally-insertable material such as a tampon, a douche preparation, or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation can be made by combining the active ingredient with a pharmaceutically acceptable liquid carrier. As is well known in the art, douche preparations can be administered using, and can be packaged within, a delivery device adapted to the vaginal anatomy of the subject. Douche preparations can further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue, so long as the arginase inhibitor compound is not administered systemically. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations can be prepared, packaged, or sold in a form suitable for bolus administration or for continuous administration. Injectable formulations can be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations can further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions can be prepared, packaged, or sold in the form of a sterile injectable aqueous or oily suspension or solution. This suspension or solution can be formulated according to the known art, and can comprise, in addition to the active ingredient, additional ingredients such as the dispersing agents, wetting agents, or suspending agents described herein. Such sterile injectable formulations can be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration can further comprise one or more of the additional ingredients described herein.

A pharmaceutical composition of the invention can be prepared, packaged, or sold in a formulation suitable for pulmonary administration via the buccal cavity. Such a formulation can comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant can be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant can constitute 50 to 99.9% (w/w) of the composition, and the active ingredient can constitute 0.1 to 20% (w/w) of the composition. The propellant can further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery can also provide the active ingredient in the form of droplets of a solution or suspension. Such formulations can be prepared, packaged, or sold as aqueous or dilute alcoholic solutions or suspensions, optionally sterile, comprising the active ingredient, and can conveniently be administered using any nebulization or atomization device. Such formulations can further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and can further comprise one or more of the additional ingredients described herein.

A pharmaceutical composition of the invention can be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration can comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and can further comprise one or more of the additional ingredients described herein.

A pharmaceutical composition of the invention can be prepared, packaged, or sold in a formulation suitable for ophthalmic administration. Such formulations may, for example, be in the form of eye drops including, for example, a 0.1–1.0% (w/w) solution or suspension of the active ingredient in an aqueous or oily liquid carrier. Such drops can further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which can be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically dosages of the arginase inhibitor which can be administered to an animal, preferably a human, range in amount from 1 microgram to about 100 grams per kilogram of body weight of the animal. While the precise dosage administered will vary depending upon any number of factors, including but not limited to, the type of animal and type of disorder being treated, the age of the animal and the route of administration. Preferably, the dosage of the compound will vary from about 1 milligram to about 10 grams per kilogram of body weight of the animal. More preferably, the dosage will vary from about 10 milligrams to about 1 gram per kilogram of body weight of the animal.

The compound can be administered to an animal as frequently as several times daily, or it can be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disorder being treated, the type and age of the animal, etc.

The invention is now described with reference to the following examples. These examples are provided for the purpose of illustration only and the invention is not limited to these examples, but instead encompasses all variations which are evident as a result of the teaching provided herein.

EXAMPLE 1

Structure of a Unique Bi-nuclear Manganese Cluster in Arginase

The molecular structure of and surrounding the pair of manganese atoms of the arginase monomer was determined by X-ray diffraction and other methods. These data suggest the mechanism by which arginine hydrolysis is catalyzed by arginase and facilitate design of arginase inhibitors which mimic the transition state intermediates of the reaction, as described in Example 2.

The materials and methods used in the experiments presented in this Example are now described.

Crystallization and preliminary X-ray diffraction analysis of rat liver arginase has been reported (Kanyo et al., 1992, J. Mol. Biol. 224:1175–1177). Arginase crystals diffract to 2.1 angstrom resolution and belong to space group $P3_2$, having hexagonal unit-cell dimensions of a=b=88.5 angstroms, and c=106.2 angstroms, and having one 105 kilodalton trimer in the asymmetric unit. Phase determination by multiple isomorphous replacement was hindered by chronic non-isomorphism between native and heavy-atom derivative crystals, as well as non-isomorphism among native crystals themselves. The c-axis length typically ranged from 104 angstroms to 115 angstroms (Kanyo et al., 1992, J. Mol. Biol. 224:1175–1177).

Diffraction data were collected at room temperature on an R-AXIS IIc image plate area detector. Data reduction was performed by MOSFLM (Nyborg et al., 1977, In: *The Rotation Method in Crystallography*, Arndt et al., eds, North-Holland, Amsterdam, 139–152) and CCP4 (Collaborative Computational Project No. 4, 1994, Acta Crystallogr. D50:760–763) as described. For phasing, initial heavy atom positions were determined in difference Patterson maps and refined with the program, PHASES (Burey et al., 1990, Am. Crystallogr. Assoc. Mtg. Prog. Abstr. 18:73). Heavy-atom binding indicated that the non-crystallographic symmetry (NCS) axis of the trimer was tilted about 9° away from a normal to the a–b plane. The model was fit into an electron-density map calculated with solvent-flattened NCS-averaged phases at 3.0 angstrom resolution. Subsequent refinement and rebuilding of the native model was performed using X-PLOR (Brdnger et al., 1987, Science 235:458–460) and O (Jones et al., 1991, Acta. Crystallogr. A47:110–119) algorithms, respectively. Group B factors were refined, and a bulk solvent correction was applied. In the final stages of refinement, the quality of the model was improved by gradually releasing NCS constraints into appropriately weighted restraints as judged by $R_{free}$. Refinement statistics are recorded in Table 1. the final protein model has excellent stereochemistry with only Gln-64 adopting a disallowed $\Phi/\phi$ conformation. This residue is located in a type II' beta-turn between strand 2 and helix B and is characterized by clear and unambiguous electron density.

The results of the experiments presented in this Example are now described.

Arginase is one of the very few enzymes that requires a spin-coupled $Mn^{2+}$—$Mn^{2+}$ cluster for catalytic activity in vitro and in vivo (Reczkowski et al., 1992, J. Am. Chem. Soc. 114:10992–10994). The 2.1 angstrom-resolution crystal structure of trimeric rat liver arginase reveals that this unique metal cluster resides at the bottom of an active-site cleft that is about 15 angstroms deep (Kanyo et al., 1992, J. Mol. Biol. 224:1175–1177). Analysis of the crystal structure of arginase indicates that arginine hydrolysis involves a metal-activated solvent molecule which symmetrically bridges the two $Mn^{2+}$ ions.

metal ion is designated $Mn^{2+}_B$ and is coordinated by His-126 (Nδ), Asp-124 (Oδ2), Asp-232 (Oδ1), Asp-234 (bi-dentate Oδ1 and Oδ2). The coordination of $Mn^{2+}_B$ by arginase and the bridging solvent molecule has an octahedral geometry which is distorted, owing to the bi-dentate coordination of Asp-234. The separation between $Mn^{2+}_A$ and $Mn^{2+}_B$ is about 3.3 angstroms. All metal ligands except Asp-128 make hydrogen-bond interactions with other protein residues, and these interactions contribute to the stability of the metal

TABLE 1

Data collection and refinement statistics.

| Data Set | Resolution (angstroms) | Reflections measured/unique | Completeness (%) overall/outer shell | $R_{merge}$[a] overall/outer shell | $R_{iso}$[b] | Number of Sites | Phasing power[c] | Overall Figure of merit |
|---|---|---|---|---|---|---|---|---|
| Native | 2.1 | 147,454/46,162 | 91.6/58.3 | 0.058/0.365 | — | — | — | — |
| Thimerosal | 3.0 | 39,030/17,363 | 93.7/96.5 | 0.063/0.226 | 0.199 | 6 | 1.51 | — |
| $YbCl_3$ | 3.0 | 29,644/15,182 | 81.9/86.0 | 0.042/0.146 | 0.143 | 6 | 1.46 | — |
| $HgAc_2$ | 3.0 | 26,788/16,202 | 87.2/91.6 | 0.089/0.272 | 0.127 | 6 | 1.78 | — |
| | | | | | | | | 0.496 |

| Refinement Protein | Atoms | $Mn^{2+}$ ions | Solvent molecules | Resolution (angstroms) | No. Reflections work/free | $R/R_{free}$[d] | Bonds | R.m.s. Angles | Deviations Dihedrals | Improper |
|---|---|---|---|---|---|---|---|---|---|---|
| Native | 7,167 | 6 | 233 | 2.1 | 47,913/ 2,502 | 0.179/ 0.229 | 0.011 Å | 1.6° | 24.7° | 1.6° |

[a]$R_{merge} = \Sigma|I_i - <I_i>|/\Sigma|<I_i>|$, where $I_i$ is the intensity measurement for reflection i, and $<I_i>$ is the mean intensity calculated for reflection i from replicate data.
[b]$R_{iso} = \Sigma||F_{PH}| - |F_P||/\Sigma|F_P|$, where $F_{PH}$ and $F_P$ are the derivative and native structure factors, respectively.
[c]Phasing power = $<F_h>/E$, where $<F_h>$ is the root-mean-square heavy atom structure factor and E is the residual lack of closure error.
[d]$R = ||F_o| - |F_c||/\Sigma|F_o|$, where R and $R_{free}$ are calculated using the working and free reflections sets, respectively. The free reflections, representing 5% of the total, were held aside throughout refinement.

Figure 1:
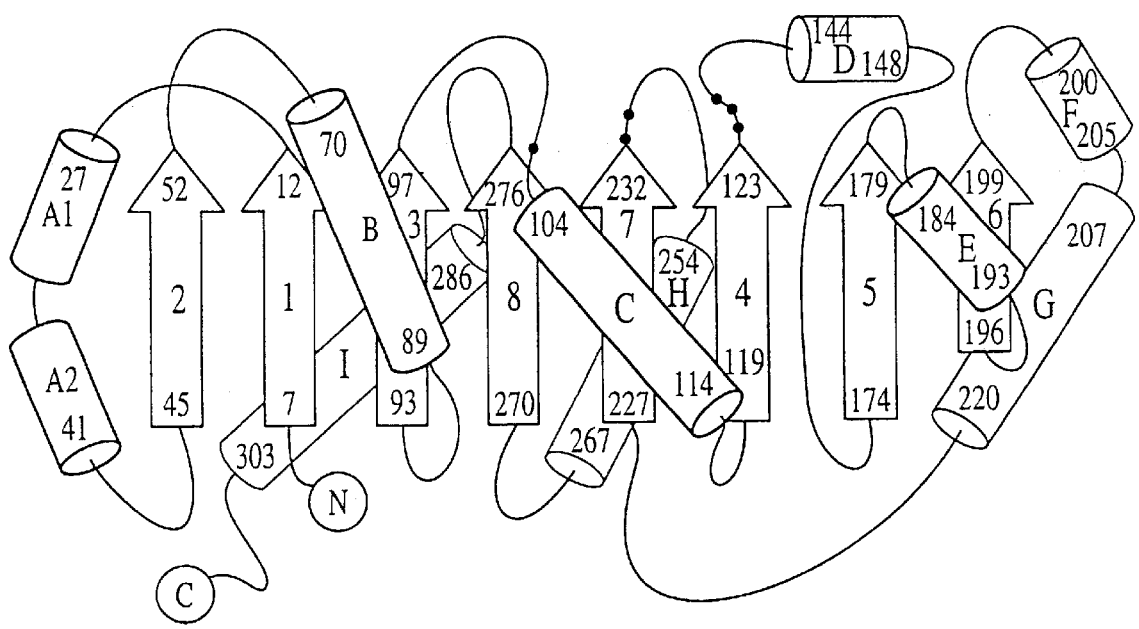
FIG. 1 is a diagram which illustrates the topology of an arginase monomer. Relative locations of metal ligands are indicated by solid circles.
Figure 2:
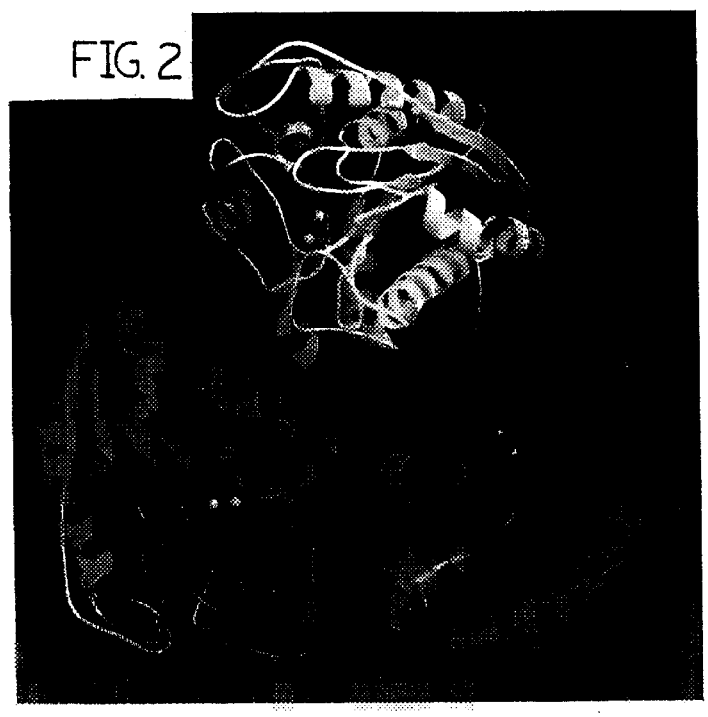
FIG. 2 is an image depicting a ribbon plot of an arginase trimer. The $Mn^{2+}$—$Mn^{2+}$ cluster in the active site of each monomer is represented by a pair of spheres.

The overall folding pattern of the arginase monomer indicates that the protein belongs to the alpha/beta protein class. The arginase monomer has a globular structure, having approximate dimensions of 40×50×50 angstroms. One side of the active-site cleft is partially defined by the central eight-stranded beta-sheet, and the metal binding site is located on one edge of the beta-sheet. Metal ligands are located immediately adjacent to helix C, to strand 4, and to strand 7, as depicted in FIG. 1. The arginase trimer, depicted in FIG. 2, has a relative molecular mass of about 105,000 ($M_r$=105 kilodaltons) and excludes about 2,080 square angstroms of monomer surface area from solvent at each monomer-monomer interface. A majority of inter-monomer contact is mediated by a novel 'S'-shaped oligomerization motif at the carboxyl terminus, as depicted in FIGS. 1 and 2, and the conformation of this segment is stabilized by numerous inter-monomer van der Waals interactions, hydrogen bonds, and salt links. The image in FIG. 2 was generated using MOLSCRIPT (Kraulis et al., 1991, J. Appl. Crystallogr. 24:946–950) and Raster 3D (Bacon et al., 1988, J. Mol. Graph. 6:219–200; Merrit et al., 1994, Acta Crystallogr. D50:869–873).

Figure 4:
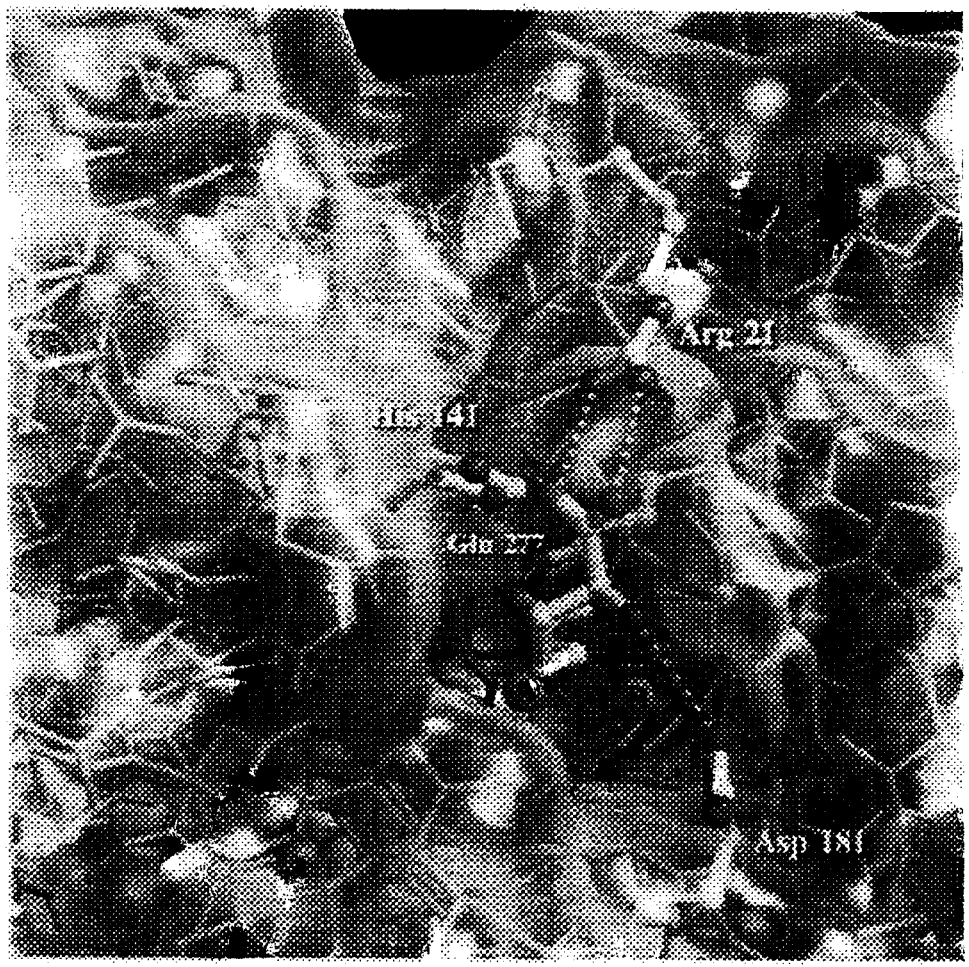
FIG. 4 is an image which depicts a model of arginine binding to the active site of arginase. A salt link between Glu-277 and the substrate guanidinium group can orient the substrate for nucleophilic attack by the metal-bridging solvent molecule. Salt links are indicated by dotted lines. His-141 can serve as a catalytic proton shuttle.

The bi-nuclear manganese cluster is located at the base of an approximately 15 angstrom-deep active site cleft in each monomer, as depicted in FIG. 4. The metal ion that is more deeply situated in the active site cleft is designated $Mn^{2+}_B$ and is coordinated by His-101 (Nδ), Asp-124 (Oδ1), Asp-128 (Oδ1), Asp-232 (Oδ1) and a solvent molecule. The coordination of $Mn^{2+}_A$ by arginase has square pyramidal geometry. A solvent molecule bridges $Mn^{2+}_A$ and $Mn^{2+}_B$ and also donates a hydrogen bond to Asp-128, the Oδ2-O separation distance being about 2.8 angstroms. The second binding site (Christianson et al., 1989, J. Am. Chem. Soc. 111:6412–6419).

Three different types of metal bridging ligands facilitate the observed spin coupling between $Mn^{2+}_A$ and $Mn^{2+}_B$ (Reczkowski et al., 1992, J. Am. Chem. Soc. 114:10992–10994). The carboxylate side chain of Asp-124 is a syn-syn bi-dentate bridging ligand, with Oδ1 coordinated to $Mn^{2+}_A$ and Oδ2 coordinated to $Mn^{2+}_B$ (Rardin et al., 1991, New J. Chem. 15:417–430). The carboxylate side chain of Asp-232 is a monodentate bridging ligand, with Oδ1 coordinated to both $Mn^{2+}_A$ and $Mn^{2+}_B$ with anti- and syn-coordination stereochemistry, respectively (Rardin et al., 1991, New J. Chem. 15:417–430). The Oδ2 oxygen of Asp-232 is about 3.8 angstroms away from $Mn_B^{2+}$. The solvent molecule bridges both manganese ions symmetrically, with the separation distance of the O atom of the solvent from both of $Mn^{2+}_A$ and $Mn^{2+}_B$ being about 2.4 angstroms.

The arginase structure is the first atomic resolution structure determined for a functional metalloenzyme that has a specific catalytic and physiological requirement for two $Mn^{2+}$ ions. Arginase does not use transition metals promiscuously for catalysis, unlike other metalloenzymes, in which $Mn^{2+}$ and, for instance, $Mg^{2+}$ or other metal ions are interchangeable, albeit with some effect on catalytic activity. The identity and oxidation state of the manganese cluster of arginase has been conclusively established by electron paramagnetic resonance spectroscopy (Reczkowski et al., 1992, J. Am. Chem. Soc. 114:10992–10994). The catalytic metal requirement of arginase is rooted in the preferred geometry of manganese coordination, which properly orients the metal-bridging solvent molecule, such that it arginase hydrolysis is catalyzed. Because the metal-bridging solvent molecule must satisfy the coordination preferences of two manganese ions simultaneously, the position of the solvent molecule, and therefore its optimal catalytic activity, is highly sensitive to substitution of one or both $Mn^{2+}$ ions with a different metal ion. Coordination of the solvent molecule to two metal ions, rather than one, enhances the dependence of optimal catalytic activity on proper metal composition of arginase.

Figure 5:
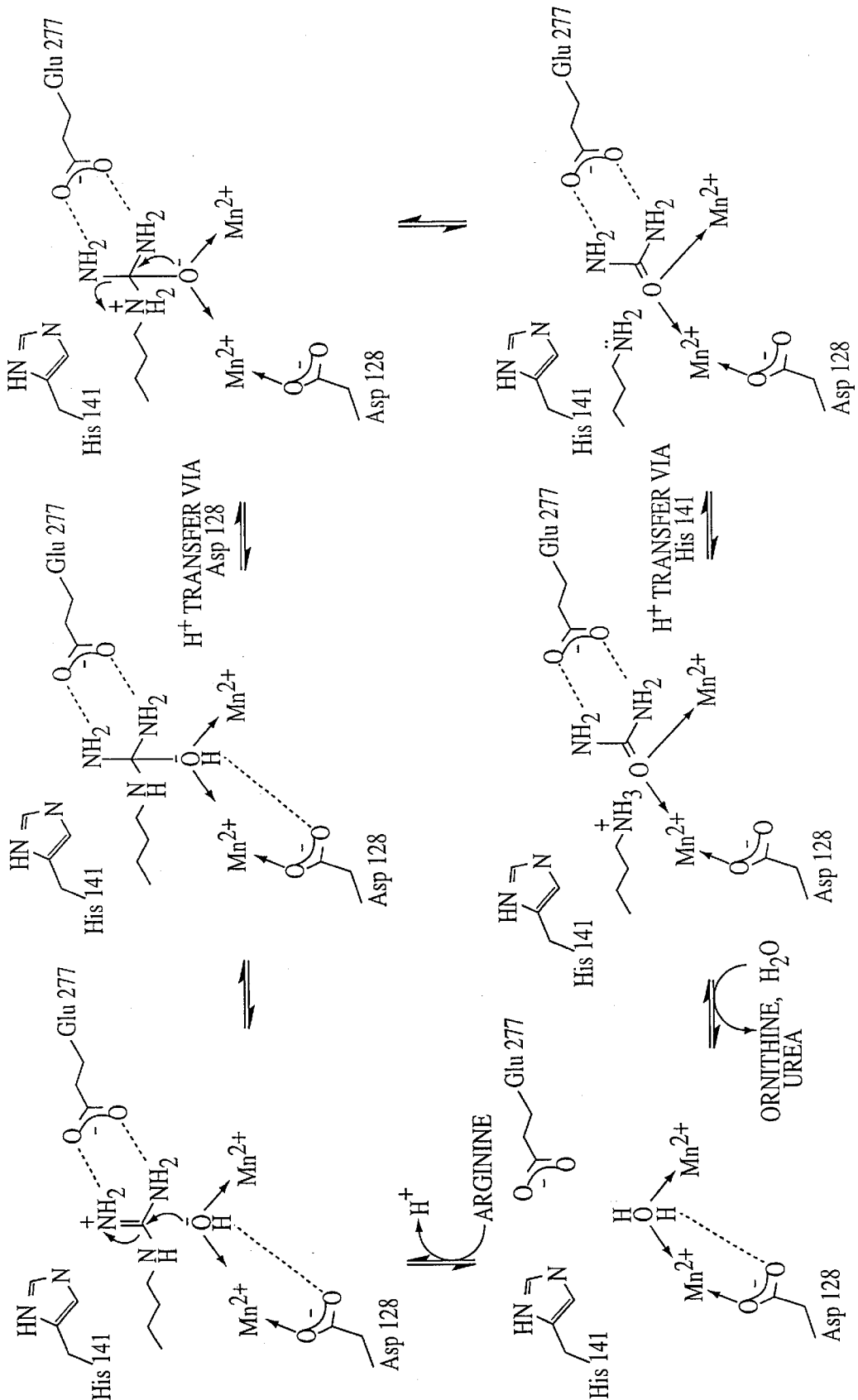
FIG. 5 is an image which illustrates a proposed mechanism of arginase-catalyzed arginine hydrolysis by a metal-activated solvent molecule complexed with the $Mn^{2+}$—$Mn^{2+}$ cluster in the active site of arginase. The alpha-amino and alpha-carboxylate groups of the arginine molecule are omitted for clarity.

Only two other polar residues are found in the immediate vicinity of the active site of arginase, namely Glu-277 and His-141. Glu-277 is located deep in the active-site cleft, about 4.5 angstroms away from $Mn^{2+}_A$ roughly 20° rotation about $\chi_1$ of this side chain yields an ideal salt link with the substrate guanidinium group. Moreover, this salt link positions the electrophilic guanidinium carbon of the substrate directly over the metal-bridging solvent molecule, which is likely to be a nucleophilic hydroxide ion in the active catalyst, as depicted in FIGS. 4 and 5. It is unlikely that the de-protonated substrate guanidinium group binds directly to the metal(s) because of its high $pK_a$ value, namely 13.5. Furthermore, site-directed mutagenesis studies indicate that substrate $K_m$ values are not perturbed by variations in the metal cluster, including metal depletion. This indicates that a substrate-metal interaction does not occur in the Michaelis complex (Cavalli et al., 1994, Biochemistry 33:10652–10657).

The side chain of His-141 is located about midway between the top and the bottom of the active-site cleft. When asparagine is substituted in place of histidine at amino acid position 141 of arginase (i.e. His-141→Asn arginase), the enzyme retains roughly ten percent of its wild type activity (Cavalli et al., 1994, Biochemistry 33:10652–10657). Because its location is only about 4.2 angstroms from the metal-bridging solvent molecule, it is possible that His-141 acts a proton shuttle in arginase catalysis, mediating proton transfer to and from bulk solvent. Direct proton transfer with bulk solvent can be possible in the absence of His-141, which could account for the significant residual catalytic activity of His-141→Asn arginase. A proton shuttle function for His-141 of arginase is analogous to that recently reviewed for His-64 of the zinc metalloenzyme carbonic anhydrase II (Christianson et al., 1996, Acc. Chem. Res. 29:331–339).

Figure 3A:
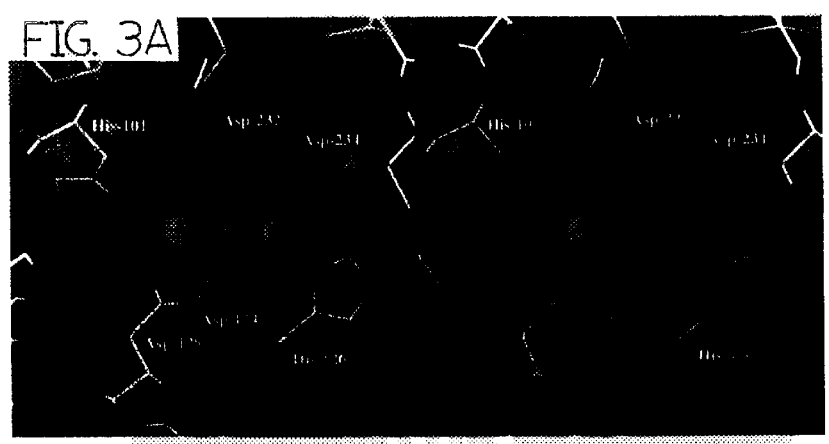
FIGS. 3A and 3B, is a pair of images which depict omit maps of the bi-nuclear manganese cluster of arginase. The maps were calculated using Fourier coefficients $|F_o|–|F_c|$ and phases derived from the final model, less the atoms of metal ligands or metal ions $Mn^{2+}_A$ and $Mn_B^{2+}$.
Figure 3B:

As depicted in FIG. 3, charged amino acid residues are located on opposite sides of the active-site cleft, near the surface of the arginase trimer. The presence of these charged residues can contribute to the exquisite specificity of substrate recognition by arginase. Structure-activity relationships using arginine analogs indicate that electrostatic interactions of arginase with the alpha-substituents of the substrate are critical for catalysis. Deletion of the alpha-carboxylate group or the alpha-amino group of arginine results in $10^2$–$10^5$-fold reductions in $k_{cat}/K_m$ (Reczkowski et al., 1994, Arch. Biochem. Biophys. 312:31–37). Inspection of the arginase active site indicates that the positively charged side chain of Arg-21 interacts with the negatively charged alpha-carboxylate group of the substrate, and that the negatively charged side chain of Asp-181 interacts with the positively charged alpha-amino group of the substrate. A model of arginine binding to the active site of arginase is illustrated in FIG. 4.

A model of arginine hydrolysis by arginase is illustrated in FIG. 5. The ionization of metal-bound water probably reflects the apparent $pK_a$ value of 7.9 observed in the pH rate profile of the enzyme (Kuhn et al., 1991, Arch. Biochem. Biophys. 286:217–221). In the first step of the hydrolytic mechanism, Asp-128 stabilizes the metal-bridging hydroxide ion with a hydrogen bond, while the hydroxide ion performs a nucleophilic attack at the guanidinium carbon of arginine. The resulting tetrahedral intermediate collapses upon proton transfer to the amino group of ornithine. This proton transfer is probably mediated by Asp-128. Subsequently, His-141 shuttles a proton from bulk solvent to the ε-amino group of ornithine prior to dissociation of ornithine from arginase. Upon ornithine dissociation, a water molecule displaces urea, resulting in dissociation of urea from arginase. Metal coordination facilitates the ionization of this water molecule to regenerate a nucleophilic hydroxide ion. Proton transfer from the water molecule to bulk solvent can be mediated by His-141.

It is instructive to consider the chemical function of arginase not only within the context of mammalian nitrogen metabolism, but also within the greater context of the biosphere. In the nitrogen cycle, two bi-nuclear metalloenzymes of different tertiary structure are prominent, namely $Mn_2^{2+}$-arginase and $Ni_2^{2+}$-urease.

The former enzyme provides for abundant release of urea into the environment by mammals, and the latter enzyme allows the use of this urea as a nitrogen source by bacteria, fungi, and plants.

The recent determination of the crystal structure of $Ni_2^{2+}$-urease obtained from the bacterium *Klebsiella aerogenes* (Jabri et al., 1995, Science 268:998–1004) reveals some interesting parallels between these two enzymes which have evolved to catalyze urea chemistry. Both arginase and urease comprise a bi-nuclear transition metal cluster, and both enzymes contain roughly similar constellations of catalytically important carboxylate and imidazole groups within their respective active sites. Interestingly, $Mn_2^{2+}$-substituted urease exhibits catalytic activity, albeit only 2% of that of the native $Ni_2^{2+}$-urease (Park et al., 1996, Biochemistry 35:5345–5352). Preliminary results with $Ni_2^{2+}$-substituted arginase reveal no measurable catalytic activity. Optimal catalytic activity in each system seems to have evolved with high selectivity for one particular bi-nuclear metal cluster of specific composition and structure.

EXAMPLE 2

2(S)-Amino-6-Boronohexanoic Acid (ABHA) is an Effective Inhibitor of Arginase

Using structural data described in Example 1, the structure of an inhibitor of arginase activity was designed which resembles the proposed transition state intermediate of the arginine hydrolysis reaction catalyzed by arginase. The inhibitor was made and tested and it was determined to be a potent inhibitor of arginase activity.

The tetrahedral borate anion is a modest inhibitor of $Mn_2^{2+}$-arginase, a critical metalloenzyme of mammalian nitrogen metabolism. The crystal structure of the arginase-ornithine-borate complex, as described herein, reveals a net displacement of the solvent molecule bridging the bi-nuclear manganese cluster by a borate oxygen atom in the native enzyme active site. This binding mode is reminiscent of the tetrahedral intermediate proposed for arginase-catalyzed arginine hydrolysis, as described in Example 1 herein. ABHA, a boronic acid-based arginine isostere appears to bind to arginase as the tetrahedral boronate anion and mimic the conformation of the tetrahedral arginine-hydrolysis intermediate.

ABHA was synthesized and the ability of ABHA to inhibit arginase-catalyzed arginine hydrolysis was evaluated. ABHA is one of the most potent reversible inhibitors of arginase described to date, having an $IC_{50}$ value of 0.8 micromolar. Complete kinetic characterization of ABHA was complicated by non-linearity of unknown origin, there being no evidence for slow-binding behavior. Competition binding experiments using N-hydroxy-arginine indicate that $K_d$ for ABHA was less than or equal to 0.1 micromolar.

Based on analysis of the crystal structure of the arginase-ornithine-borate complex, a binding model for ABHA was postulated, in which the metal-bridging solvent molecule observed in the native enzyme is displaced by an oxygen atom of the tetrahedral boronic acid anion. Presumably, the boronic acid moiety of ABHA effects inhibition of the enzyme by displacing the metal-bridging solvent molecule in a similar manner.

The materials and methods used in the experiments presented in this Example are now described.

Thin layer chromatography (TLC) was performed using Merck (Merck & Co., West Point, Pa.) silica gel 60 $F_{254}$ glass plates. Compounds with tert-butyloxycarbonylamino groups or free amino groups were visualized on TLC plates by applying a ninhydrin solution (comprising 0.1% (w/v) ninhydrin in 95% (v/v) n-butanol, 4.5% (v/v) water, 0.5% (v/v) glacial acetic acid) to the plates and then heating the plates until color evolved.

Column chromatography was performed using a column packed with Merck (Merck & Co., West Point, Pa.) silica gel 60 (230–240 mesh ASTM) under positive nitrogen pressure.

Melting points were determined visually in an open capillary on a Thomas Hoover capillary melting point apparatus.

$^1$H-NMR and $^{11}$B-NMR spectra were measured using a Bruker AC-250 (250 megahertz) NMR spectrometer and a Bruker AC-200 (200 megahertz) NMR spectrometer, respectively. Chemical shifts were expressed in parts per million (ppm) and referenced either $CDCl_3$ or $CD_3OD$.

Arginase activity was assessed using the ($^{14}$C-guanidino)-arginine assay of Rüegg et al. (1980, Anal. Biochem. 102:206–212), as described (Reczkowski et al., 1994, Arch. Biochem. Biophys. 312:31–37). In initial experiments, $IC_{50}$ values for ABHA and N-hydroxyarginine ($K_i$=42 micromolar; Daghigh et al., 1994, Biochem. Biophys. Res. Commun. 202:174–180) were compared. Assays were performed in 100 millimolar CHES, pH 9.0, containing 1 millimolar arginine.

2(S)-N-(tert-butyloxycarbonyl)-glutamic acid tert-butyl ester (compound 1 in FIG. 6) was obtained from Sigma Chemical Company (St. Louis, Mo.). Triethylamine and DMSO (dimethyl sulfoxide) were obtained from Fisher Scientific (Malvern, Pa.). All other reagents were obtained from Aldrich Chemical Co. (St. Louis, Mo.).

Figure 6:
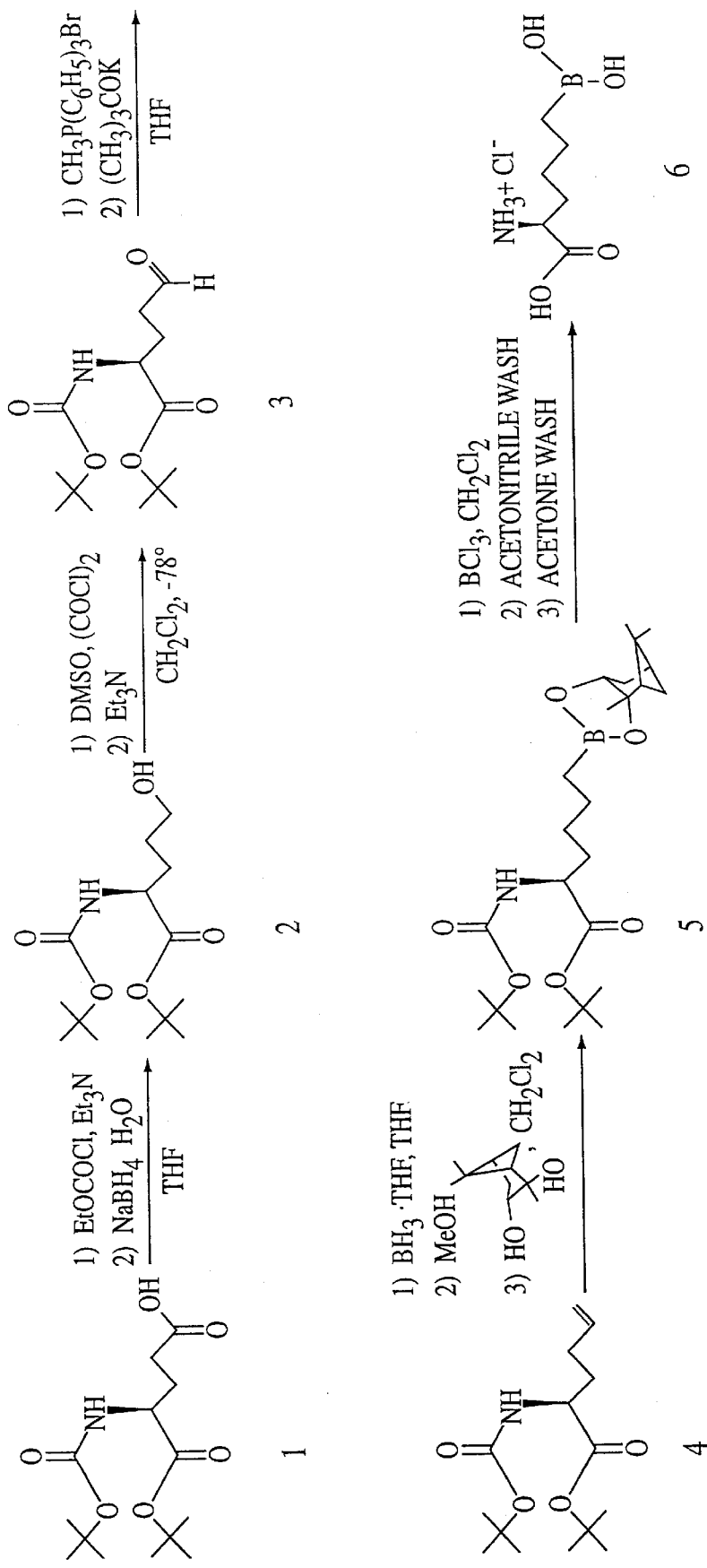
FIG. 6 is an image which illustrates the synthetic scheme described herein for the production of ABHA.

The chemical synthetic scheme used to make ABHA is illustrated in FIG. 6.

Synthesis of 2(S)-N-(tert-butyloxycarbonyl)-5-hydroxypentanoic acid, tert-butyl ester (Compound 2 in FIG. 6)

To a solution of 2.339 grams (7.71 millimoles) 2(S)-N-(tert-butyloxycarbonyl)-glutamic acid tert-butyl ester in 70 milliliters of tetrahydrofuran (THF) maintained at −5° C. was added 7.80 milliliters (77.1 millimoles) triethylamine and 7.37 milliliters (77.1 millimoles) ethyl chloroformate. The mixture was maintained at −5° C. for ten minutes with stirring. The precipitant triethylamine salt was quickly removed by filtration. The filtrate was added to a suspension of sodium borohydride in 10 milliliters of water and stirred at room temperature overnight. The resulting crude product was purified by column chromatography on silica gel, using 2:1 hexane:ethyl acetate as an eluent, to yield 2(S)-N-(tert-butyloxycarbonyl)-5-hydroxypentanoic acid, tert-butyl ester ("Compound 2").

Synthesis of Compound 3 in FIG. 6

Compound 3 was made by Swern oxidation of Compound 2, as described (Nancuso et al., 1978, J. Org. Chem. 43:2480–2482), and was used directly without purification.

Synthesis of Compound 4 in FIG. 6

Compound 4 was made by subjecting crude Compound 3 to a Wittig reaction as described (Bowden, 1975, Synthesis 784) using triphenylphosphonium methylide. Compound 3, 1.151 grams (4.01 millimoles), was dissolved in THF and was added directly to the triphenylphosphonium methylide solution. The Wittig reaction was stirred and allowed to proceed for fifteen minutes at −78° C. and then overnight at room temperature. Compound 4 was purified by separating the Wittig reaction products using a silica gel column using 10:1 hexane:ethyl acetate as an eluent, and then repeating the separation to improve purity. Following concentration in vacuo, 450 milligrams (22% over two steps) of product as a colorless oil was obtained. TLC using 3:1 hexane:ethyl acetate as the mobile phase indicated a single spot at $R_f$=0.60. Compound 4 had the following properties: $^1$H-NMR ($CDCl_3$) δ 5.80 (m, 1H), 5.00 (m, 3H), 4.15 (m, 1H), 2.05 (m, 2H), 1.85 (m, 1H), 1.65 (m, 1H), 1.45 (s, 9H), 1.40 (s, 9H).

Synthesis of 2(S)-N-(tert-butyloxycarbonyl)-6-[(1S,2S,3R,5S)-(+)-pinanedioxaboranyl]-hexanoic acid, tert-butyl ester (Compound 5 in FIG. 6)

To a stirred solution of 6.05 milliliters (6.05 millimoles) of 1 molar $BH_3$. THF in 60 milliliters THF at 0° C. was added 345 milligrams (1.21 millimoles) of Compound 4. The reaction mixture was stirred for two hours at room temperature and monitored for the disappearance of Compound 4 by performing TLC, using 3:1 hexane:ethyl acetate as the mobile phase. Excess non-reacted borane was quenched by slow addition of methanol until gas evolution, as indicated by bubbling, ceased. The solvent was evaporated in vacuo. The crude material was taken up in $CH_2Cl_2$. Excess (1S,2S,3R,5S)-(+)-pinanediol (1 gram, 5.87 millimoles) was added to the solution of crude material in $CH_2Cl_2$. Esterification with (+)-pinanediol was allowed to proceed at room temperature for two hours. Compound 5 was purified by column chromatography using silica gel, using 25:1 hexane:ethyl acetate as an eluent. Compound 5 was obtained as an oil in 31% yield (174 milligrams) following concentration in vacuo. TLC, using 10:1 hexane:ethyl acetate as the mobile phase, indicated a single spot at $R_f$=0.15. Compound 5 had the following properties $^1$H-NMR ($CDCl_3$) δ 4.95 (d, 1H), 4.20 (d, 1H), 4.1 (m, 1H), 2.40–2.15 (m, 2H), 2.05 (m, 1H), 1.95–1.65 (m, 411), 1.60 (s, 3H), 1.42 (2s, 18H), 1.35 (apparent s, 4H), 1.25 (s, 3H), 1.05 (d, 1H), 0.80 (m, 5H). The molecular mass calculated for $C_{25}H_{44}NO_6B$+H is 466.33. The molecular mass of Compound 5 observed using ZAB-E CI+/MS mass spectrometry was 466.25.

Synthesis of 2(S)-amino-6-boronohexanoic Acid, Hydrochloride Salt (ABHA; Compound 6 in FIG. 6)

To a stirred solution of 174 milligrams of Compound 5 in $CH_2Cl_2$ at −78° C. was slowly added 1.49 milliliters of 1 molar $BCl_3$ (1.49 millimoles) in $CH_2Cl_2$. The reaction mixture was stirred for fifteen minutes at −78° C. and then for thirty minutes at 0° C. The solvent $CH_2Cl_2$ and excess $BCl_3$ were evaporated by passing a flow of nitrogen gas over the mixture. Continued drying with $N_2$ gas afforded crude product as an orange solid. Addition of acetonitrile removed most of the color from the crude product. Vacuum filtration followed by several washings with acetonitrile yielded a pale pink-colored solid which, upon air-drying, had a faint discoloration. Acetone was added to the pale pink-colored solid. Vacuum filtration followed by several washings with acetone removed all discoloration from the solid to yield 33 milligrams (42% yield) of pure ABHA as a white solid. TLC, using 80:10:10 n-butanol:acetic acid:water as the mobile phase, indicated a single spot at $R_f$=0.15. ABHA had a melting point between 148 and 150° C., dec.>130°, and the following properties: $^1$H-NMR (CD$_3$OD) δ 3.95 (t, 1H), 1.90 (m, 2H), 1.45 (m, 4H), 0.82 (m, 2H); $^{11}$B NMR (CD$_3$OD) δ 18.86 (s).

Crystallization and X-ray Crystal Structure Determination of ABHA

In a 3.7 milliliter screw-cap glass vial, 11 milligrams of ABHA were dissolved in 0.200 milliliters of ethanol. The screw-cap on the glass vial was not tightened, in order to allow slow evaporation of ethanol. The vial was placed in a fume hood for two days. Upon inspection, all solvent had evaporated and ABHA had crystallized as needles and plates. A section of one of the plates proved suitable for crystallographic studies. Larger crystals were grown by slow evaporation of 11 milligrams ABHA dissolved in 0.200 milliliters of water over a period of five days.

ABHA, which has the molecular formula $C_6H_{15}BNO_4Cl$, crystallizes in the orthorhombic space group $P2_12_12_1$ (systematic absences h00: 1=odd; 0k0: k=odd; 001: 1=odd), with a=9.914(2) angstroms, b=20.213(2) angstroms, c=5.1801(6) angstroms, V=1038.0(2) angstroms$^3$, Z=4 and $d_{calc}$=1.353 grams per cubic centimeter. X-ray intensity data were collected using a Rigaku R-AXIS IIc area detector employing graphite-monochromated Mo-K$_\alpha$ radiation (λ=0.71069 angstrom) at a temperature of 295°K. Indexing was performed from a series of 1° oscillation images, with exposures of thirty minutes per frame. A hemisphere of data was collected using 8° oscillation angles, with exposures of sixty minutes per frame and a crystal-to-detector distance of 82 millimeters. Oscillation images were processed, using the bioteX program, to produce a listing of non-averaged F$^2$ and σ(F$^2$) values which were provided to a Silicon Graphics Indigo R4000 computer for further processing and structure solution, using the teXsan program. A total of 4539 reflections were measured over the ranges: 5.76 ≤2θ≤50.70°, −10≤h≤11, −21≤k≤24, −6≤l≤6, yielding 1838 unique reflections ($R_{int}$=0.0590). The intensity data were corrected for Lorentz and polarization effects, but not for absorption.

The structure was solved by direct methods, using the SIR92 program. Refinement was by fall matrix least squares, based on F$^2$ using the SHELXL-93 program. All reflections were used during refinement. Values of F$^2$ that were experimentally negative were replaced by F$^2$=0. The weighting scheme used was w=1/[σ$^2$(F$_o^2$)+0.0537P$^2$+2.4010P], where P=(F$_o^2$+2F$_c^2$) 3. Non-hydrogen atoms were refined anisotropically, and hydrogen atoms were refined according to a "riding" model in which the positions of the hydrogen atoms are re-idealized before each least squares cycle by applying the coordinate shifts of the atom to which each hydrogen is attached. Refinement converged to $R_1$=0.0768 and w$R_2$=0.1627 for 1580 reflections for which F>4σ(F) and $R_1$=0.0905, w$R_2$=0.1756 and GOF=1.106 for all 1838 unique, non-zero reflections and 122 variables. The maximum Δ/σ in the final cycle of least squares was 0.002 and the two most prominent peaks in the final difference Fourier were +0.351 and −0.514 e/Å$^3$.

Crystal Stricture of the Arginine-Ornithine-Borate Complex

Crystals of rat liver arginase were prepared as described (Kanyo et al., 1992, J. Mol., Biol. 224:1175–1177) and transferred to a buffer solution comprising 10 millimolar ornithine and 10 millimolar sodium borate. X-ray diffraction data at 3.0 angstroms resolution were collected and processed as described above. 28,047 total reflections, and 13,114 unique reflections (9–3 angstroms) were used in refinement, which was 74% complete, with $R_{merge}$=0.062.

The atomic coordinates of native rat liver arginase, as described herein in Example 1, served as the starting model for refinement of the structure of the arginase-ornithine-borate complex using the X-PLOR program (Brunger et al., 1987, Science 235:458–460). Refinement of the structure of the complex converged smoothly to a final crystallographic R factor of 0.190 for 9–3 angstrom data ($R_{free}$=0.301), with root-mean-square deviations from ideal bond lengths and angles of 0.013 angstrom and 1.6°, respectively.

Other methods which were used but not described herein are well known and within the competence of one of ordinary skill in the art of chemical synthesis and molecular biology.

The results obtained in the experiments presented in this Example are now described.

Figure 7:
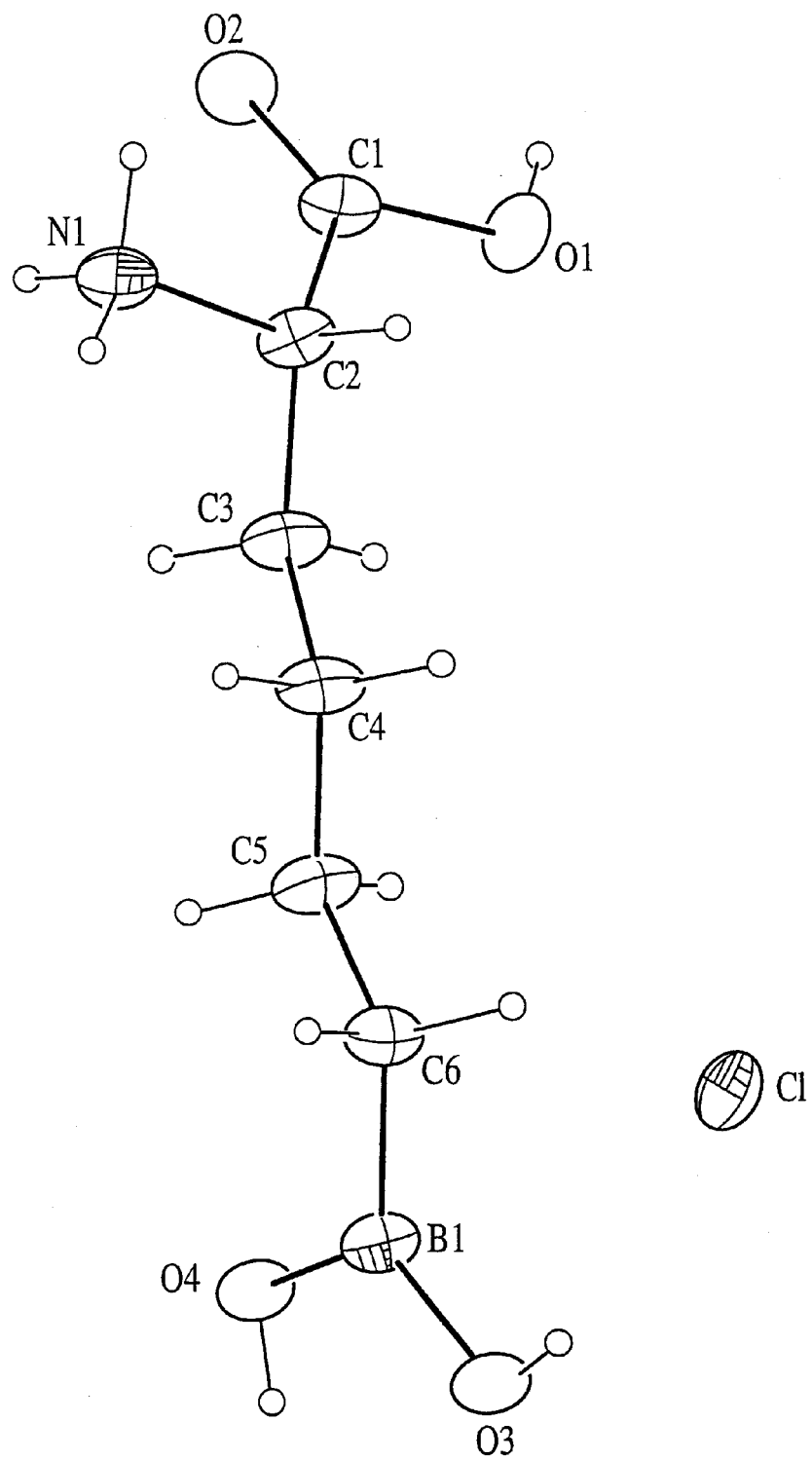
FIG. 7 is an image which depicts an ORTEP representation of the molecular structure of ABHA, using 30% probability thermal ellipsoids.

Table 2 lists cell information, data collection parameters, and refinement data used to determine the structure of ABHA. Final positional and equivalent isotropic thermal parameters are given in Table 3. Anisotropic thermal parameters are in Table 4. Tables 5 and 6 list bond distances and bond angles. A representation of the molecular structure of ABHA, made using the ORTEP program, is depicted in FIG. 7.

TABLE 2

Summary of Structure Determination of ABHA

| | | |
|---|---|---|
| Formula: | | $C_6H_{15}BNO_4Cl$ |
| Formula weight: | | 211.45 |
| Crystal class: | | Orthorhombic |
| Space group: | | $P2_12_12_1$ (#19) |
| z | | 4 |
| Cell constants: | a, Å | 9.914(2) |
| | b, Å | 20.213(2) |
| | c, Å | 5.1801(6) |
| | V, Å$^3$ | 1038.0(2) |
| μ, centimeters$^{-1}$ | | 3.52 |
| crystal size, millimeters | | 0.15 × 0.05 × 0.005 |
| $D_{calc}$, grams per cubic centimeter | | 1.353 |
| F(000) | | 448 |
| Radiation: | | Mo-K$_\alpha$ (λ = 0.71069 Å) |
| 2θ range | | 5.76–50.70° |
| hkl collected: | | −10 ≤ h ≤ 11; −21 ≤ k ≤ 24; −6 ≤ l ≤ 6 |
| No. reflections measured: | | 4539 |
| No. unique reflections: | | 1838 ($R_{int}$ = 0.0590) |
| No. observed reflections | | 1580 (F > 4σ) |
| No. reflections used in refinement | | 1838 |
| No. parameters | | 122 |
| R indices (F > 4σ) | | $R_1$ = 0.0768   w$R_2$ = 0.1627 |
| R indices (all data) | | $R_1$ = 0.0905   w$R_2$ = 0.1756 |
| GOF | | 1.106 |
| Final Difference Peaks, e/Å$^3$ | | +0.351, −0.514 |

TABLE 3

Refined Positional Parameters for ABHA

| Atom | x | y | z | Ueq, Å$^2$ |
|---|---|---|---|---|
| C1 | 0.5824(2) | 0.58210(8) | 0.7367(3) | 0.0481(4) |
| O1 | 0.5795(5) | 0.8844(2) | 0.4197(8) | 0.0503(11) |
| H1 | 0.614(3) | 0.898(3) | 0.286(8) | 0.075 |
| O2 | 0.4088(5) | 0.9503(2) | 0.2973(7) | 0.0462(11) |
| O3 | 0.3464(5) | 0.5523(2) | 1.3516(8) | 0.0451(11) |

TABLE 3-continued

Refined Positional Parameters for ABHA

| Atom | x | y | z | Ueq, Å$^2$ |
|---|---|---|---|---|
| H3 | 0.394(6) | 0.5711(6) | 1.457(8) | 0.068 |
| O4 | 0.2110(5) | 0.5741(2) | 0.9914(8) | 0.0428(10) |
| H4 | 0.206(6) | 0.5337(4) | 1.002(9) | 0.064 |
| N1 | 0.2768(5) | 0.9342(2) | 0.7515(9) | 0.0377(11) |
| H1a | 0.238(3) | 0.923(2) | 0.900(5) | 0.056 |
| H1b | 0.218(2) | 0.929(2) | 0.623(5) | 0.056 |
| H1c | 0.3019(8) | 0.9765(3) | 0.759(9) | 0.056 |
| C1 | 0.4592(6) | 0.9135(3) | 0.4522(10) | 0.0351(13) |
| C2 | 0.3974(6) | 0.8919(2) | 0.7051(10) | 0.0336(13) |
| H2 | 0.4628(6) | 0.8988(2) | 0.8444(10) | 0.045 |
| C3 | 0.3579(7) | 0.8183(2) | 0.6964(10) | 0.043(7) |
| H3a | 0.2711(7) | 0.8142(2) | 0.6113(10) | 0.057 |
| H3b | 0.4237(7) | 0.7946(2) | 0.5930(10) | 0.057 |
| C4 | 0.3491(8) | 0.7856(3) | 0.9608(11) | 0.043(2) |
| H4a | 0.2794(8) | 0.8072(3) | 1.0617(11) | 0.058 |
| H4b | 0.4342(8) | 0.7912(3) | 1.0506(11) | 0.058 |

TABLE 4

Refined Thermal Parameters (U's) for ABHA

| Atom | U$_{11}$ | U$_{22}$ | U$_{33}$ | U$_{23}$ | U$_{13}$ | U$_{12}$ |
|---|---|---|---|---|---|---|
| C1 | 0.0505(9) | 0.0562(8) | 0.0377(7) | −0.0026(8) | −0.0056(8) | 0.0058(7) |
| O1 | 0.044(3) | 0.062(3) | 0.044(3) | 0.013(2) | 0.013(2) | 0.015(2) |
| O2 | 0.053(3) | 0.048(2) | 0.037(2) | 0.010(2) | 0.007(2) | 0.002(2) |
| O3 | 0.053(3) | 0.035(2) | 0.047(3) | 0.008(2) | −0.013(2) | −0.003(2) |
| O4 | 0.055(3) | 0.033(2) | 0.041(2) | −0.001(2) | −0.012(2) | −0.003(2) |
| N1 | 0.044(3) | 0.037(2) | 0.032(2) | 0.003(2) | 0.006(2) | −0.003(2) |
| C1 | 0.046(3) | 0.033(3) | 0.027(3) | 0.000(3) | 0.003(2) | −0.005(3) |
| C2 | 0.044(3) | 0.032(2) | 0.025(3) | 0.000(2) | 0.004(3) | 0.004(2) |
| C3 | 0.070(4) | 0.028(3) | 0.030(3) | 0.004(2) | 0.004(3) | −0.003(3) |
| C4 | 0.072(4) | 0.027(3) | 0.032(3) | 0.004(2) | 0.001(3) | −0.002(3) |
| C5 | 0.074(5) | 0.034(3) | 0.038(3) | 0.006(3) | −0.007(3) | −0.004(3) |
| C6 | 0.057(4) | 0.033(3) | 0.040(4) | 0.003(3) | −0.004(3) | −0.007(3) |
| B1 | 0.047(4) | 0.029(3) | 0.033(3) | 0.002(3) | −0.003(3) | −0.001(3) |

The form of the anisotropic displacement parameter is:
$\exp[-2\pi^2(a^{*2}U_{11}h^2 + b^{*2}U_{22}k^2 + c^{*2}U_{33}l^2 + 2b^*c^*U_{23}kl + 2a^*c^*U_{13}hl + 2a^*b^*U_{12}hk)]$.

TABLE 5

Bond Distances in ABHA

| Bond | Bond Distance, Å |
|---|---|
| O1-C1 | 1.342(7) |
| O4-B1 | 1.383(8) |
| C2-C3 | 1.539(7) |
| C5-C6 | 1.522(8) |
| O2-C1 | 1.203(6) |
| N1-C2 | 1.491(7) |
| C3-C4 | 1.523(7) |
| C6-B1 | 1.568(8) |
| O3-B1 | 1.363(7) |
| C1-C2 | 1.511(7) |
| C4-C5 | 1.530(7) |

TABLE 6

Bond Angles in ABHA

| Bond Pair | Angle, degrees | Bond Pair | Angle, degrees |
|---|---|---|---|
| O2-C1-O1 | 123.9(5) | C4-C3-C2 | 114.1(5) |
| O2-C1-C2 | 126.1(5) | C3-C4-C5 | 111.7(5) |
| O1-C1-C2 | 110.0(5) | C6-C5-C4 | 114.8(5) |
| N1-C2-C1 | 107.4(4) | C5-C6-B1 | 116.5(5) |
| N1-C2-C3 | 110.8(5) | O3-B1-O4 | 116.9(5) |
| C1-C2-C3 | 111.0(4) | O3-B1-C6 | 123.7(5) |
| O4-B1-C6 | 119.3(5) | | |

Figure 8A:
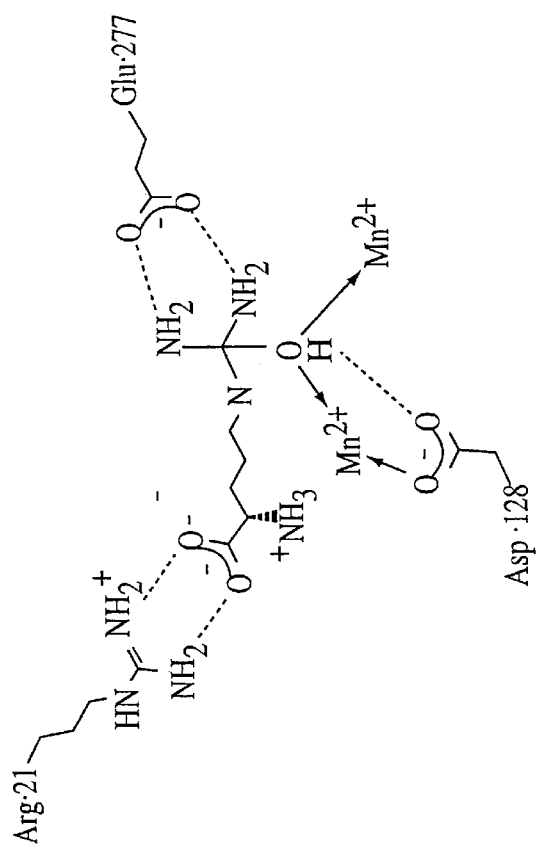

Arginine hydrolysis involves a metal-activated solvent molecule that symmetrically bridges the $Mn^{2+}$—$Mn^{2+}$ ion pair in the native enzyme. The reaction coordinate of hydrolysis is postulated to proceed through a tetrahedral intermediate resulting from nucleophilic attack of the metal-bridging hydroxide ion at the guanidinium carbon of arginine, as depicted in FIG. 8A (Kanyo et al., 1996, Nature 383:554–557).

Ornithine and borate are known to be relatively weak inhibitors of arginase activity. The simultaneous presence of both ornithine and borate inhibits arginase activity more that the presence of either compound alone. In order to understand the mode of inhibition, the X-ray crystal structure of the ternary arginase-ornithine-borate complex was determined. The tetrahedral borate anion mimics binding interactions postulated for the tetrahedral transition states in the physiological arginine-hydrolysis reaction, as depicted in FIG. 8A (Kanyo et al., 1996, Nature 383:554–557). The high affinity of ABHA for arginase apparently results from the structural similarity between the hydrated form of ABHA, as depicted in FIG. 8B, and the proposed tetrahedral intermediate and flanking transition states for arginase-catalyzed arginine hydrolysis, as depicted in FIG. 8A.

Crystal Structure of the Arginase-Ornithine-Borate Complex

Figure 9:
FIG. 9 is an image which depicts an omit electron density map of the arginine-ornithine-borate complex, contoured at 3σ. Refined atomic coordinates are superimposed. One oxygen atom of the tetrahedral borate anion bridges the bi-nuclear manganese cluster. The precise conformation of ornithine (about 5 angstroms away from borate) is ambiguous, due to the low resolution of the electron density map.

The crystal structure of the arginase-ornithine-borate complex revealed net displacement of the manganese-bridging solvent molecule of the native enzyme by an oxygen of the tetrahedral borate anion, as depicted in FIG. 9. No other structural changes are observed in the manganese coordination polyhedra, and the average metal-metal separation distance is 3.5 angstroms, as predicted from EPR studies (Khangulov et al., 1995, Biochemistry 34;2015–2025). The average metal-metal separation is 3.3 angstroms in the native enzyme (Kanyo et al., 1996, Nature 383:554–557).

Although the low resolution of this structure determination precludes a definitive conclusion on the binding conformation of ornithine, an interaction between the alpha-carboxylate group of ornithine and the side chain of Arg-21 is evident in two of the three arginase subunits. The interaction between Arg-21 and the carboxylate group is consistent with the structure-based proposal for arginase-substrate recognition, as described herein in Example 1. Using the crystal structure of the complex determined by this experiment, a structure for a boronic acid-based arginase analog, ABHA, was designed.

Evaluation of the Inhibitory Potential of 2(S)-Amino-6-Boronohexanoic Acid (ABHA)

Boronic acids are effective aminopeptidase and serine protease inhibitors because they presumably bind as tetrahedral transition state analogs (Baker et al., 1980, Fed. Proc., Fed. Am. Soc. Exp. Biol. 39:1686; Matteson et al., 1981, J. Am. Chem. Soc. 103:5241–5242; Baker et al., 1983, Biochemistry 22:2098–2103; Kettner et al., 1984, J. Biol. Chem. 259:15106–15114; Shenvi, 1986, Biochemistry 25:1286–1291). The electron-deficient boron atom of a boronic acid promotes addition to the boron atom of a suitable nucleophile, such as a protein-bound nucleophile or a solvent molecule, yielding a stable anionnic tetrahedral species. Based on the structure of the ternary arginase-ornithine-borate complex described herein, it was postulated that the boronic acid analog of arginine, 2(S)-amino-6-boronohexanoic acid (ABHA), would bind avidly to arginase as the hydrated anion to mimic the tetrahedral intermediate and its flanking transition states (see FIG. 8). ABHA is the first example of a boronic acid-based arginine isostere.

Determination of the crystal structure of ABHA confirmed the presence of the expected trigonal planar geometry of the boronic acid moiety of ABHA.

The tetrahedral borate anion is a modest, noncompetitive inhibitor of arginase, having a $K_i$ value of 1.0 millimolar and a $K_i$ value of 0.26 millimolar. Inhibition of arginase activity by borate is even more pronounced in the presence of ornithine, which is a competitive inhibitor of arginase, having a $K_i$ value of 1.0 millimolar (Pace et al., 1981 Biochem. Biophys. Acta 658:410–412; Reczkowski et al., 1994, Arch. Biochem. Biophys. 312:31–37; Khangulov et al., 1995, Biochemistry 34:2015–2025). Measurement of the inhibitory potential of arginase inhibitors yielded an $IC_{50}$ value of 80 micromolar for N-hydroxyarginine and an $IC_{50}$ value of 0.8 micromolar for ABHA.

A more complete kinetic analysis of inhibition of arginase by ABHA was complicated by non-linearity of kinetic re-plots. The origin of this non-linearity is not clear, since ABHA is a reversible inhibitor that exhibits no evidence of slow-binding behavior. Additional evidence for high affinity binding of arginase and ABHA was derived from competition binding experiments using ABHA and N-hydroxyarginine, as monitored by fluorescence spectroscopy. Addition of N-hydroxyarginine to a solution of arginase results in a significant decrease in intrinsic protein fluorescence at 327 nanometers. Addition of a saturating concentration of ABHA to the arginase-N-hydroxyarginine complex restores the fluorescence of the enzyme to that observed for the enzyme alone. Addition of ABHA alone to arginase does not result in significant changes in protein fluorescence. These experiments indicate that $K_d \leq 0.1$ micromolar for ABHA at pH 7.5 and at pH 9.0.

ABHA is one of the most potent inhibitors of $Mn_2^{2+}$-arginase reported to date. Previously reported inhibitors include various free amino acids (millimolar $K_i$ values), N-hydroxyarginine ($K_i = 42$ micromolar), N-hydroxyindospicine ($K_i = 20$ micromolar), N-hydroxylysine ($K_i = 4$ micromolar), and N-hydroxy-nor-arginine ($K_i = 0.5$ micromolar, Daghigh et al., 1994, Biochem. Biophys. Res. Commun. 202:174–180; Hunter et al., 1946, J. Biol. Chem. 157:427–446; Boucher et al., 1994, Biochem. Biophys. Res. Commun. 203:1614–1621; Custot et al., 1996, J. Biol. Inorg. Chem. 1:73–82; Custot et al., 1997, J. Am. Chem. Soc. 119:4086–4087). It is known that the closer the structural analogy between an inhibitor and the catalytic transition state, the tighter the inhibitor is expected to bind (Pauling, 1946, Chem. Eng. News 24:1375–1377; Wolfenden, 1969, Nature 223:704–705; Wolfenden, 1976, Annu. Rev. Biophys. 5:271–306). It appears that the high affinity of arginase for ABHA arises from the fact that the hydrated form of ABHA is the closest structural analog of the tetrahedral intermediate of the arginase-catalyzed arginine hydrolysis reaction, and its flanking transition states, generated to date.

EXAMPLE 3

Additional Boronic Acid-Based Arginine Analogs Inhibit Arginase with High Affinities and Unusual Binding Kinetics Boronic acid-based and trihydroxysilyl-based transition state analog inhibitors for arginase have been designed, synthesized, and evaluated. Initial characterization of the inhibitory potency of these compounds was achieved using a new chromogenic arginase substrate, 1-nitro-3-guanidinobenzene (compound 18). Surprisingly, only the trihydroxysilyl-based inhibitor, S-(2-trihydroxysilylethyl)-cysteine (compound 16), yielded linear kinetics with a modest $K_i$ of 420 micromolar (assuming competitive inhibition). Due to non-linearity of kinetic re-plots, the two most potent boronic acid-based inhibitors, 2(S)-amino-6-boronohexanoic acid (ABHA; compound 7) and S-(2-boronoethyl)-L-cysteine (compound 15), were further characterized by assay with [$^{14}$C-guanidino]-L-arginine and by the technique of titration calorimetry. The $K_d$ values obtained by titration calorimetry for compounds 7 and 15 were 0.11 micromolar and 2.22 micromolar, respectively.

The enzymes of arginine catabolism have been the subject of increasingly intense research interest. Of particular interest are the critical macrophage enzymes, arginase and nitric oxide (NO) synthase. Arginase catalyzes hydrolysis of L-arginine to form L-ornithine and urea (Christianson, 1997, Prog. Biophys. Molec. Biol. 67:217–252), and NO synthase catalyzes oxidation of L-arginine to form citrulline and NO (Griffith et al., 1995, Annu. Rev. Physiol. 57:707–736). Intriguingly, these two enzymes are reciprocally regulated at the level of transcription (Modolell et al., 1995, Eur. J. Immunol. 25:1101–1104; Wang, et al., 1995, Biochem. Biophys. Res. Commun. 210:1009–1016) and at the level of catalytic activity (Corraliza et al., 1995, Biochem. Biophys. Res. Commun. 206:667–673). $N^\omega$-Hydroxy-L-arginine is an intermediate in the NO synthase reaction (Pufahl et al., 1992, Biochemistry 31:6822–6828; Stuehr et al., 1991, J. Biol. Chem. 266;6259–6263; Klatt et al., 1993, J. Biol. Chem. 268:14781–14787; Campos et al., 1995, J. Biol. Chem. 270:1721–1728; Pufahl et al., Biochemistry 34:1930–1941); significant concentrations of $N^\omega$-hydroxy-L-arginine appear to dissociate from NO synthase to serve as an endogenous competitive inhibitor of arginase with $K_i = 42$ micromolar (Chenais et al., 1993, Biochem. Biophys. Res. Commun. 196:1558–1565; Buga et al., 1996, Amer. J. Physiol. 271:H1988–H1998; Daghigh et al., 1994, Biochem. Biophys. Res. Commun. 202:174–180; Boucher et al., 1994, Biochem. Biophys. Res. Commun.203;1614–16210.

Figure 11B:
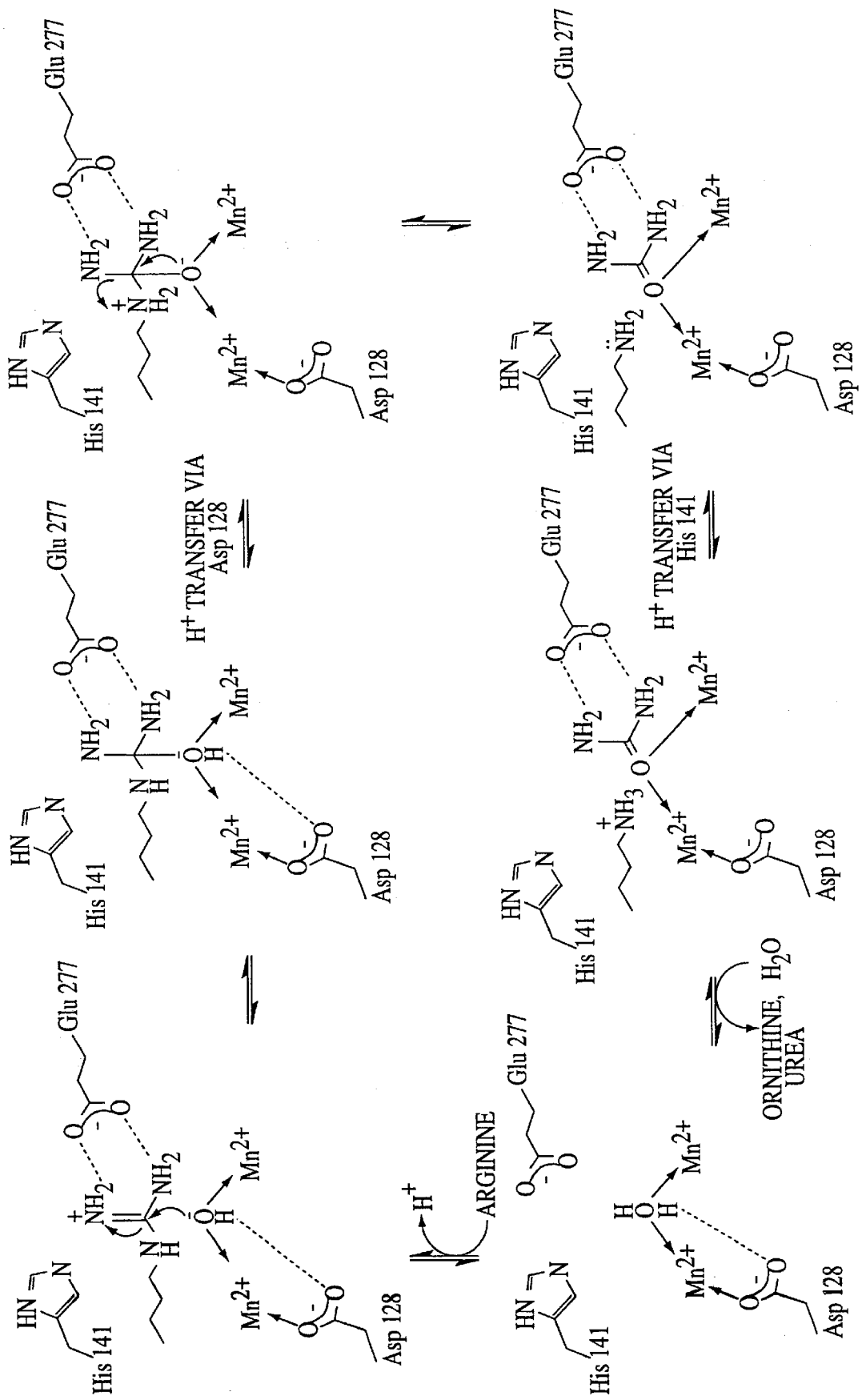
FIG. 11B is a scheme of the arginase mechanism proposed by Kanyo et al. (1996, Nature 383:554–557).
Figure 12B:
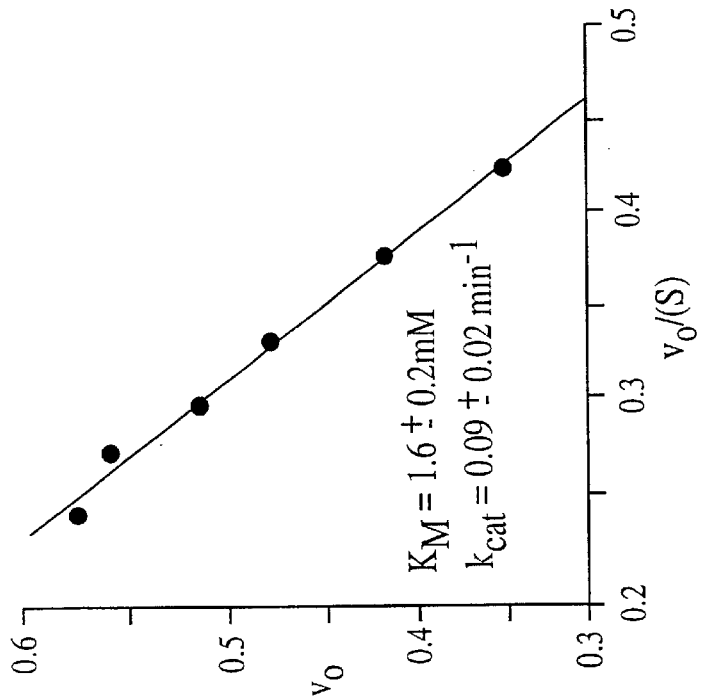
FIG. 12 is a graph depicting the Eadie-Hofstee plot for the new chromogenic substrate, 1-nitro-3-guanidinobenzene (compound 18), where $v_o$ is observed velocity and (S) is substrate concentration.
Figure 12A:
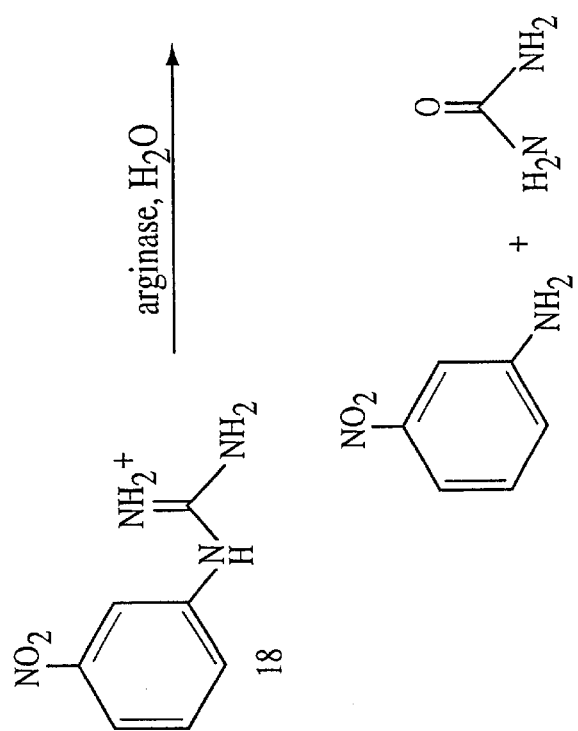

Since arginase can regulate NO synthase activity by depleting cellular concentrations of arginine (Griffith et al., 1995, Annu. Rev. Physiol. 57:707–736), the two enzymes are reciprocally coordinated at the level of enzyme activity (FIG. 11). Selective inhibition of arginase or NO synthase might therefore result in beneficial physiological effects due to the modulation of macrophage function.

In the present Example, various boronic acid-based arginine analogs were tested for their ability to be selective inhibitors of arginase. The bi-nuclear manganese cluster of arginase functions to activate a bridging hydroxide ion for attack at the guanidinium group of the substrate arginine (Reczkowski et al., 1992, J. Am. Chem. Soc. 114:10992–10994; Kanyo et al., 1996, Nature 383:554–557). A key tetrahedral intermediate results (FIG. 11), and boronic acid-based inhibitor ABHA (compound 7) wag designed to mimic this intermediate and its flanking transition states (Example 2). Specifically, the electron-deficient boron atom of the boronic acid moiety is sufficiently electrophilic to facilitate addition of a catalytic nucleophile, such as a protein atom or a solvent molecule. Similar design strategies have resulted in potent boronic acid-based inhibitors of serine proteases (Matteson et al., 1981, J. Am. Chem. Soc. 103:5241–5242; Kettner et al., 1984, J. Biol. Chem. 259: 15106–15114) and aminopeptidases (Shenvi 1986, Biochemistry 25:1286–1291). Accordingly, ABHA (compound 7) is one of the most potent boronic acid-based inhibitors of arginase known to date with $IC_{50}$=0.8 micromolar, yet does not inhibit NO synthase (Example 2).

Surprisingly, ABHA (compound 7) exhibited substantial non-linearity in kinetic re-plots (Example 2), and a full description of its binding kinetics has been reported herein. These unusual binding kinetics can arise from the unique chemistry of the electron-deficient boronic acid moiety. In order to complement this work and further probe the unusual chemistry of boronic acid-based analogs of arginine, we also report the synthesis and kinetic evaluation of 2(S)-amino-5-boronopentanoic acid (compound 12), and the kinetic evaluation of S-(2-boronoethyl)-L-cysteine (compound 15) (the synthesis of compound 15 is previously reported; Matteson et al., 1964, J. Med Chem. 7:640–643). Additionally, the synthesis and kinetic evaluation of a trihydroxysilane-based arginine analog, S-(2-trihydroxysilylethyl)-cysteine (compound 16), as well as a new chromogenic substrate which allows for a continuous assay of arginase activity is reported herein.

The Materials and Methods used in this Example are now described.

General Methods

Thin layer chromatography (TLC) was performed on Merck silica gel 60 $F_{254}$ glass plates. Compounds with tert-butyloxycarbonylamino groups or free amino groups were visualized on TLC plates by first dipping the plates in a ninhydrin solution (0.1% ninhydrin in 95% n-butanol, 4.5% water, 0.5% glacial acetic acid) and then heating the plates until color evolved. Column chromatography was performed on Merck silica gel 60 (230–240 mesh ASTM) under positive nitrogen pressure. $^1$H-NMR and $^{11}$B-NMR spectra were recorded on a Bruker AC-250 (250 megahertz) NMR and on a Bruker AC-200 (200 megahertz) NMR, respectively ($^1$H chemical shifts are referenced to $CHCl_3$, HDO, or DMSO, and $^{11}$B chemical shifts are referenced to $BF_3$ diethyl ether. Electrospray mass spectrometry was conducted by personnel in the Mass Spectrometry Center, University of Pennsylvania.

2(S)-N-(tert-butyloxycarbonyl)-aspartic acid tert-butyl ester (1) was purchased from Bachem. Triethylamine and DMSO (dimethyl sulfoxide) were purchased from Fisher. All other reagents were purchased from Aldrich and used without further purification.

2(S)-amino-6-boronohexanoic acid (ABHA)

The synthesis and preliminary evaluation of this boronic-based analog is described in Example 2.

2(S)-N-(tert-butyloxycarbonyl)-4-hydroxypentanoic acid, tert-butyl ester (compound 8)

To a solution of 2.90 grams (10.0 millimoles) of 2(S)-N-(tert-butyloxycarbonyl)-aspartic acid, tert-butyl ester in 70 milliliters of THF maintained at −5° C. was added 2.79 milliliters (20.0 millimoles) triethylamine and 1.92 milliliters (20.0 millimoles) ethyl chloroformate. The mixture was maintained at −5° C. for five minutes with stirring. The precipitant triethylamine salt was quickly removed by filtration. The filtrate was added to a suspension of sodium borohydride in 5 milliliters of water and stirred at room temperature overnight. The resulting crude product was purified by column chromatography on silica gel (with 5:1 hexane:ethyl acetate as an eluent). Following concentration in vacuo, 1.44 grams of product was obtained (52% yield). TLC (1:1 hexane:ethyl acetate) indicated a single spot ($R_f$=0.41). $^1$H-NMR ($CDCl_3$): δ 1.45 (s, 18H), 2.15 (m, 2H), 3.70 (m, 2H), 4.40 (m, 1H), 5.40 (d, 1H).

2(S)-N-(tert-butyloxycarbonyl)-4-oxobutanoic acid, tert-butyl ester (compound 9)

To a solution of 1.83 milliliters (20.9 millimoles) of oxalyl chloride in 30 milliliters $CH_2Cl_2$ maintained at −78° C. was added 2.97 milliliters (41.9 millimoles) of DMSO. The solution was stirred at −78° C. for 5 minutes. A solution of 1.44 grams (5.24 millimoles) of compound 8 dissolved in 10 milliliters of $CH_2Cl_2$ was prepared, added by cannula to the pre-formed Swem reactant, and stirred at −78° C. for 15 minutes. The Swern oxidation was completed by the addition of 0.726 milliliter (14.6 millimoles) of triethylamine. The mixture was stirred for 5 min. at −78° C. and then warmed to room temperature. The $CH_2Cl_2$ was evaporated in vacuo. The crude material was taken up in THF and the precipitant triethylamine salt was removed by filtration. The material was purified by column chromatography on silica gel (with 6:1 hexane:ethyl acetate as an eluent). The product (980 milligrams) was obtained in 69% yield. TLC (1:1 hexane:ethyl acetate) and staining with ninhydrin indicated a single spot ($R_f$=0.65) following concentration in vacuo. $^1$H-NMR ($CDCl_3$): δ 1.45 (s, 18H), 3.0 (t, 2H), 4.45 (m, 1H), 5.35 (d, 1H), 9.75 (s, 1H).

2(S)-N-(tert-butyloxycarbonyl)-pent-4-enoic acid, tert-butyl ester (compound 10)

The Wittig salt triphenylphosphonium methylide was prepared by the addition of 5.11 grams (14.3 millimoles) of potassium tert-butoxide to a partially dissolved solution of 1.61 grams (14.3 millimoles) methyltriphenylphosphonium bromide in 100 milliliters of THF maintained at 0° C. The mixture was stirred at 0° C. for 10 minutes, and then at room temperature for 90 minutes. The mixture turned yellow and was cooled to −78° C. The aldehyde compound 9, 0.980 gram (3.59 millimoles) dissolved in THF was added directly to the triphenylphosphonium methylide solution. The Wittig reaction was stirred and allowed to proceed for 5 minutes at −78° C. and then overnight at room temperature. The olefin compound 10 was purified by column chromatography on silica gel (with 20: 1 hexane:ethyl acetate as an eluent). Following concentration in vacuo, 632 milligrams of product was obtained (65% yield). TLC (3:1 hexane:ethyl acetate) indicated a single spot ($R_f$=0.56). $^1$H-NMR ($CDCl_3$): δ 1.40 (s, 9H), 1.45 (s, 9H), 2.50 (m, 2H), 4.25 (m, 1H), 5.1 (s, 1H), 5.15 (d, 2H), 5.6–5.8 (m, 1H).

2(S)-N-(tert-butyloxycarbonyl)-5-[(1S,2S,3R,5S)-(+)-pinanedioxaboranyl]-pentanoic acid, tert-butyl ester (compound 11).

To a solution of 11.6 milliliters (11.6 millimoles) of 1 molar $BH_3$.THF in 10 milliliters THF, maintained at 0° C. with stirring, was added 632 milligrams (2.33 millimoles) of olefin compound 10. The reaction mixture was stirred for 15 minutes at 0° C., and then for 2 hours at room temperature. Excess non-reacted borane was quenched by slow addition of methanol until gaseous evolution, as indicated by bubbling, ceased. The solvent was evaporated in vacuo. The crude material was taken up in $CH_2Cl_2$. Excess (1S,2S,3R,5S)-(+)-pinanediol (0.793 g, 4.66 millimoles) was added to the solution of crude material in $CH_2Cl_2$. Esterification with (+)-pinanediol was allowed to proceed overnight at room temperature. Compound 11 was purified by column chromatography on silica gel (with 20:1 hexane:ethyl acetate as an eluent). The product was obtained in 22% yield (226 milligrams) following concentration in vacuo. TLC (3:1 hexane:ethyl acetate) indicated a single spot ($R_f$=0.58). $^1$H-NMR ($CDCl_3$): δ 0.80 (m, 5H), 1.05 (d, 2H), 1.25 (s, 3H), 1.35 (s, 3H), 1.40–1.50 (m, 20H), 1.6–1.95 (m, 3H), 2.05 (t, 1H), 2.10–2.35 (m, 2H), 4.15 (m, 1H), 4.25 (d, 2H).

2(S)-amino-5-boronopentanoic acid, hydrochloride salt (compound 12)

To a solution of 226 milligrams of compound 11 in $CH_2Cl_2$, maintained at −78° C. chilled stirring, was slowly added 2.00 milliliters of 1 molar $BCl_3$ in $CH_2Cl_2$ (2.00 millimoles). The reaction mixture was stirred for 15 minutes at −78° C. and then for 30 minutes at 0° C. The solvent $CH_2Cl_2$ and excess $BCl_3$ were evaporated by allowing a flow of nitrogen gas to pass over the mixture.

The product material wag taken up in acetonitrile and collected by vacuum filtration. Repeated washings with acetonitrile and then with diethyl ether gave a crude hygroscopic solid. The solid was taken up in a minimal volume of ethanol. Precipitation of product was induced by addition of acetone. The highly hygroscopic precipitate was collected and removed from the filter paper by addition of ethanol. The ethanol filtrate was collected. Ethanol was evaporated in vacuo to give 16 milligrams of pure product (16% yield). TLC (80:10:10 n-butanol:acetic acid:water) indicated a single spot ($R_f$=0.096). $^1$H-NMR ($D_2O$): δ 0.85 (t, 2H), 1.55 (m, 2H), 1.95 (t, 2H), 3.95 (t, 1H).

S-(2-boronoethl)-L-cysteine, hydrochloride salt (compound 15)

This compound was synthesized as previously described (Matteson et al., 1964, J. Med Chem. 7;640–643; Matteson, 1960, J. Am. Chem. Soc. 82: 4228–4233). The compound was originally synthesized and tested as a water-soluble candidate for boron neutron-capture therapy (Matteson et al., 1964, J. Med Chem. 7:640–643). TLC (80:10:10 n-butanol:acetic acid:water) of the product indicated a single spot ($R_f$=0.44). $^1$H-NMR ($D_2O$): δ 0.95 (t, 2H), 2.50 (t, 2H), 2.75–3.05 (m, 2H), 3.72 (m, 1H). $^{11}$B NMR ($D_2O$) δ 31.33 (s).

S-(2-trihydroxysilylethy)-L-cysteine (compound 16)

A solution consisting of 3.96 grams (32.6 millimoles) L-cysteine in 50 milliliters water and 5 milliliters (32.6 millimoles) of vinyl trimethoxysilane in 40 milliliters methanol was refluxed at 80° C. under a nitrogen atmosphere. At time intervals of 0, 5, and 6 hours, 32 milligrams aliquots of azobisisobutyronitrile were added to the solution. The solution was refluxed for a total of 8.5 hours at 80° C., then stirred overnight at room temperature. The solvents, water and methanol, were removed in vacuo. The residue was taken up in a minimal volume of water, acidified with 1 milliliter of concentrated HCl, and then suspended in excess acetone. After a precipitate settled, the acidic solvent was decanted and discarded. This wash with acid and acetone was repeated two more times in order to remove all non-reacted starting material. The final precipitate was a crystalline, glass-like solid free of contamination from non-reacted L-cysteine, which was present in the filtrate. The product yield was 12% (1.032 g). $^1$H-NMR ($D_2O$): δ 0.90 (brs, 1H), 2.55 (brs, 2H), 2.95 (brs, 2H), 3.90 (brs, 1H), 5.85 (brs, 3H). Electrospray mass spectroscopy indicated a strong tendency to dimerize via the silanetriol moiety. Calculated $C_5H_{14}NO_5SSi^+$, 228.04; found: 406.9, 428.8, and 444.8.

1-nitro-3-(N,N'-bis(tert-butyloxycarbonyl)guanidino) benzene (compound 17)

To a stirred solution of 238 milligrams (1.72 millimoles) m-nitroaniline and 500 milligrams (1.72 millimoles) 1,3-bis(tert-butoxycarbonyl)-2-methyl-2-thiopseudourea in $CH_2Cl_2$ was added 438 milligrams (2.58 millimoles) of silver nitrate (Bergeron et al., 1987, J. Org. Chem. 52:1700–1703, Natsugari et al., U.S. Pat. No. 4,851,422 Jul. 25, 1989; Morimoto et al., U.S. Pat. No. 4,876,251 Oct. 24, 1989). A white precipitate indicative of silver methylsulfide formed after one hour. The mixture was stirred overnight at room temperature. Compound 17 was purified by column chromatography on silica gel (with 10:1 hexane:ethyl acetate as an eluent). The product was obtained in 67% yield (439 milligrams) following concentration in vacuo. TLC (3:1 hexane:ethyl acetate) indicated a single spot ($R_f$=0.43). $^1$H-NMR ($CDCl_3$): δ 1.50 (s, 9H), 1.60 (s, 9H), 7.50 (t, 1H), 7.95 (d, 1H), 8.05 (d, 1H), 8.5 (s, 1H), 10.6 (s, 1H), 11.6 (s, 1H).

1-nitro-3-guanidinobenzene, hydrochloride salt (compound 18)

To a stirred solution of compound 17 (238 milligrams, 0.492 millimoles) in $CH_2Cl_2$ was added 1.97 milliliters of 1 molar $BCl_3$ (1.97 millimoles) in $CH_2Cl_2$. After 30 minutes, excess $BCl_3$ and $CH_2Cl_2$ were removed by passing a stream of nitrogen gas across the surface of the solution. The resulting material was washed with $CH_2Cl_2$. The product was obtained as a white powder in 62% yield. TLC (4:1:1 n-butanol:acetic acid:water) indicated a single spot that was also UV active ($R_f$=0.47). $^1$H-NMR (DMSO): δ7.6–7.8 (m, 3H), 8.0–8.15 (m, 1H), 10.25 (brs.).

Enzyme Assays

Recombinant rat liver arginase was purified as described previously (Cavalli et al., 1994, Biochemistry 33:10652–10657). Concentrations of enzyme stock solutions were determined from absorbance at 280 nanometers using an extinction coefficient of 1.09 milliliters per milligram per centimeter (Schimke, 1970, Methods Enzymol. 17a:311–317). The activity of wild-type arginase was monitored spectrophotometrically using a Pharmacia Biotech UltroSpec™ 2000. Assays were performed in a solution comprising 100 micromolar $MnCl_2$ and 50 millimolar bicine-NaOH (pH 9.0). The compound 1-guanidino-3-nitrobenzene (i.e. compound 18) proved to be a new substrate for arginase hydrolysis, producing products urea and the chromogen m-nitroaniline. A stock solution of 200 millimolar compound 18 in DMSO was prepared. A period of 15 minutes was allowed to permit compound 18 to equilibrate with bicine buffer prior to assay. Reaction velocities were measured at 372 nanometers, where the liberated product, m-nitroaniline, has an extinction coefficient of $1.28\times10^3$ liters per mole per centimeter. For $K_M$ and $k_{cat}$ determinations, 40 microliters of 0.448 milligram per milliliter arginase was added to a cuvette containing bicine buffer and the appropriate concentration of compound 18

(0.8–2.3 millimolar) to achieve a final volume of 1 milliliter. Eadie-Hofstee plots were used to analyze the data.

Compounds 7, 12, 15, and 16 (FIG. 10, Scheme 1) were assayed using 2 millimolar compound 18 as the assay substrate. The concentrations of compounds 7 and 15 were varied in the range 0.5–9.0 micromolar, those of compounds 12 and 16 were varied in the range 200–1000 micromolar. When activity as a function of enzyme concentration was assayed, the concentration of arginase trimer was varied in the range 1.1–6.4 micromolar. For the boronic acid inhibitors, reciprocal plots of inverse velocity as a function of inhibitor concentration were non-linear. For the trihydroxysilane inhibitor, reciprocal plots of inverse velocity as a function of inhibitor concentration were linear.

Dialysis experiments of arginase with the arginase-compound 7 and arginase-compound 15 complexes were performed in following way. Thirty microliters of arginase at a concentration of 11.2 milligrams per milliliter were pre-incubated for thirty minutes with an appropriate concentration of compound 7 (5 microliters of 100 micromolar stock solution). For compound 15, 300 microliters of arginase at a concentration of 0.938 milligram per milliliter were pre-incubated for thirty minutes with a sufficient concentration of compound 15 (30 microliters of 200 micromolar stock solution) to suppress all detectable enzymatic activity. Pre-incubates were then added to bicine buffer containing 4 millimolar compound 18. The final volume of the assay reaction solution was 1 milliliter.

The inhibition of arginase by compounds 7 and 15 was also evaluated using a modified version of the radioactive assay by Rüegg and Russell (Rüegg et al., 1980, Anal. Biochem. 102:206–212). Assays were performed in 100 micromolar $MnCl_2$, 100 millimolar CHES-NaOH (pH 9.0). The reactions were initiated by addition of 5 microliters of a circa 1 unit per milliliter enzyme solution to 45 microliters of reaction mixture containing CHES buffer, 1.4 millimolar L-arginine, about $5.0 \times 10^4$ counts per minute of L-[guanidino-$^{14}$C]arginine, and variable concentrations of the appropriate inhibitor. After a 5–15 minute reaction time, 200 microliters of a stop solution containing 7 molar urea, 10 millimolar L-arginine, and 0.25 molar acetic acid (H 4.5) was added to the reaction (arginase has essentially no activity under these conditions). [$^{14}$C]-Urea was separated from non-reacted L-[guanidino-$^{14}$C]arginine by treatment with 200 microliters of a 1:1 (vol/vol) slurry of Dowex 50 W-X8 in water, and quantitated by adding 200 microliters of the supernatant from the Dowex treatment to 3 milliliters of Liquiscint™ (National Diagnostics) for liquid scintillation counting in a Beckman LS5000CE counter.

Isothermal Titration Calorimetry

All calorimetry experiments were conducted on a MCS isothermal calorimeter from MicroCal, Inc. (Northampton, Mass.). Arginase was exhaustively dialyzed against a solution comprising 100 micromolar $MnCl_2$ and 50 millimolar bicine-NaOH (pH 8.5). Inhibitor was dissolved at a concentration of 1.5 millimolar in an aliquot of the same solution. Prior to the titration experiment, samples were de-gassed under vacuum for 5 minutes. The sample cell (effective volume 1.366 milliliters) was over-filled with 1.8 milliliters of arginase at a concentration of 0.0358 millimolar and the reference cell was filled with water. The contents of the sample cell were titrated with 30–40 aliquots (2.5 microliters each) of inhibitor (an initial 1 microliters injection was made, but not used in data analysis). After each injection, the heat change was measured and converted to the corresponding enthalpy value. The reaction mixture was continuously stirred at 400 rotations per minute during titration. Control experiments were carried out by titrating the inhibitor into the buffer solution under identical experimental conditions. Data analysis was performed using Origin™ software provided with the instrument. The calorimetric data are presented with the background titrations subtracted from the experimental data. The amount of heat produced per injection was calculated by integration of the area under each peak. The data were fit to the following equation, $$q = V \Delta H [E]_t K[L]/1 + K[L],$$

where q is the heat evolved during the course of the reaction, V is the cell volume, $\Delta H$ is the binding enthalpy per mole of ligand, $[E]_t$ is the total enzyme concentration, K is the binding constant, and [L] is inhibitor concentration (Fisher et al., 1995, Methods Enzymol. 1995 259:194–221; Wiseman et al., 1989, Anal. Biochem. 179:131–137).

The Results of the experiments presented in this Example are now described.

The $K_M$ and $k_{cat}$ values for arginase-catalyzed hydrolysis of the new chromogenic assay substrate, 1-nitro-3-guanidinobenzene (compound 18), were 1.6±0.2 millimolar and 0.09±0.02 reciprocal minutes, respectively (FIG. 2), based on a monomer molecular mass of 35 kilodaltons. Within experimental error, the $K_M$ value for compound 18 was identical to that reported for arginine itself ($K_M$=1.4±0.3 millimolar; Fisher et al., 1995, Methods Enzymol. 259:194–221; Wiseman et al., Anal. Biochem. 179:131–137). The $k_{cat}$ value of compound 18 was five orders of magnitude lower than that reported for arginine ($k_{cat}$=15,000±1200 reciprocal minutes; Cavalli et al., 1994, Biochemistry 33:10652–10657). Despite its low $k_{cat}$ value, substrate 18 provided a continuous chromogenic assay with no apparent background and high precision. Furthermore, the synthesis of compound 18 required only two straight-forward steps, which facilitates the rapid production of large quantities of this compound.

Figure 13B:
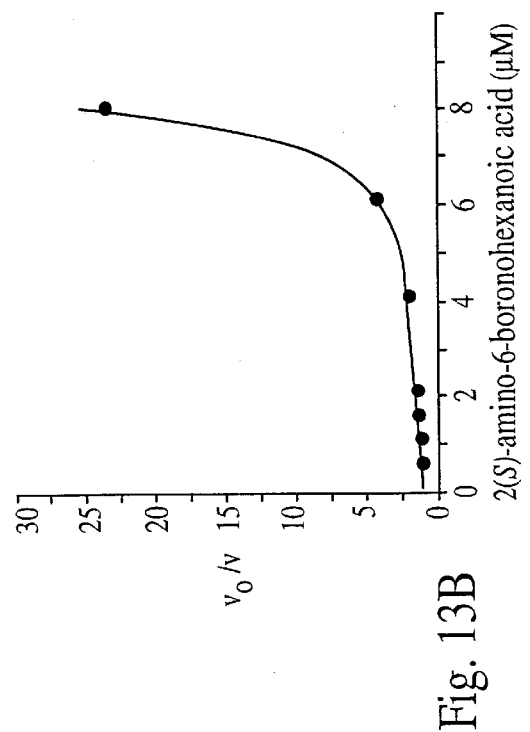
FIGS. 13A, 13B, 13C, and 13D is a quartet of graphs depicting plots of $v_o/v$ as a function of (I) which indicate reversible inhibition only if linear. Only the trihydroxysilane, S-(2-trihydroxysilylethyl)-L-cysteine, yields a linear plot (FIG. 13A). The boronic acid-based arginine analogs 2(S)-amino-6-boronohexanoic acid (FIG. 13B), S-(2-boronoethyl)-L-cysteine (FIG. 13C), and 2(S)-amino-5-boronopentanoic acid (FIG. 13D) did not yield linear plots, indicative of irreversible inhibition. However, dialysis experiments with 2(S)-amino-6-borono-hexanoic acid indicated that it was a reversible inhibitor.
Figure 13D:
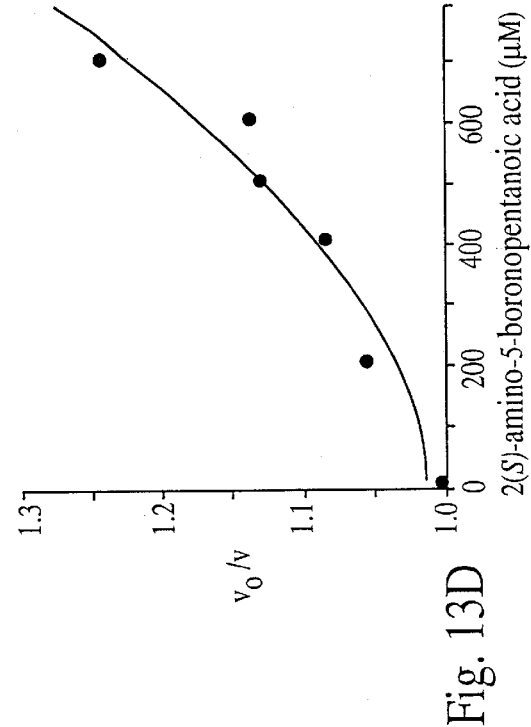
Figure 13A:
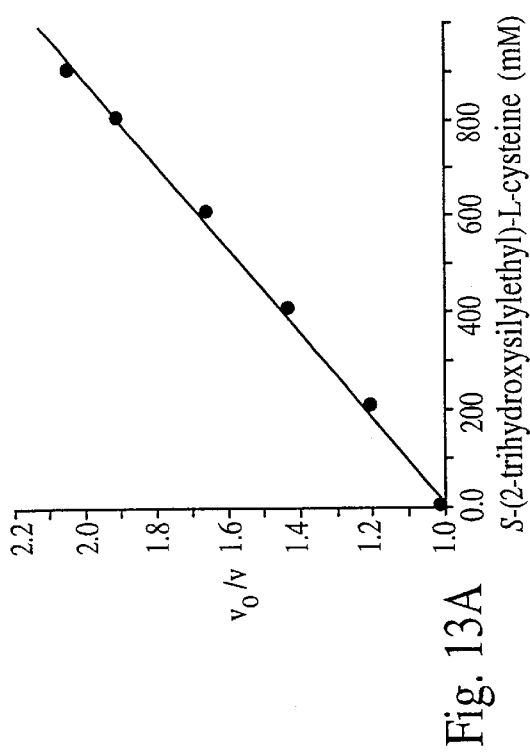
Figure 13C:
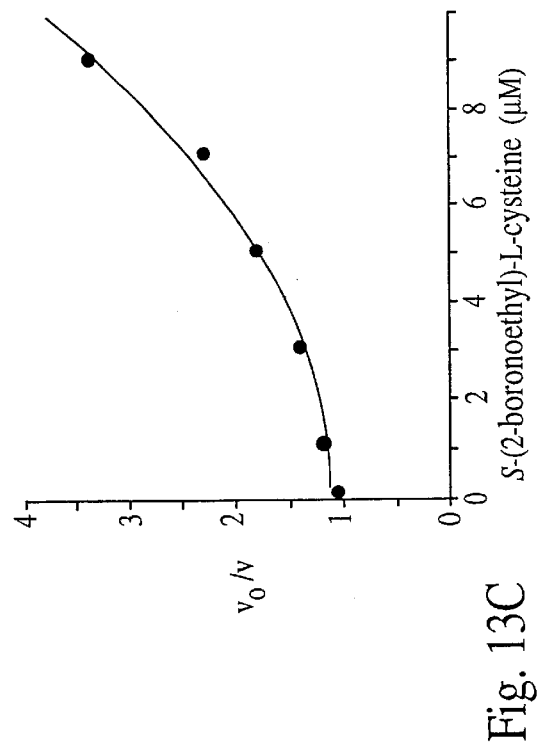

For fully competitive, non-competitive, and uncompetitive inhibitors, plots of $v_o/v$ as a function of (I), should be linear (Todhunter, 1979, Methods Enzymol. 63:383–411; where $v_o$ is enzyme velocity in the absence of inhibitor, v is enzyme velocity in the presence of inhibitor, and (I) is the inhibitor concentration, ($E_o$) is total enzyme concentration). For example, this was the case for the trihydroxysilane inhibitor compound 16, which is a fully reversible inhibitor with a modest $k_i$ of 420±30 micromolar (assuming competitive inhibition; FIG. 13a). However, for boronic acid inhibitor compounds 7, 12, and 15, plots of $v_o/v$ as a function of (I) were non-linear and concave upward (FIGS. 13b–13d).

Figure 14B:
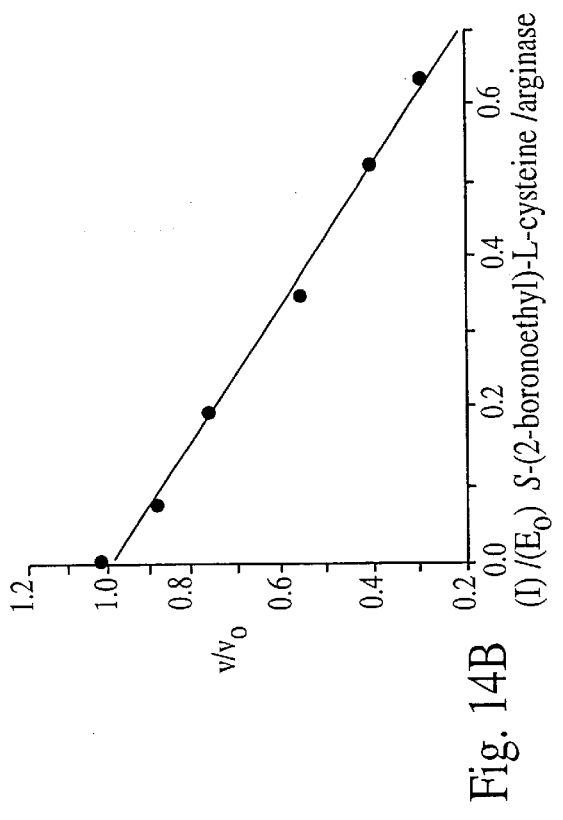
FIGS. 14A, 14B, and 14C is a trio of graphs depicting plots of $v/v_o$ versus $(I)/(E_o)$ for all the boronic acid inhibitors. Plots of $v/v_o$ versus $(I)/(E_o)$ typically are linear for inhibitors that behave as inactivators. Extrapolation of linear $v/v_o$ versus $(I)/(E_o)$ plots to the $(I)/(E_o)$ intercept gives the turnover number for the inactivator. However, the $(I)/(E_o)$ intercept from $v/v_o$ versus $(I)/(E_o)$ plots gave rise to a constant, designated the trivial name pseudo-turnover number, $tn_{pseudo}$. Smaller $tn_{pseudo}$ values indicated better inhibition. Within experimental error, boronic acid inhibitors 2(S)-amino-6-borono-hexanoic acid and S-(2-boronoethyl)-L-cysteine were essentially equipotent (FIG. 14A) and (FIG. 14B), respectively). The $tn_{pseudo}$ for boronic acid 2(S)-amino-5-boronopentanoic acid (FIG. 14C) was two orders of magnitude higher than the $tn_{pseudo}$ values for the other two boronates. The first two boronates were about 400-fold more potent than 2(S)-amino-5-boronopentanoic acid.
Figure 14C:
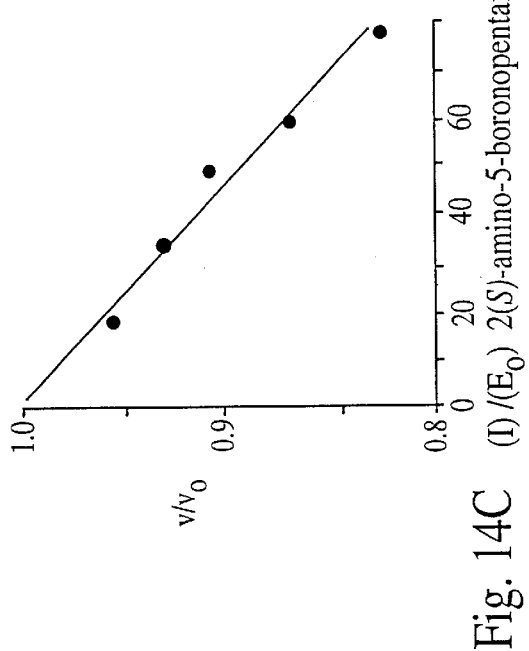
Figure 14A:
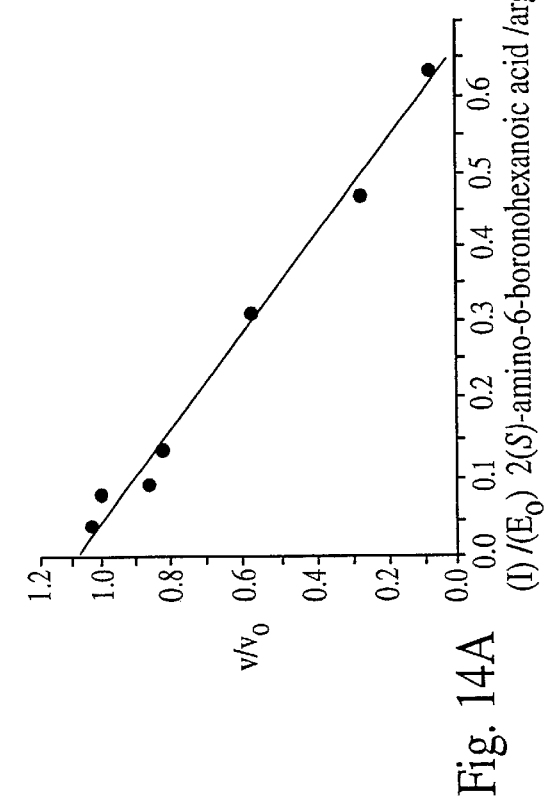

Plots of $v/v_o$ versus (I) at constant ($E_o$) yielded a linear relationship for the boronic acid inhibitors. Likewise, plots of $v/v_o$ as a function of $1/(E_o)$ at constant (I) (4 micromolar ABHA) were linear. These data lead to the observation that $v/v_o$ as a function of $(I)/(E_o)$ was linear for all the boronic acid inhibitors (FIG. 14). Significantly, this relationship was consistent with enzyme inactivation (Silverman, 1988, In: Mechanism-based Enzyme Inactivation: Chemistry and Enzymology, vol. I, CRC Press, Inc., Boca Raton, Fla., pp 22–23). Paradoxically, the boronic acid inhibitors gave no indication of inactivation or time-dependent inhibition, and dialysis experiments indicated complete and virtually instantaneous reversible inhibition when enzyme and inhibitor were incubated for short time periods (30 minutes), in that dialysis experiments with ABHA exhibited completely instantaneous reversible inhibition when arginase and ABHA pre-incubated for 30 minutes were diluted and assayed. Upon dilution, the concentration of ABHA went from 14.3 micromolar to 0.5 micromolar; the concentration of arginase went from 274 micromolar to 9.6 micromolar. The observed inhibited velocity for the diluted and assayed pre-incubate was 0.46 micromolar per minute. A control experiment assaying the activity of arginase at 9.6 micromolar in the presence of 0.5 micromolar ABHA yielded an inhibited velocity of 0.47 micromolar per minute.

For irreversible inhibitors, the slope of linear $v/v_o$ versus $(I)/(E_o)$ plots represented a reciprocal turnover number: moles of enzyme inactivated per moles of inactivator. The reciprocal slopes derived from $v/v_o$ versus $(I)/(E_o)$ plots gave rise to a constant designated the "pseudo-turnover number", $tn_{pseudo}$, since the boronic acids were behaving reversibly and not as inactivators. The $tn_{pseudo}$ provides a useful means for comparing the relative inhibitor potency (Table 7). When assayed with compound 18, boronic acid inhibitors 7 (ABHA) and 15 were essentially equipotent (within experimental error), with compound 7 showing a marginally lower $tn_{pseudo}$. The $tn_{pseudo}$ for boronic acid compound 12 was two orders of magnitude higher than the $tn_{pseudo}$ values for compounds 7 and 15. Thus, inhibitor 12 was about 400-fold less potent than compounds 7 and 15.

TABLE 7

Kinetic and Thermodynamic Data for Boronic Acid Inhibitors

| Inhibitor | $tn_{pseudo}$ (moles of inhibitor/mole of arginase) | $K_i^a$ (micromolar) | $K_d^b$ (micromolar) |
|---|---|---|---|
| 7 | 0.7 ± 0.1 | 0.1 | 0.11 |
| 15 | 1.00 ± 0.004 | 0.7 | 2.22 |
| 12 | 420 ± 30 | N.D. | N.D. |
| 16 | N.A. | 420 | N.D. |

[a]Determined by assay with substrate 18.
[b]Determined by titration calorimetry.

Apparent $K_i$ values for compounds 7 and 15 were obtained using the radioactive [$^{14}$C-guanidino]-L-arginine assay of Rüegg et al. 1980, Anal. Biochem. 102:206–212; Table 7). At low concentrations of compounds 7 and 15, linear plots of $v_o/v$ as a function of (I) yielded $K_i$ values of 0.1 micromolar and 0.7 micromolar for compounds 7 and 15, respectively (assuming competitive inhibition). It appeared that compound 7 was significantly more potent than compound 15 against the natural substrate, L-arginine. Qualitative differences in the results of inhibitor assays using L-arginine or compound 18 as an assay substrate can arise from structural differences between these two substrates: substrate 18 lacks an amino acid moiety and therefore might be legs sensitive to displacement by the amino acid moiety of compounds 7 or 15.

Figure 15:
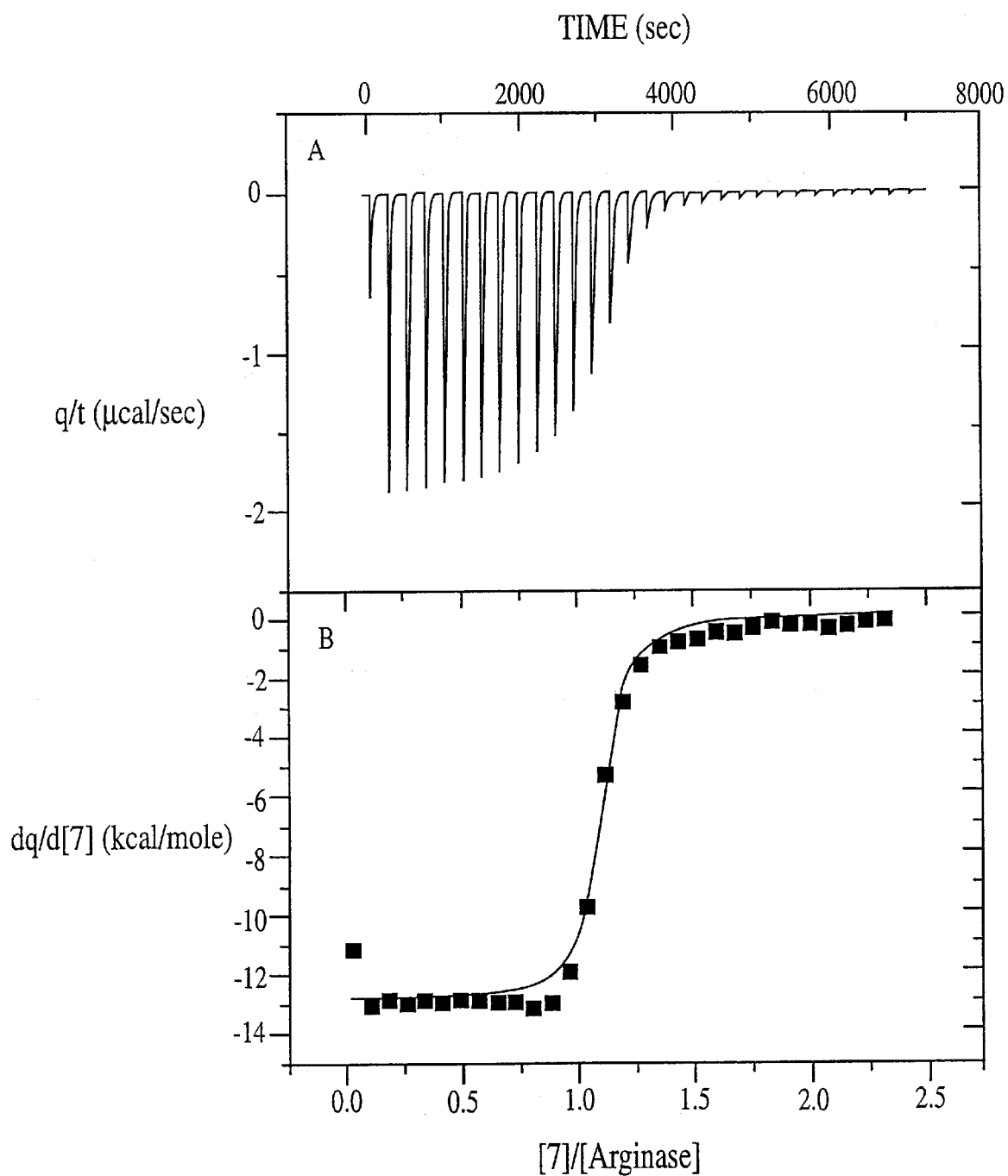
FIG. 15 comprising
Figure 16:
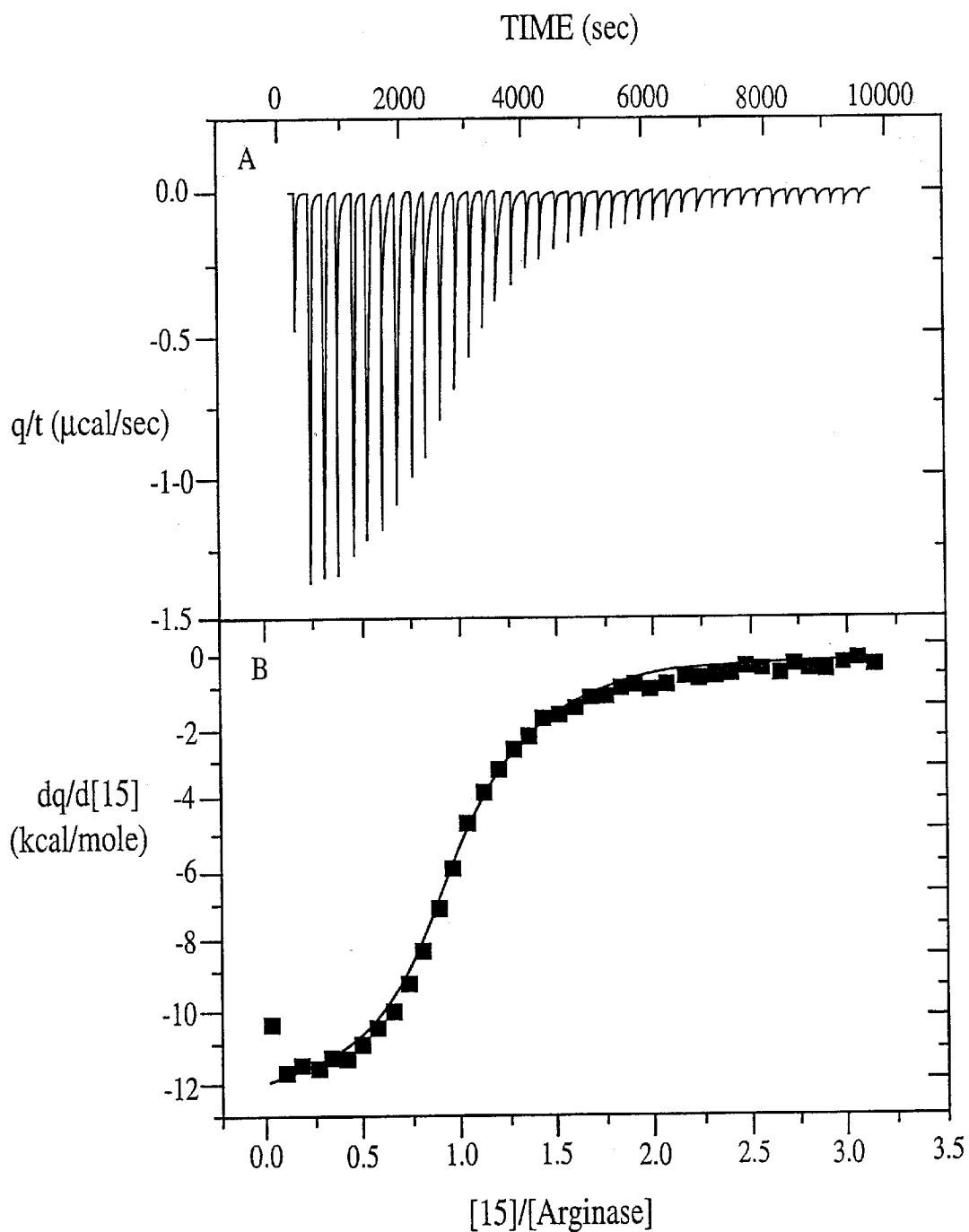
FIG. 16, comprising

The titration calorimetry data for compounds 7 and 15 reveal three important insights on the inhibition of arginase by boronic acids (Table 7; FIGS. 15 and 16). First, $\Delta H_{binding}$ values for compounds 7 and 15 to the arginase monomer were nearly identical (−12.97 kilocalories per mole and −12.75 kilocalories per mole, respectively), suggesting a similar association mechanism. Second, the stoichiometry of inhibitor binding was 1.07 and 0.96 per monomer for compounds 7 and 15, respectively. Finally $K_d$ values ($K_d = 1/K$) of 0.11 micromolar and 2.22 micromolar were obtained for compounds 7 and 15, respectively. Interestingly, the results of kinetic assays agree well with titration calorimetry data for compound 7, with $K_i >> K_d$. However different assays yielded different results for compound 15, i.e., $K_i$ and $K_d$ values disagree by nearly an order of magnitude. Unlike $K_i$, $K_d$ is obtained at thermodynamic equilibrium. Prior to thermodynamic equilibrium, compound 15 may perhaps undergo a conformational change for which $K_i$, a kinetic parameter, is less sensitive.

Figure 17:
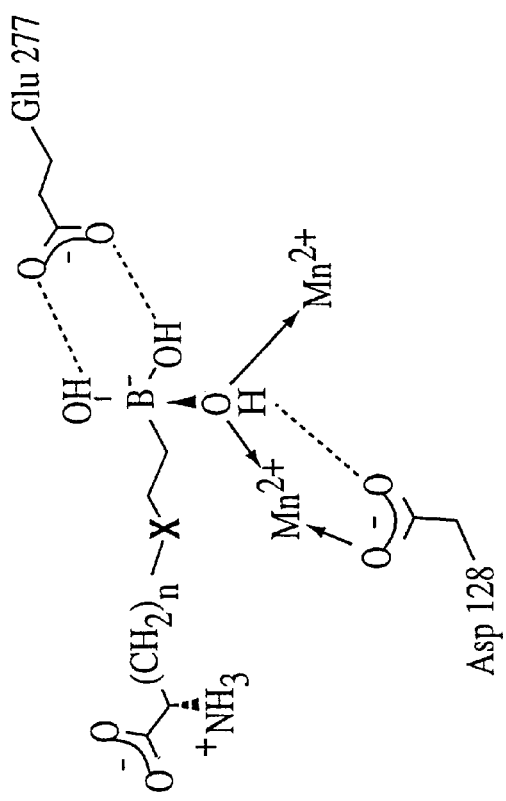
FIG. 17 depicts the proposed binding mode for arginase inhibitors 7, 12, and 15. The metal-bridging hydroxide ion of the native arginase likely attacks the trigonal planar boronic acid to form the tetrahedral boronate anion.

Boronic acid compounds 7, 12, and 15 are expected to bind with arginase as the corresponding tetrahedral boronate anions, thereby mimicking the proposed tetrahedral intermediate and its flanking transition states for arginine hydrolysis (FIG. 17). This type of transition state analog exploits the electron-deficient nature of boron, which facilitates addition of a nucleophilic solvent molecule to generate the boronate anion. In solution, the neutral trigonal planar boronic acid is in a pH dependent equilibrium with the tetrahedral boronate anion. At alkaline pH values (i.e., high (HO$^-$)), the tetrahedral species predominates (Anderson et al., 1964, J. Phys. Chem. 68:1128–1132); this is most likely the case for inhibitors binding with the arginase active site, where the local concentration of metal-bridging hydroxide is high. By way of analogy, the tetrahedral borate anion is a non-competitive inhibitor of arginase which exhibits a $K_{II}$= 0.26 millimolar and a $K_{IS}$=0.98 millimolar, and which binds with the active site by displacing the metal-bridging hydroxide ion (Example 2; Pace et al., 1981, Biochim. Biophys. Acta 658:410–412; Reczkowski, R. S. Ph.D. Thesis, Temple University School of Medicine, 1990). It should be noted that (a) the binding mode of borate, (b) the high affinities of boronic acid-based arginine analogs, and (c) the relative invariance of substrate $K_M$ values with perturbation of the bi-nuclear manganese cluster (Cavalli et al., 1994, Biochemistry 33:10652–10657) do not support a recently proposed arginase catalytic mechanism which involves direct arginine-manganese coordination (Khangulov et al., 1998, Biochemistry 37:8539–8550); instead, these data continue to be consistent with the mechanism proposed by Kanyo et al. (1996, Nature 383:554–557).

In contrast with the boronic acid-based arginine analogs, silanetriol compound 16 has a fixed tetrahedral configuration, and only compound 16 yielded a linear plot of $v_o/v$ versus (I) (indicative of reversible inhibition). However, arginase inhibition by compound 16 is modest: assuming competitive inhibition, $K_i$=420 micromolar. Silanetriol inhibitors have recently been developed against beta-lactamase (Curley et al., 1997, J. Am. Chem. Soc. 119:1529–1538). Here, too, silanetriol are significantly poorer inhibitors than their boronic acid analogs. Silanetriols have additional complications as enzyme inhibitors due to their generally poorer solubility and greater tendency to dimerize (Knight et al.,1989, J. Chem. Soc., Dalton Trans.275–281; McNeil et al., 1980, J. Am. Chem. Soc. 102:1859–1865).

Compounds 7 and 15 are among the most potent arginage inhibitors reported to date, and the use of the new chromogenic substrate 18 facilitates the rapid screening of these inhibitors. Titration calorimetry yields precise $K_d$ values of 0.11 micromolar and 2.22 micromolar for compounds 7 and 15, respectively. The unrivaled potency and selectivity of compound 7 (ABHA) for arginase make this compound ideal for probing the reciprocal functions of arginase and nitric oxide synthase, e.g., in the regulation of nitric oxide-induced smooth muscle relaxation as described in Example 4.

EXAMPLE 4

Biochemical and Functional Profile of Arginase Inhibitors

An increase in arginase activity has been associated with the pathophysiology of a number of conditions including an impairment in non-adrenergic and non-cholinergic (NANC) nerve-mediated relaxation of gastrointestinal smooth muscle. It was hypothesized that an arginase inhibitor may rectify this condition. The effects of a newly designed arginase inhibitor 2(S)-amino-6-boronohexanoic acid (ABHA) with the currently available $N^\omega$-hydroxy-L-arginine (L-HO-Arg) on NANC nerve-mediated internal anal sphincter (IAS) smooth muscle relaxation and the arginase activity in IAS and other tissues was compared in this Example.

Arginase caused attenuation of IAS smooth muscle relaxations by NANC nerve stimulation that was restored by arginase inhibitors. Interestingly, L-HO-Arg, but not ABHA, caused dose-dependent and complete reversal of $N^\omega$-nitro-L-arginine-(L-NNA)-suppressed IAS relaxation that was similar to that seen with L-arginine. Both ABHA and L-HO-Arg augmented NANC nerve-mediated relaxation of the IAS. In IAS, ABHA was about 250 times more potent than L-HO-Arg in inhibiting the arginase activity. L-HO-Arg was 10 to 18 times more potent in inhibiting the arginase activity in the liver, as compared to that in non-hepatic tissues.

It was therefore concluded that arginase has a significant role in regulating of NO synthase-mediated NANC relaxation in the IAS. The advent of new and selective arginase inhibitors therefore has a significant role in discrimination of arginase isozymes and have important pathophysiological and therapeutic implications in gastrointestinal motility disorders.

The purpose of the present investigation was to test a newly designed and selective arginase inhibitor, 2(S)-amino-6-boronohexanoic acid (ABHA; Example 2, compound 7) for its effectiveness in the physiologically relevant system. The effectiveness of ABHA on arginase activity in IAS, rectum, brain, and liver tissues was also examined.

The Materials and Methods used in the experiments presented in this Example are now described.

Functional Studies
Preparation of Smooth Muscle Strips

Studies were performed using circular smooth muscle strips of the internal anal sphincter (IAS) obtained from adult opossums (*Didelphis virginiana*) of either sex following pentobarbital anesthesia (40 milligrams per kilogram intraperitoneally) and subsequent exsanguination. The entire anal canal was isolated carefully by dissection and transferred to a dissecting tray containing oxygenated (95% $O_2$ plus 5% $CO_2$) Krebs' solution. The composition of the Krebs' solution was as follows (in millimolar): NaCl, 118.07; KCl 4.69; $CaCl_2$, 2.52; $MgSO_4$, 1.16; $NaH_2PO_4$, 1.01; $NaHCO_3$, 25 and glucose (Pufahl et al., 1995, Biochemistry 34:1930–1941; Chenais et al., 1993, Biochem. Biophys. Res. Commun. 196:1558–1565). The anal canal was cleaned of extraneous connective tissue and blood vessels. Following this, the anal canal was opened by making an incision along the longitudinal axis, and was pinned flat with the mucosal side facing up. The mucosa and submucosa were removed by sharp dissection. Circular smooth muscle strips were obtained from the whole circumference of the anal canal and divided into two equal strips (about 1×8 millimeters). Both ends of the muscle strips were secured with silk sutures (4–0: Ethicon Inc., Sommerville, N.J.) and used for the measurement of isometric tension.

Measurement of Isometric Tension

IAS smooth muscle strips prepared as described above were mounted onto thermogtatically-controlled 2 milliliter muscle baths (37° C.) containing oxygenated (95% $O_2$ and 5% $CO_2$) Krebs' solution. One end of each muscle strip was fixed to the bottom of the muscle bath with a tissue holder and the other end was attached to an isometric force transducer (model FT03; Grass Instruments Co., Quincy, Mass.) in order to measure isometric tension. Smooth muscle tension was recorded using a Dynograph™ recorder (model R411; Beckman Instruments, Schiller Park, Ill.). After an equilibration period of 1 hour with intermittent washings, the optimal length ($L_0$) and the baseline of the resting tension of each smooth muscle strip were determined as described (Mourami and Rattan, 1988, Am. J. Physiol. 255:G571–G578). Only those smooth muscle strips that developed spontaneous and steady tension and relaxed in response to electrical field stimulation (EFS) were used.

Non-adrenergic Non-cholinergic (ANC) Nerve Stimulation with Electrical Field Stimulation (EFS)

EFS was delivered, via a pair of platinum wires, from a Grass stimulator (Model S88; Grass Instruments Co., Quincy, Mass.) connected in series to a Med-Lab Stimu-Splitter™ II (Med-Lab Instruments, Loveland, Colo.). The Stimusplitter™ was used to amplify and measure stimulus intensity using optimal stimulus parameters for the neural stimulation (12 volt, 0.5 millisecond pulse duration, 200–400 milliamperes, 4 second train) at varying frequencies of 0.5 to 20 Hertz. These parameters of EFS are known to cause relaxation of IAS smooth muscle by selective activation of NANC myenteric neurons. Neurally-mediated relaxation of IAS smooth muscle strips was quantified in response to different frequencies of EFS. All the experiments were performed in the presence of atropine ($1\times10^{-6}$ molar) and guanethidine ($3\times10^{-6}$ molar).

Drug Responses

To determine the influence of arginase on NANC nerve-mediated relaxation of IAS, the effects of different doses of arginase on relaxation were first determined. A dose of 30 units of arginase per milliliter was found to be the most effective in attenuating relaxation. The effectiveness of arginase inhibitors (L-OH-Arg and ABHA) on arginase-induced attenuation of EFS-induced IAS relaxation was then tested. Optimal doses of arginase and L-OH-Arg in IAS have been reported (Chakder and Rattan, 1997, J. Pharmacol. Exp. Ther. 282:378–384). In order to determine the selectivity of arginase inhibitors in IAS, their effects on IAS relaxation suppressed by the NO synthase inhibitor L-NNA ($3\times10^5$ molar) were tested. These results were compared with reversal of relaxation suppression caused by addition of the NO synthase substrate L-arginine at selected concentrations. To examine the physiological relevance of arginase inhibitors in IAS relaxation, the influence of selected concentrating of arginase inhibitorg on EFS-induced IAS relaxation was examined.

At the end of each experiment, smooth muscle strips were treated with 5 millimolar EDTA to establish the maximal relaxation (Biancani et al., 1985, Gastroenterology 89:867–874). Each smooth muscle strip served as its own control.

Tissue Preparation

Tissue samples of the opossum internal anal sphincter muscle (IAS), adjoining rectal tissue, liver, and brain were homogenized using an Ultraturrax™ tissue homogenizer (Tekamr, Cincinnati, Ohio) in a solution comprising 10 millimolar Tris-HCl, 150 millimolar KCl, and 25 millimolar $MnCl_2$, at pH 7.4. The homnogenates were dialyzed overnight against the same solution. Dialyzed homogenates were centrifuged to remove insoluble material and concentrated with Amicon Centricon™ 30 microconcentrators to yield stock protein preparations having protein concentrations of 2.4 milligrams per milliliter for IAS smooth muscle, 3.6 milligrams per milliliter for rectal smooth muscle, 3 milligrams per milliliter for brain, and 17.5 milligrams per milliliter for liver. Protein concentrations were estimated with the Pierce Coomassie Protein Reagent kit using bovine serum albumin as a standard.

Arginase Assay

Arginase activity in tissue homogenates was evaluated using the radioactive L-[guanidino$^{14}$C]arginine assay of Rüegg and Russell (1980, Anal. Biochem. 102:206–212). Assays were performed using a solution comprising 100 millimolar CHES-NaOH and 0.1 millimolar $MnCl_2$ at pH 9.0, The reactions were initiated by addition of 5 microliters of tissue homogenate to 45 microliters of reaction mixture that contained the CHES buffer, the appropriate concentration of arginine (0.5 to 5 millimolar) and about $5.0 \times 10^4$ counts per minute of L-[guanidino-$^{14}$C]arginine. IAS, rectal muscle, and brain homogenates were incubated with the assay mixture at room temperature for one hour, and the liver sample was incubated for 5 minutes. The reactions were stopped by addition of 200 microliters of a stop solution containing 0.25 molar acetic acid, 7 molar urea, and 10 millimolar arginase at pH 4.5. Arginase has essentially no activity at the low pH of the stop solution. [$^{14}$C] Urea was separated from non-reacted L-[guanidino-$^{14}$C]arginine by treatment with 200 µl of 1:1 v/v slurry of Dowex 50W-X8 in water, and quantitated by adding 200 microliters of the supernatant from the Dowex treatment to 3 milliliters of Liquiscint™ (National Diagnostics) for liquid scintillation counting in a Beckman LS 5000CE counter. The data were analyzed using double-reciprocal plots of the initial velocity measurements; standard errors were determined by regression analysis.

Arginase Inhibition Studies

Assays in the presence of the inhibitors $N^\omega$-hydroxy-L-arginine (1 to 100 micromolar) and ABHA (0.05 to 100 micromolar) were performed as described above. The amino acid D-ornithine served as a control in these experiments, since this amino acid, unlike L-ornithine, is not an inhibitor of arginase.

Drugs and Chemicals

Bovine liver arginase, $N^\omega$-hydroxy-L-arginine (L-HO-Arg), $N^\omega$-nitro-L-arginine (L-NNA), $N^\omega$-nitro-D-arginine methyl ester (D-NNA), L-arginine hydrochloride, D-arginine, D-ornithine and atropine sulfate were obtained from Sigma Chemical Co., St. Louis, Mo. Guanethidine monosulfate was from Ciba Pharmaceuticals (Summit, N.J.). Ethylenediamine tetraacetic acid (EDTA) tetrasodium salt was from Fisher Scientific Co., Fair Lawn, N.J. ABHA was synthesized as described in Example 2. L-[guanidino-$^{14}$C]Arginine (specific activity 2.5 GBq per millimole) was from NEN/Dupont.

All chemicals used were of the highest purity available. Solutions of all the chemicals were prepared in Krebs' solution on the day of the corresponding experiment.

Data analysis

The responses to EFS and other relaxants were expressed as a percentage of maximal relaxation caused by 5 millimolar EDTA. The results are expressed as means±standard error. Statistical significance between different groups were determined using t-test and a p value smaller than 0.05 was considered significant.

The Results of the experiments presented in this Example are now described.

Figure 18:
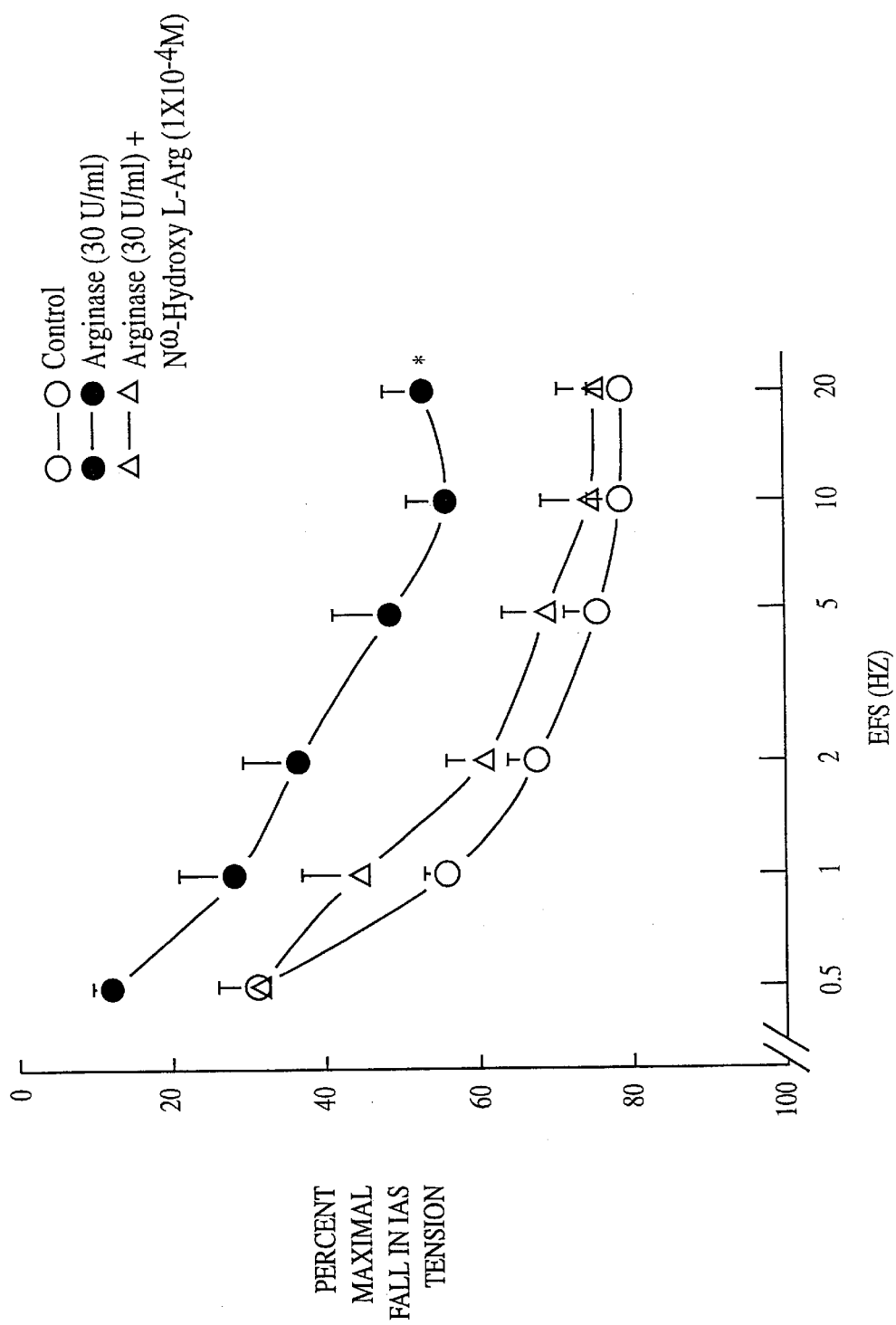
FIG. 18 is a graph depicting the effect of exogenous arginase, before and after application of the arginase inhibitor $N^\omega$-hydroxy-L-Arginine (L-HO-Arg), on the IAS relaxation by different frequencies of electrical field stimulation (EFS). Note the significant suppression of the IAS relaxation by arginase alone and its reversal by L-HO-Arg.

Influence of Exogenous Administration of Arginase Before and After Arginase Inhibitors $N^\omega$-hydroxy-L-arginine (L-HO-Arg) and 2(S)-Amino-6-boronohexanoic Acid (ABHA) on NANC Nerve-mediated Relaxation of IAS First, the effects of selected concentrations of arginase on IAS relaxation by the NANC nerve stimulation were determined. About 30 units per milliliter arginase was found to be optimal for attenuating NANC nerve mediated relaxation of IAS. In the experiments used to examine the influence of L-HO-Arg, IAS relaxations in response to 0.5, 1 and 2 Hertz of EFS in control experiments were 31.0±0.7, 55.9±3.0 and 67.7±3.9%, respectively. Following arginase pre-treatment, IAS relaxation in response to EFS was significantly suppressed and these values in response to 0.5, 1 and 2 Hertz EFS were 12.1±2.5, 28.2±7.3 and 36.6±7.4%, respectively (FIG. 18; p<0.05; n=5). Pre-treatment of tissues with L-HO-Arg ($1 \times 10^{-4}$ molar) before addition of arginase antagonized the effect of arginase in attenuating EFS-induced IAS relaxation.

Figure 19:
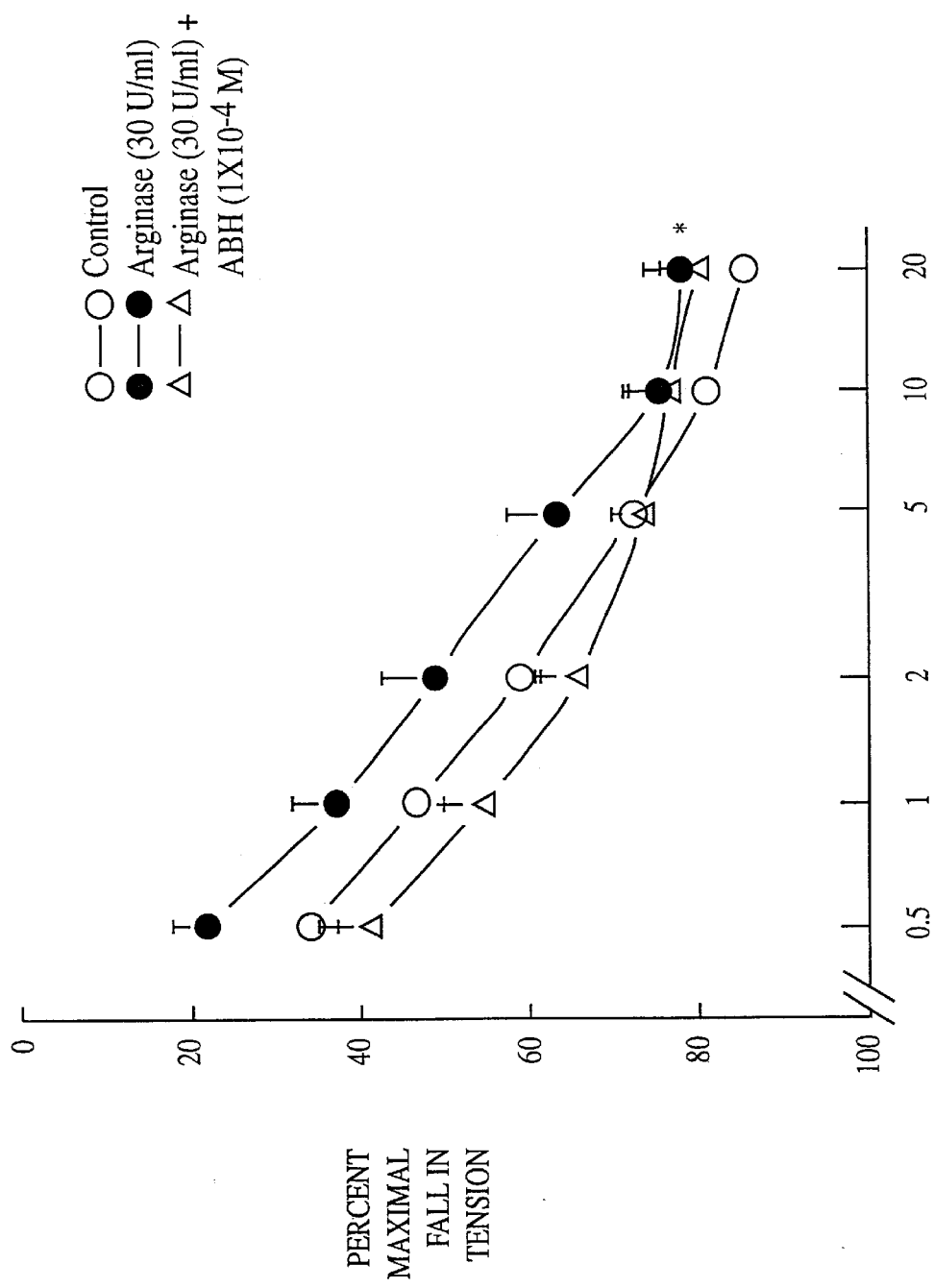
FIG. 19 is a graph depicting the effect of exogenous arginase treatment, before and after application of the arginase inhibitor 2(S)-Amino-6-boronohexanoic Acid (ABHA), on IAS smooth muscle relaxation by different frequencies of EFS. Note the significant suppression of the IAS relaxation by treatment with arginase alone, and its reversal by ABHA.

The effect of ABHA in antagonizing the arginase-suppressed IAS relaxations was similar to that of L-HO-Arg (FIG. 19; p<0.05; n=5).

Figure 20:
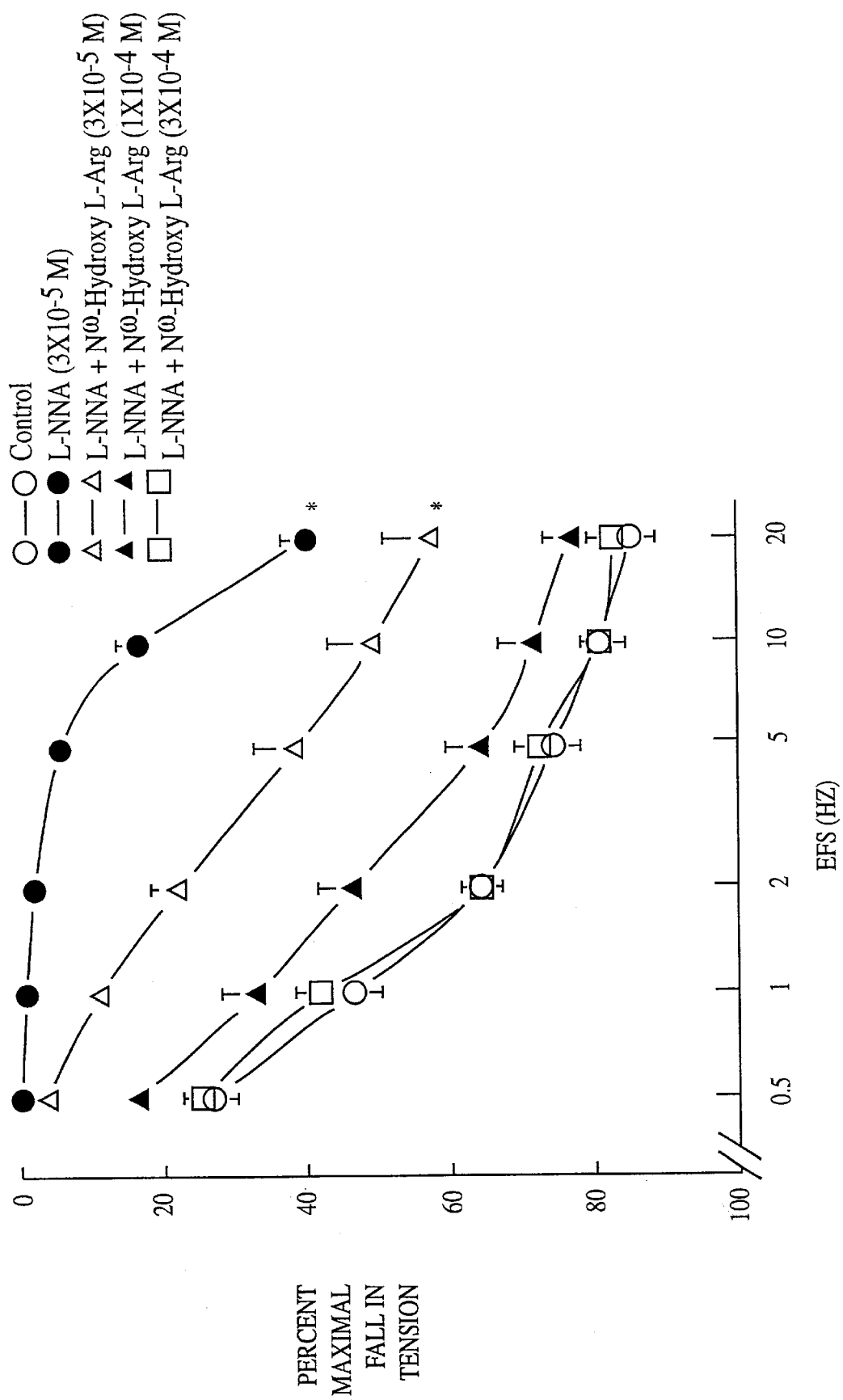
FIG. 20 is a graph depicting the percent maximal decrease in IAS tension by EFS before and after treatment of the tissue with the NO synthase inhibitor L-NNA or L-NNA in combination with selected concentrations of L-HO-Arg. L-NNA caused a marked attenuation of EFS-induced IAS relaxation ($p<0.05$; n=5). L-NNA-attenuated IAS relaxation was reversed by L-HO-Arg in a concentration-dependent manner. L-HO-Arg (3×10$^{-4}$ molar) caused complete reversal of suppressed IAS relaxation.
Figure 21:
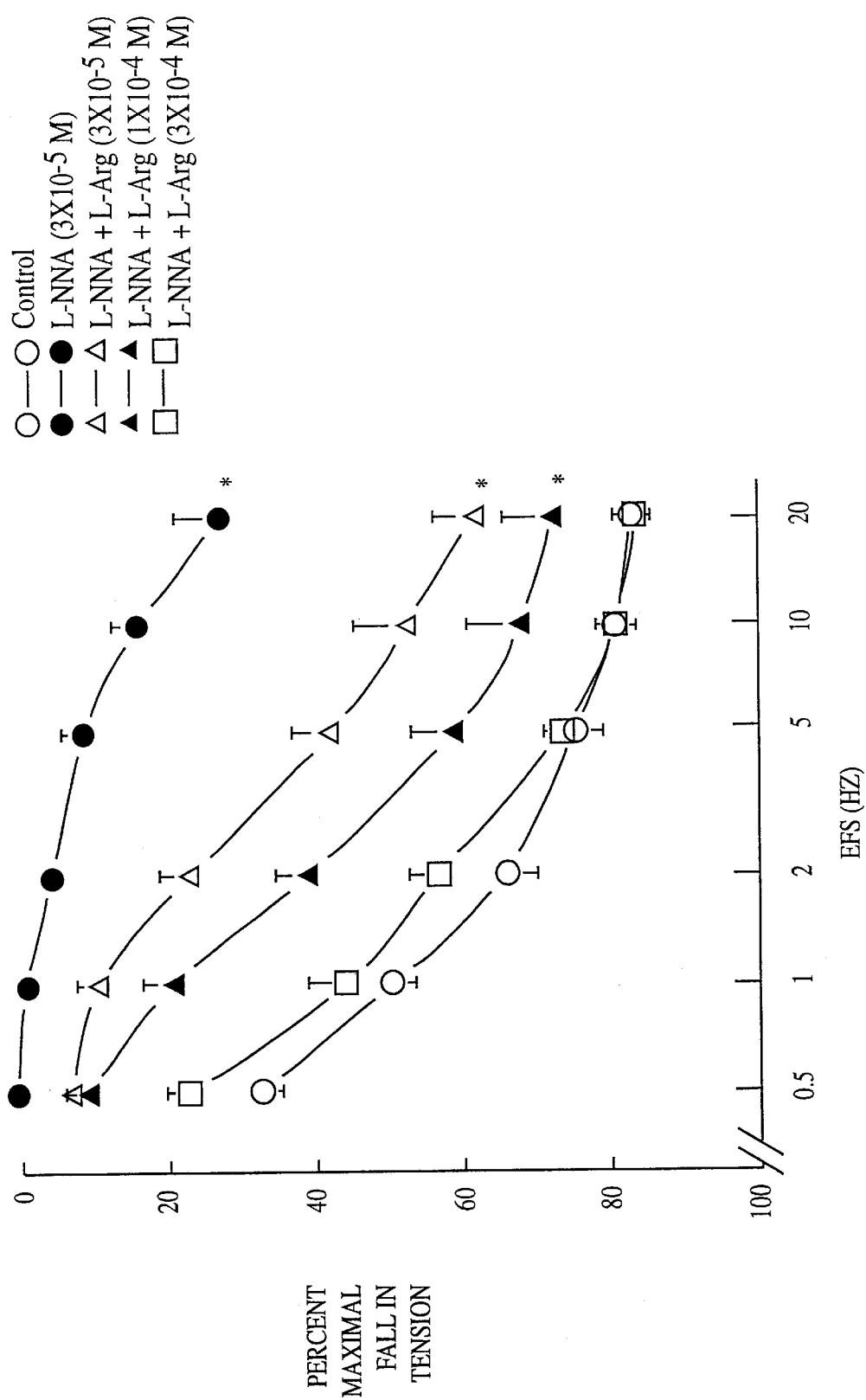
FIG. 21 is a graph depicting the percent maximal decrease in IAS tension produced by EFS, before and after application of the NO synthase inhibitor L-NNA or L-NNA in combination with selected concentrations of L-arginine. Note that L-arginine caused a significant and concentration-dependent reversal of suppressed IAS relaxation and that this effect was somewhat similar to that of L-HO-Arg ($p<0.05$; n=7).

Influence of Arginase Inhibitors on NANC Nerve-Mediated IAS Relaxation in the Presence of the NO synthase Inhibitor L-NNA It is known that the NO synthase inhibitor L-NNA causes a marked suppression of IAS relaxation by NANC nerve stimulation. In order to test the selectivity of the arginase inhibitors in IAS, their effects on IAS relaxation suppressed by the NO synthase inhibitor L-NNA ($3 \times 10^{-6}$ molar) were examined. The results obtained were compared with reversal of the NANC relaxation of IAS caused by the NO synthase substrate L-arginine at selected concentrations. Interestingly, L-NNA-suppressed IAS relaxation was completely reversed by L-HO-Arg (FIG. 20). In control experiments, the decrease in basal IAS tension in response to 0.5, 1, 2 and 5 Hertz EFS was 26.7±3.6, 46.4±4.0, 64.1±3.0 and 74.8±3.9% respectively. L-NNA significant attenuated IAS relaxation to 0±0, 0.6±0.6, 1.8±1.1 and 5.4±2.1%, respectively (p<0.05; n=5). NANC nerve-mediated IAS relaxation in the presence of both L-NNA and L-HO-Arg ($3 \times 10^{-4}$ molar) was indistinguishable from that of control values (p<0.05; n=5). In this regard, L-HO-Arg was nearly as potent as L-arginine in causing the reversal (FIG. 21).

Figure 22:
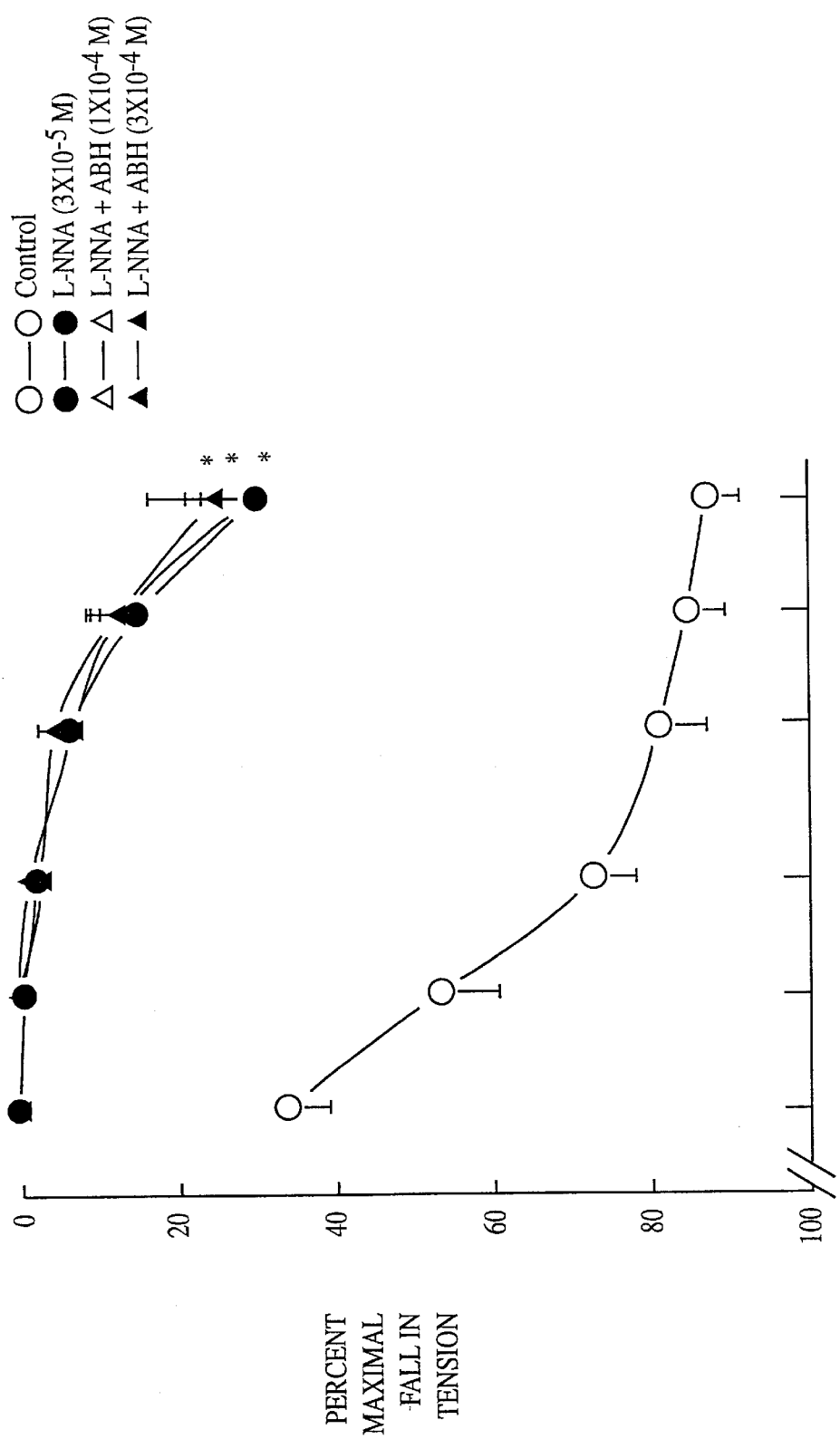
FIG. 22 is a graph depicting the percent maximal decrease in IAS tension produced by EFS before and after application of the NO synthase inhibitor L-NNA or L-NNA in combination with selected concentrations of ABHA. Note that unlike L-HO-Arg, ABHA had no effect on the L-NNA-suppressed IAS relaxation ($p<0.05$; n=4).

Interestingly, and in contrast to L-HO-Arg, the newly synthesized arginase inhibitor ABHA ($3 \times 10^{-4}$ molar) did not cause any reversal of L-NNA-suppressed IAS relaxation (FIG. 22; p<0.05; n=4).

Figure 23:
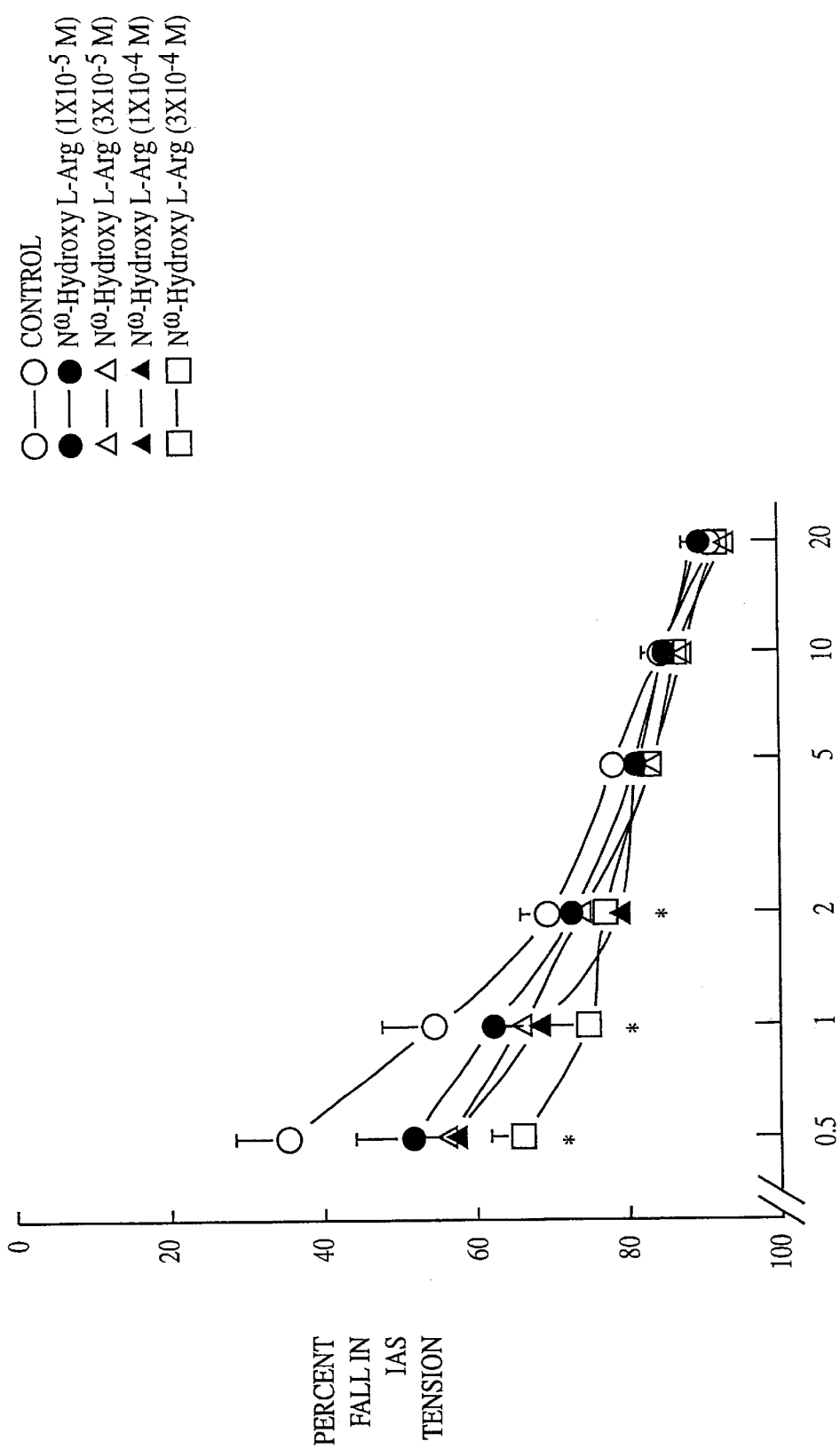
FIG. 23 is a graph depicting the influence of L-HO-Arg on NANC nerve-mediated IAS relaxation produced by EFS. Note that L-HO-Arg caused a significant augmentation of the EFS-induced relaxation of IAS in a concentration-dependent manner and this was evident only in the lower frequencies of EFS ($p<0.05$).
Figure 24:
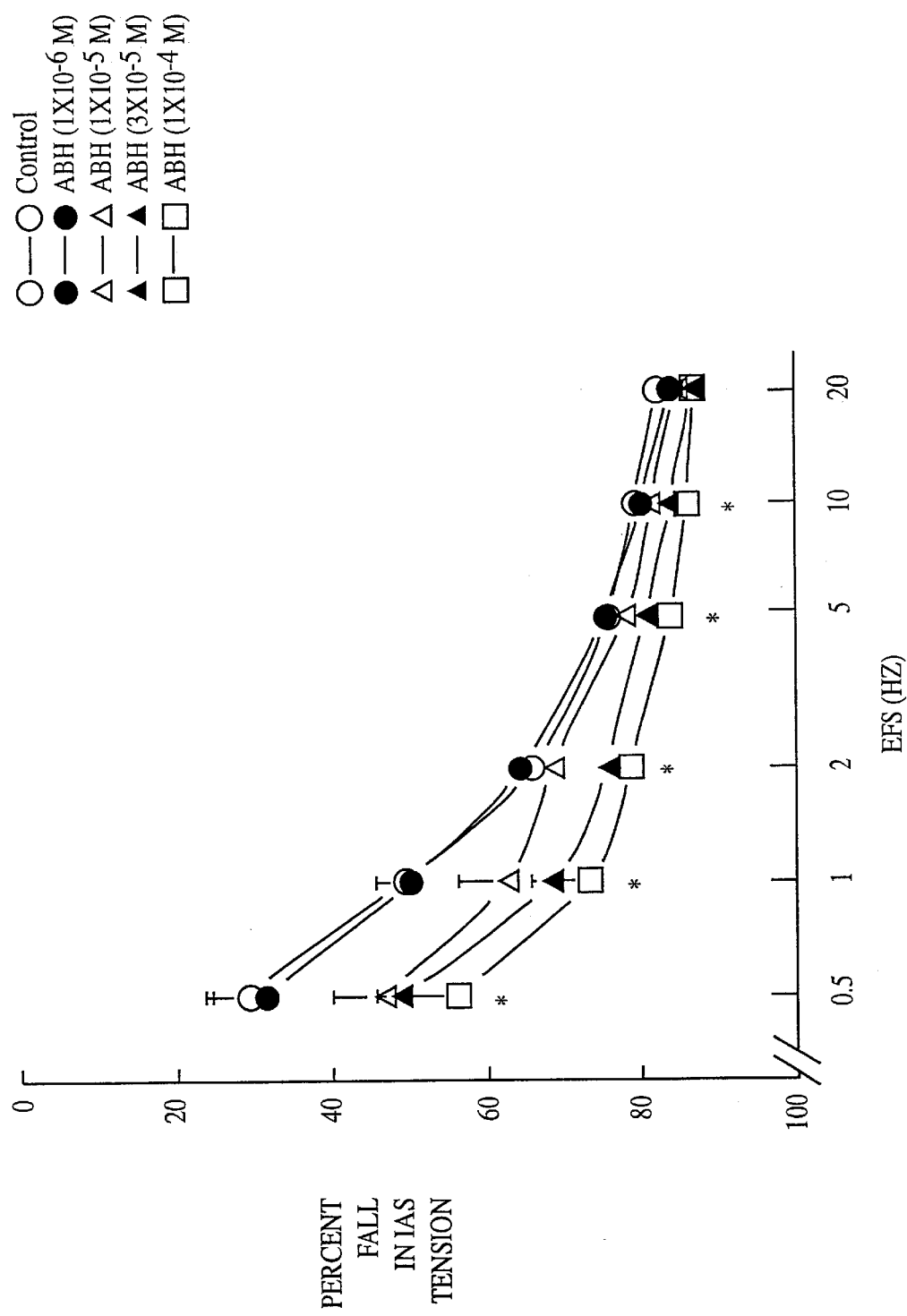
FIG. 24 is a graph depicting the influence of ABHA on NANC nerve-mediated IAS relaxation. Note that ABHA caused a significant augmentation of IAS smooth muscle relaxation caused by the lower frequencies of EFS, in a concentration-dependent manner ($p<0.05$).

Influence of the Arginase Inhibitors on IAS Relaxation caused by NANC Nerve Stimulation In order to determine the physiological significance of arginase in gastrointestinal smooth muscle, the effects of arginase inhibitors on NANC nerve-mediated IAS relaxation were examined. Interestingly, both L-HO-Arg (FIG. 23) and ABHA (FIG. 24) caused significant and concentration-dependent augmentation of NANC nerve-mediated IAS relaxation by EFS. This was particularly evident at lower EFS frequencies. In control experiments for these series of studies, the decrease in IAS tension with 0.5 and 1 Hertz EFS before and after L-HO-Arg ($3 \times 10^{-4}$ molar) was 35.5±7.0 and 54.7±7.0, and 57.4±4.9, 68.8±4.9%, respectively (p<0.05; n=4). Similar data were obtained in experiments involving ABHA: 29.3±5.7, 49.6±3.9 and 56.5±7.0, 73.6±3.5%, respectively of the decrease in basal IAS tension before and after addition of selective arginase inhibitor ($1 \times 10^{-4}$ molar; p<0.05; n=4).

Basal Levels of Arginase Activity in Different Tissues

Figure 25:
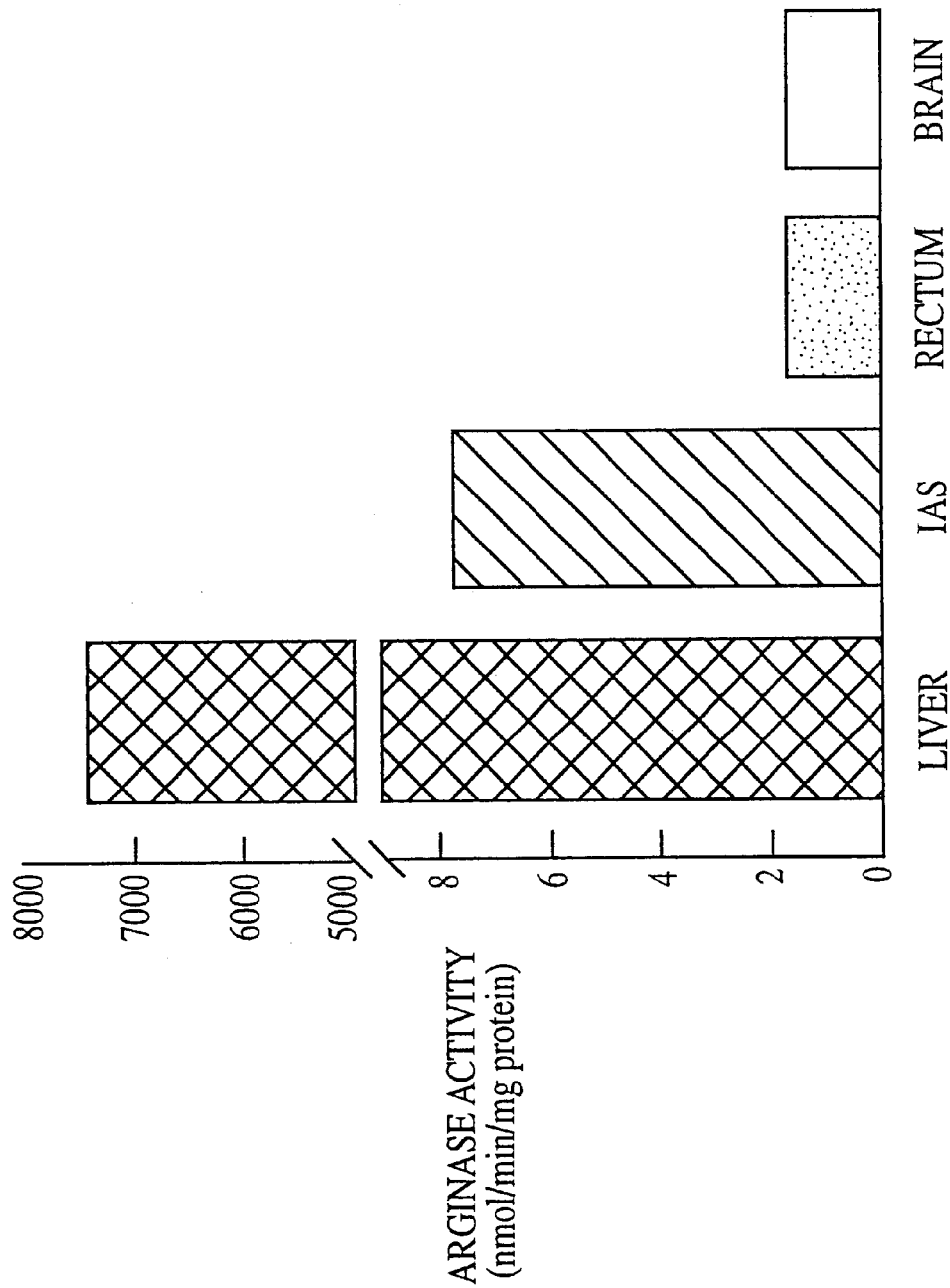
FIG. 25 is a graph depicting basal arginase activity in tissue homogenates of liver, internal anal sphincter (IAS), rectum, and brain. Basal arginase activity for the non-hepatic tissues was found to be about 10$^{-3}$ of that in liver tissue. Interestingly, among the non-hepatic tissues, basal arginase activity in IAS smooth muscle was found to be nearly four-fold higher than in either the adjoining region of the rectum or the brain.

A comparison of basal arginase activity in selected tissues is shown in FIG. 25. Among the tissues examined, liver tissue contained the highest levels of arginase activity (7,400 nanomoles per minute per milligram of protein), consistent with the role of this tissue in nitrogen metabolism and urea synthesis. Among the non-hepatic tissues tested, IAS contained the highest levels of arginase activity (7.8 nanomoles per minute per milligram of protein), while rectum and brain tissues exhibited lower levels (1.7 nanomoles per minute per milligram of protein). $K_m$ values for enzymes obtained from each of these tissues were similar, ranging from 1.0 to 1.9 millimolar. These $K_m$ values are comparable to those for the native and recombinant rat liver enzymes (Cavaili et al., 1994, Biochemistry 33:10652–10657).

Figure 26:
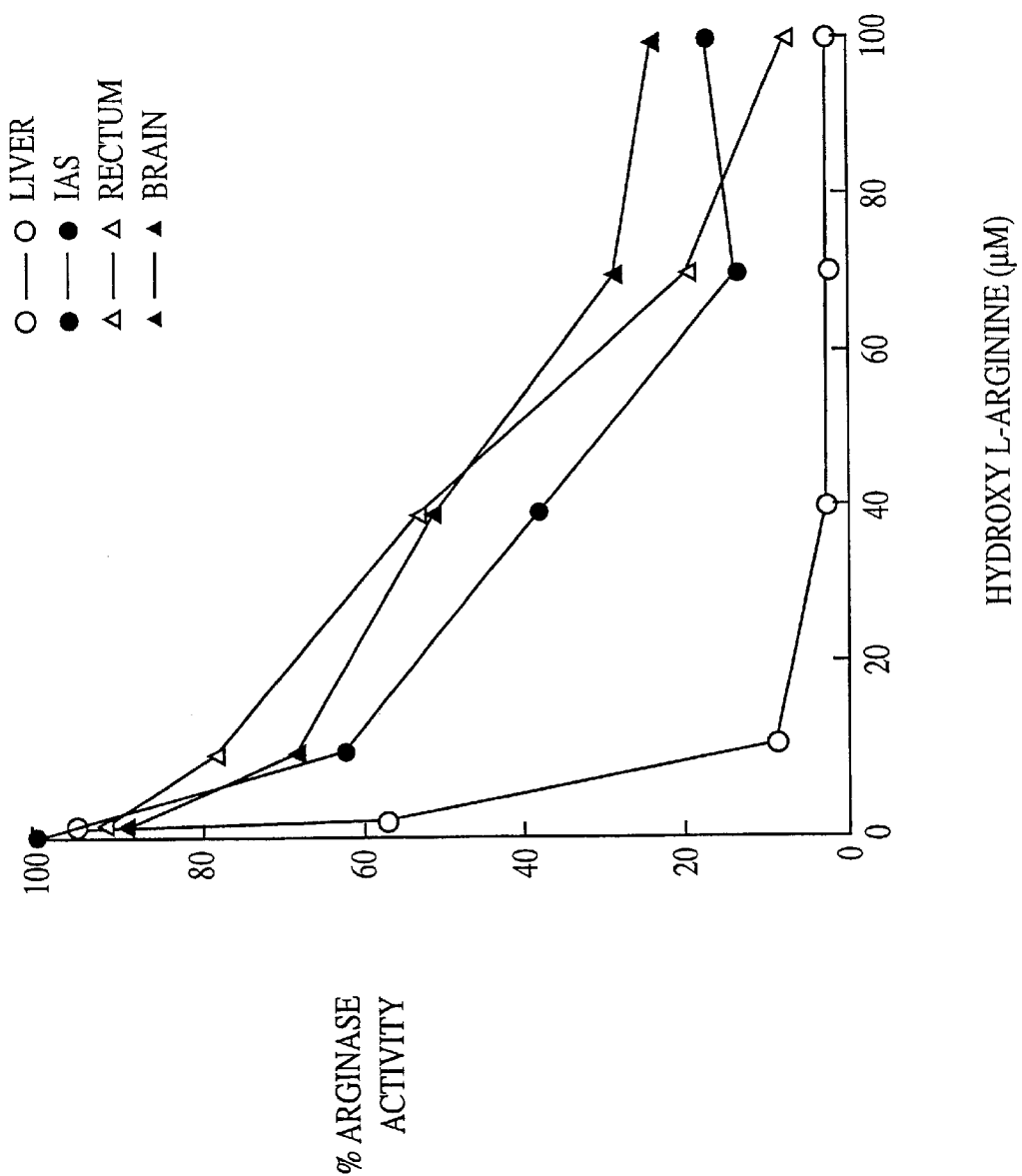
FIG. 26 is a graph depicting the effect of $N^\omega$-hydroxy-L-arginine on arginase activity in hepatic and non-hepatic tissues. $N^\omega$-hydroxy-L-arginine was found to be about 10 times more potent in inhibiting liver arginase activity than arginase activities in non-hepatic tissues.
Figure 27:
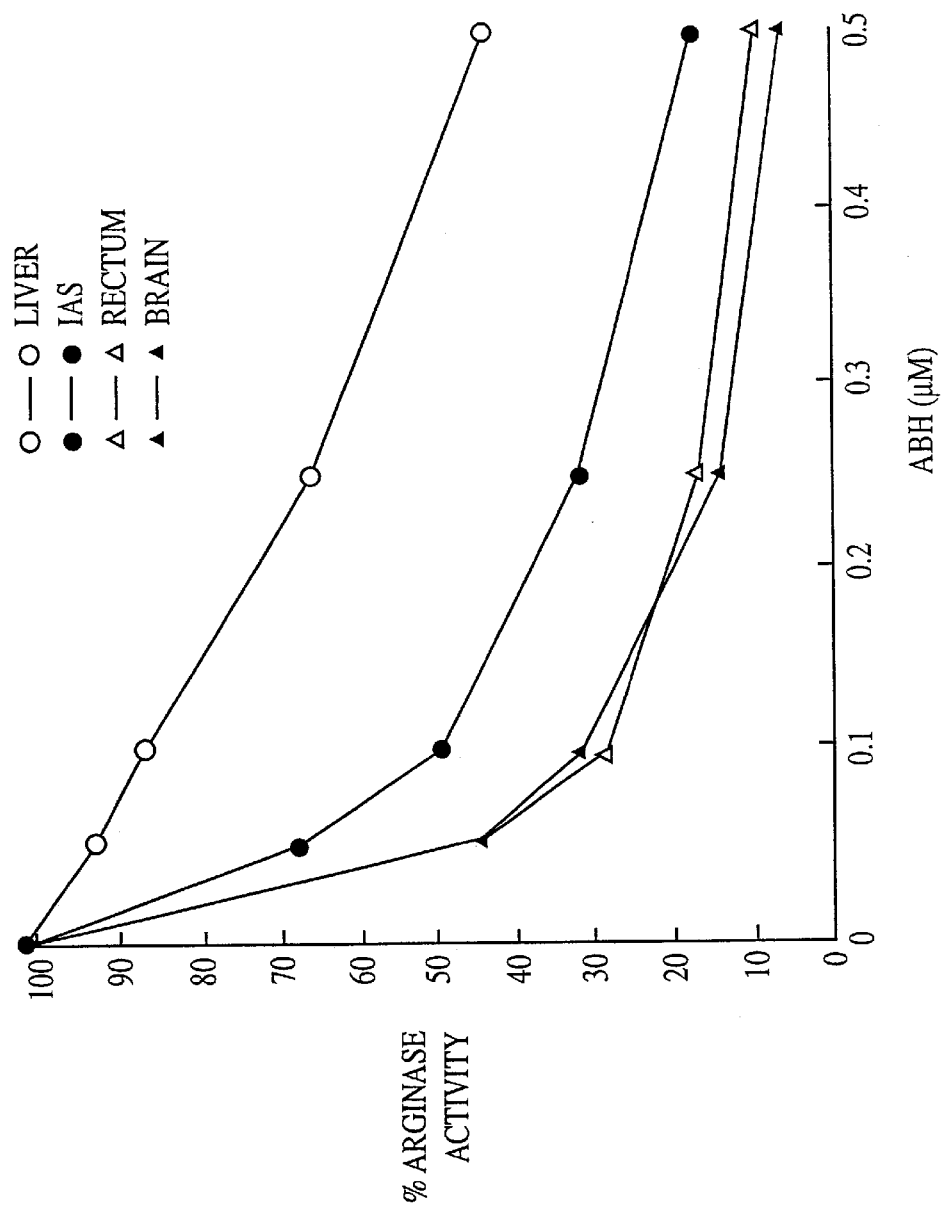
FIG. 27 is a graph depicting a comparison of the effect of ABHA on hepatic versus non-hepatic tissues (IAS, rectum, and brain). In contrast to the effects seen with $N^\omega$-hydroxy L-arginine, ABHA was a more potent inhibitor of non-hepatic than hepatic arginase activities.
Figure 28A:
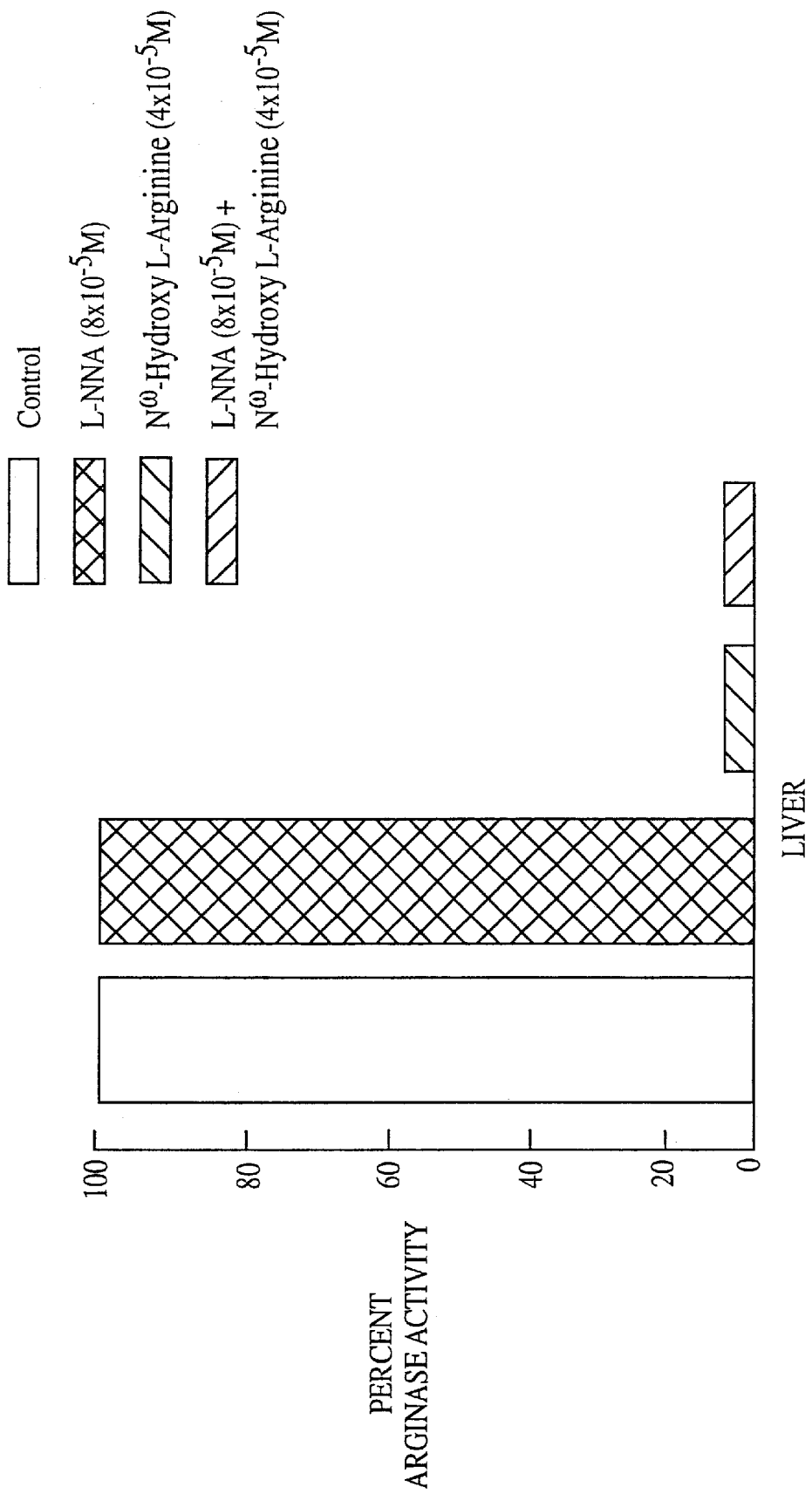
FIGS. 28A–28D, depicts the influence of the NO synthase inhibitor L-NNA, $N^\omega$-hydroxy-L-arginine (L-HO-Arg), and the combination of L-NNA and L-HO-Arg on liver arginase activity (FIG. 28A), IAS arginase activity (FIG. 28B), rectum arginase activity (FIG. 28C), and brain arginase activity (FIG. 28D). These data illustrate that L-NNA had no significant effect on either basal arginase activity or L-HO-Arg-attenuated arginase activity in the tissues examined. The data suggest that the differential inhibitory effects of L-HO-Arg in these tissues do not result from variable interactions of this NO synthase substrate with endogenous NO synthase.
Figure 28B:
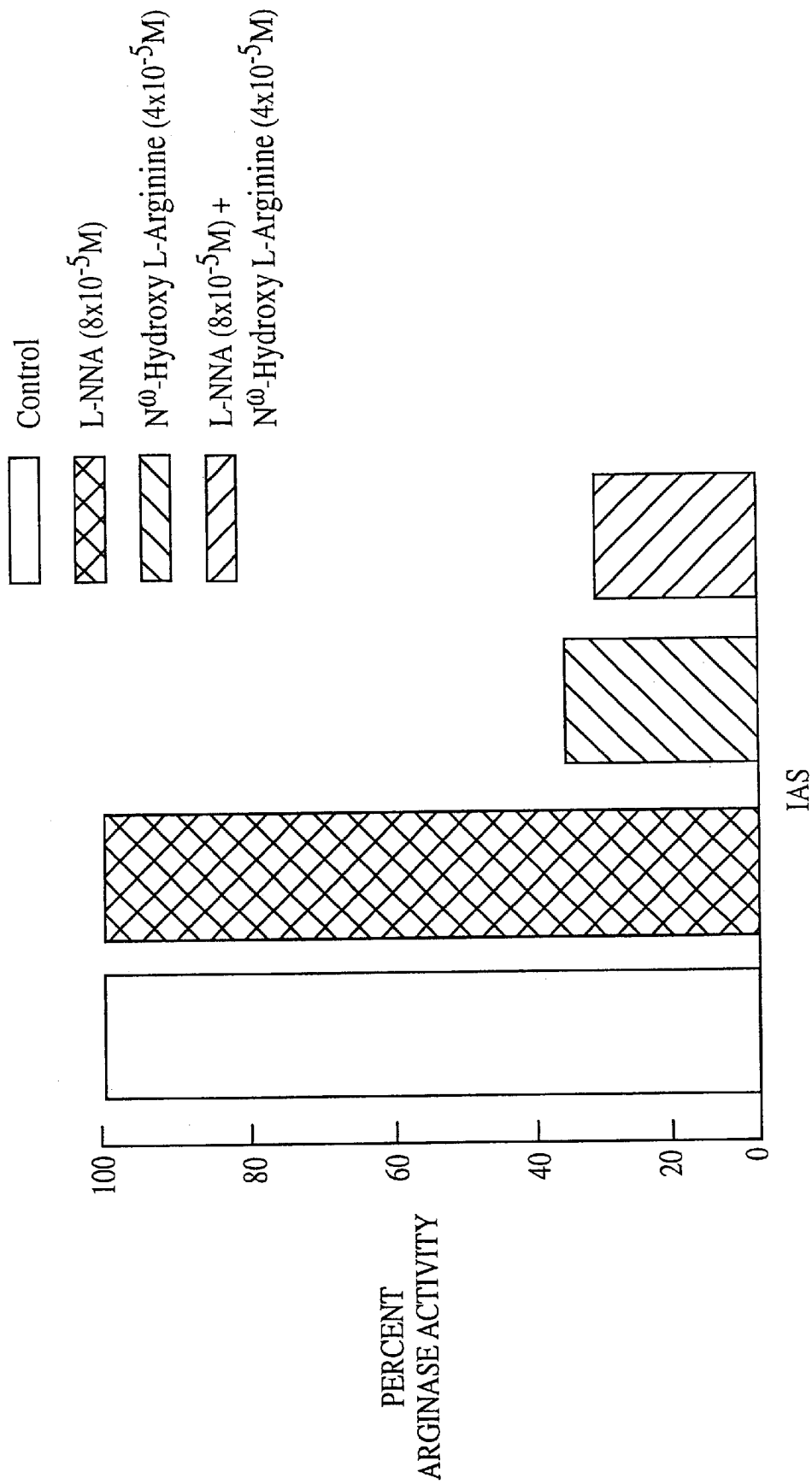
Figure 28C:
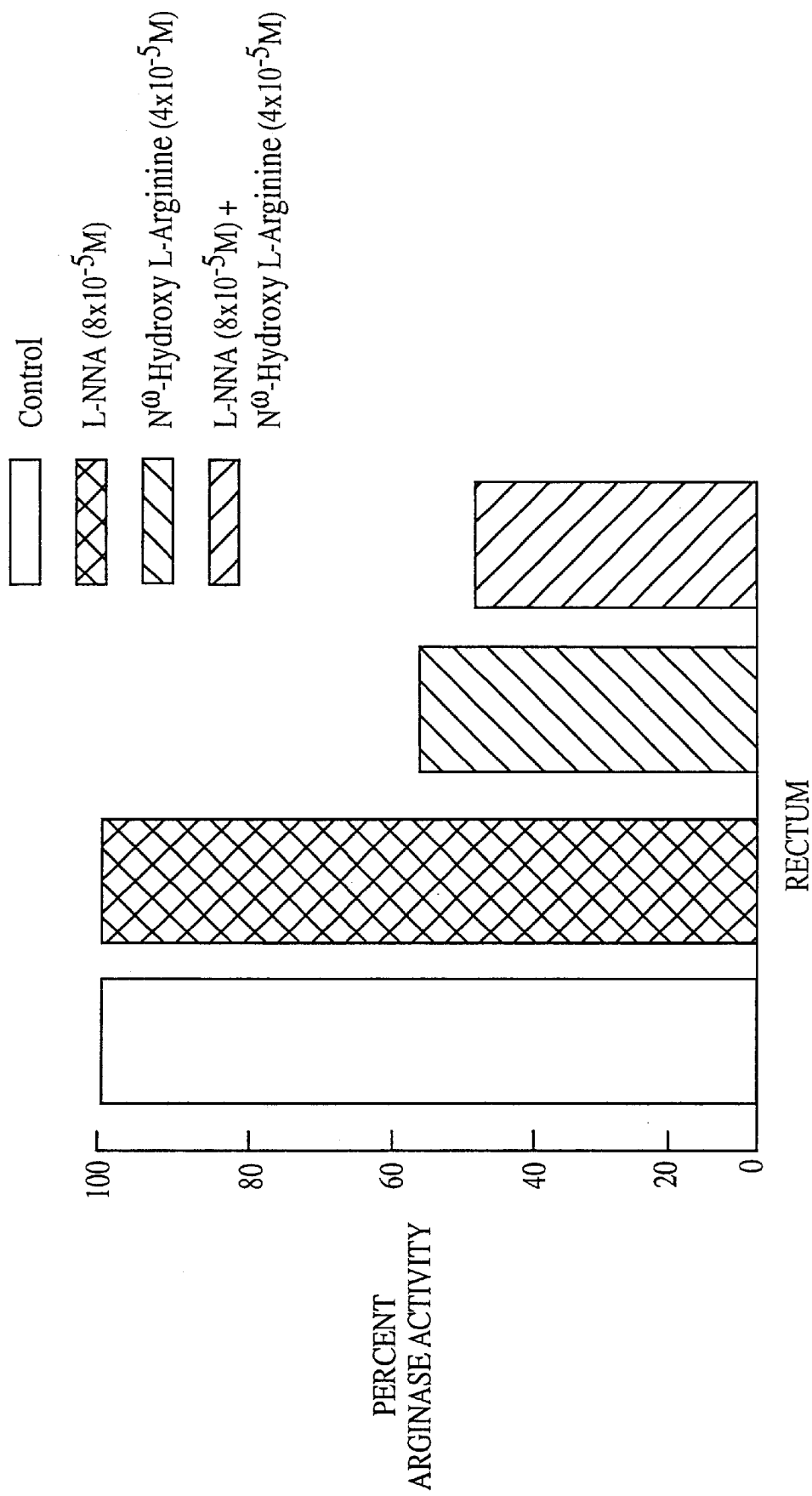
Figure 28D:
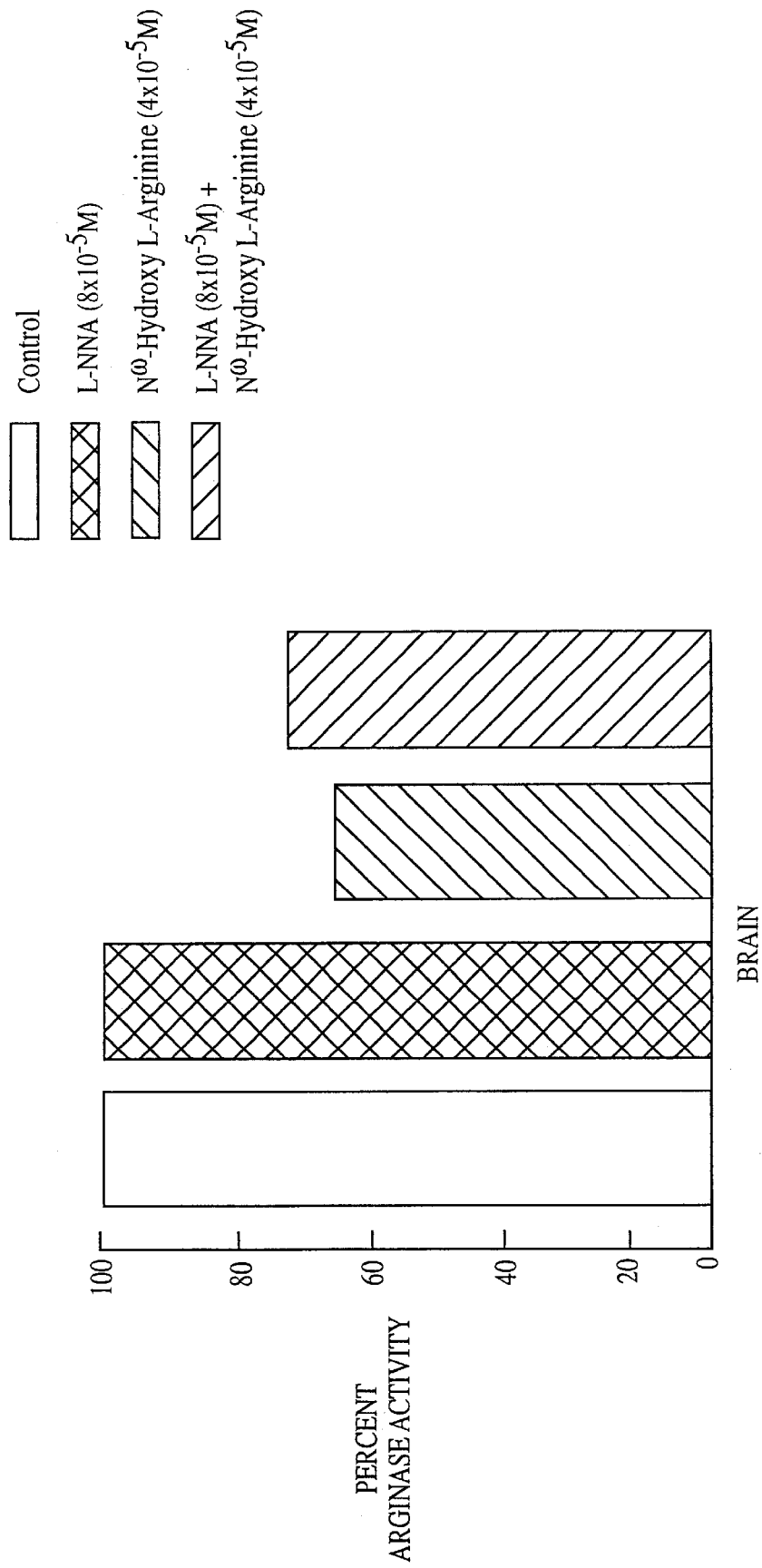

Influence of Arginase Inhibitors L-HO-Arg and ABHA on Basal Arginase Activity in Selected Tissues Among tissues investigated, L-HO-arg was the most potent inhibitor arginase activity in the liver (FIG. 26). IC50 values for the inhibition of arginase activity by L-HO-arg in liver, IAS, rectum, and brain homogenates were 2.4, 25, 42, and 40 micromolar, respectively. Thus, liver arginase activity was approximately 10–20-fold more sensitive to inhibition by L-HO-Arg than the arginase activities in the other tissues. The ability of ABRA to inhibit arginase activity in the tissues was in striking contrast to the inhibition observed with L-HO-Arg. ABHA was the most potent inhibitor of arginase activity in brain and rectum tissues, and also inhibited arginase in IAS and liver. The corresponding $IC_{50}$ values were 0.05 (brain), 0.05 (rectum), 0.10 (IAS), and 0.44 (liver) micromolar (FIG. 27). Inhibition constants for ABHA were estimated by titrating the inhibitor in assay mixtures containing a selected arginine concentration fixed at the $K_m$ value, and assuming competitive inhibition. These experiments yielded estimated $K_i$ values of 0.018, 0.026, 0.05, and 0.19 micromolar for arginase activities in brain, rectum, IAS, and liver, respectively. The estimated $K_i$ for ABHA inhibition of the liver enzyme is in good agreement with the $K_d$ of 0.11 micromolar determined by titration calorimetry.

Influence of the NO synthase Inhibitor L-N-Nitro-Arginase (L-NNA) and L-NNA Plus the Arginase Inhibitors on the arginase Activity in Different Tissues It is known that L-HO-Arg is not only an intermediate in the biosynthesis of NO, but is also a substrate for NO synthase. Thus, it is possible that tissue variations in inhibition of arginase activities by L-HO-Arg could be due to depletion of added L-HO-Arg by conversion to NO. In order to test this possibility, the effects of L-HO-Arg on arginase activities in the tissue homogenates were determined in the presence of the NO synthase inhibitor L-NNA. L-NNA, at 80 micromolar, had no effect on the activities of the various arginases in the presence of L-NO-Arg (FIG. 28), indicating that depletion of added L-HO-Arg by the action of NO synthase was not a concern in these experiments. Furthermore, the results indicate that tissue-specific variations in arginase inhibition by L-HO-Arg are likely to result from inherent differences in the arginase enzymes expressed in these tissues.

These studies demonstrate that ABHA is a potent, tissue-selective inhibitor of arginase. ABHA was 5,250,840, and 800 times more potent than L-HO-Arg in inhibiting the arginase activity in liver, IAS, rectum, and brain homogenates, respectively. Among the tissues examined, ABHA was more potent in inhibiting brain, rectum, and IAS arginase activity than the liver, with estimated $K_i$ values of 0.018, 0.026, and 0.05 micromolar, respectively, assuming competitive inhibition. Although complete inhibition patterns were not determined, previous studies have shown that ABHA can displace the competitive inhibitor L-HO-Arg from the rat liver enzyme (Example 2). In contrast to the inhibition results with ABHA, L-HO-Arg was more potent in inhibiting arginase activity in liver homogenates than in the other tissues (FIG. 26).

Two isozymes of arginase have been described in mammals, the hepatic (type I) arginase and non-hepatic type (type II) arginase (Jenkinson et al., 1996, Comp. Biochem. Physiol. 114B:107–132; Buga et al., 1996, Am. J. Physiol. Heart Circ. Physiol. 271: H1988–H1998; Daghigh et al., 1994, Biochem. Biophys. Res. Commun. 202:174–180; Boucher et al., 1994, Biochem. Biophys. Res. Commun. 203:1614–1621; Hecker et al., 1995, FEBS Lett. 359:251–254; Gotoh et al., 1996, FEBS Lett. 395:119–122). 122). Type I arginase is found predominantly in mammalian liver and red blood cells, while the type II enzyme is thought to be expressed in macrophages, kidney and endothelial cells. Although the expression patterns for the arginase in opossum rectum, brain, IAS, and liver are not known, the differential effects of ABHA and L-HO-Arg on arginase activities in these tissues are consistent with type II enzyme expression in the non-hepatic tissues.

The higher potency of L-HO-Arg against hepatic arginase, as compared to the non-hepatic tissue extracts might be related to the ability of L-HO-Arg to serve as a substrate for NO synthase. Thus, in tissues expressing high levels of NO synthase, L-HO-Arg would be rapidly converted to NO and citrulline, lowering the effective concentration of L-HO-Arg and decreasing arginase inhibition. To assess this possibility, inhibition studies with L-HO-Arg were repeated in the presence of L-NNA, a known inhibitor of NO synthase. Control experiments established that L-NNA had no effect on the arginase activities of the various tissues. The combination of L-NNA and L-HO-Arg was no more effective than L-HO-Arg alone for inhibiting arginase activities, indicating that the differential inhibition of the arginase activities in liver, tow brain, rectum, and IAS is not attributable to NO synthase depletion of L-HO-Arg, and is therefore likely to reflect differences in affinity of the arginase for the inhibitor.

The functional data in IAS also indicate that ABHA is a more selective inhibitor of arginase than is L-HO-Arg. This was evident from IAS studies in the presence of the NO synthase inhibitor L-NNA. L-HO-Arg can serve as an NO synthase substrate. The experiments described in this Example were performed to examine the influence of L-HO-Arg on NANC relaxation of IAS that was attenuated by the NO synthase inhibitor. The effects of L-HO-Arg and ABHA in reversing attenuation of NANC relaxation were compared with L-arginine, an authentic substrate for NO synthase. Interestingly, L-HO-Arg reversed L-NNA-attenuated NANC relaxation of IAS with a potency comparable to L-arginine. ABHA, on the other hand, had no effect on IAS relaxation suppressed by the NO synthase inhibitor. This suggests that L-HO-Arg may in part be a substrate for NO synthase and that it may be a less selective inhibitor of arginase than is ABHA.

Before the present study, there had been only limited information on the physiological relevance of arginase in NANC nerve-mediated relaxation in gastrointestinal smooth muscle. The data in this Example demonstrate that arginase inhibitors L-HO-Arg and ABHA augment NANC nerve-mediated relaxation of the IAS. Because NO synthase pathway is the predominant pathway responsible for the NANC nerve-mediated relaxation of IAS (Rattan and Chakder, 1992, Am. J. Physiol. Gastrointest. Liver Physiol. 262:G107–G112; Rattan et al., 1992, Gastroenterology 103:43–50), augmentation of IAS relaxation is believed to be due to up-regulation of the NO synthase pathway induced by an increase in tissue levels of L-arginine.

It has been established that exogenously administered L-arginine has no significant effect on NANC relaxation of IAS unless the tissues are L-arginine deficient (Chakder and Rattan, 1997, J. Pharmacol. Exp. Ther. 282:378–384). In the basal state in normal tissues, exogenous L-arginine has no significant effect on either basal IAS tone or NANC relaxation (Chakder and Rattan, 1997, J. Pharmacol. Exp. Ther. 282;378–384). Conversely, in L-arginine-deficient tissues, exogenous L-arginine causes a significant decrease in basal IAS tone and reversal of impaired NANC relaxation in IAS smooth muscle (Chakder and Rattan, 1997, J. Pharmacol. Exp. Ther. 282:378–384; Rattan and Chakder, 1997, Gastroenterology 112:1250–1259).

It is believed that the effect of exogenous L-arginine in L-arginine deficient tissues is attributable to an increase in arginine uptake which leads to augmentation of NANC relaxation via up-regulation of the NO synthase pathway. Such mechanisms may not be operative in normal tissues due to the normal state of equilibrium of L-arginine levels at cellular levels. Augmentation of NANC relaxation in the presence of arginase inhibitors can be due to an increase in intracellular L-arginine levels, as proposed in other non-gastrointestinal tissues (Jenkinson et al., 1996, Comp. Biochem. Physiol. 114b:107–132; Buga et al., 1996, Am. J. Physiol. Heart Circ. Physiol. 271:H1988–H1998; Boucher et al., 1994, Biochem. Biophys. Res. Commun. 203:1614–1621; Hecker et al., 1995, FEBS Lett. 359:251–254).

In IAS, ABHA was about 250 times more potent an arginase inhibitor than L-HO-Arg. However, in smooth muscle NANC relaxation experiments, these two agents were approximately equipotent for augmenting NANC relaxation. In the functional data, smooth muscle relaxation is the final outcome of multiple pathways that involve not only arginase but also NO synthase. Net IAS smooth muscle relaxation in response to NANC nerve stimulation in the presence of inhibitors is the result of their interaction with different pathways available to them. L-HO-Arg acts as both an arginase inhibitor and a substrate for NO synthase. ABHA, on the other hand, is selective for arginase inhibition only (Rattan and Chakder, 1992, Am. J. Physiol. Gastrointest. Liver Physiol. 262:G107–G112; Rattan et al., 1992, Gastroenterology 103:43–50; Chakder and Rattan, 1993, Am. J. Physiol. Gastrointest. Liver Physiol. 264:G7–G12. Others have shown that the NO synthase pathway is the predominant pathway for NANC nerve-mediated smooth muscle relaxation(Tottruo et al, 1992, Gastroenterology 102:409–415; O'Kelly et al., 1993, Gut 34:689–693). Therefore, augmentation of NANC relaxation in IAS by L-HO-Arg can be due to the summation of its effects.

An increase in tissue arginase levels has been associated with a number of pathological conditions, including gastric cancer (Wu et al., 1992, Life Sci. 51:1355–1361; Leu and Wang, 1992, Cancer 70:733–736; Straus et al., 1992, Clin. Chim. Acta 210:5–12; Ikemoto et al., 1993, Clin. Chem. 39:794–799; Wu et al, 1994, Dig. Dis. Sci 39:1107–1112). Additionally, elevated arginase levels following human orthotopic liver transplantation have been shown to cause pulmonary hypertension and reduced hepatic blood flow (Langle et al., 1997, Transplantation 63:1225–1233; Langle et al., 1995, Transplantation 59:1542–1549). Higher blood levels of arginase have been found in patients with various tumors (Wu et al., 1992, Life Sci. 51:1355–1361; Leu and Wang, 1992, Cancer 70:733–736; Straus et al., 1992, Clin. Chim. Acta 210:5–12; Wu et al. 1994, Dig. Dis. Sci., 39:1107–1112; Paranuli and Singh, 1996, Cancer Lett., 107:249–256) and in patients afflicted with certain forms of hepatic injury (Ikemoto et al., 1993, Clin. Chem. 39:794–799). Arginase inhibitors therefore can have a significant role in pathophysiology and potential therapy in a number of disorders in humans and other mammals.

In addition to its therapeutic potential, ABHA can have a novel role in the identification of isozyme-specific arginase pathways and their role as therapeutic potential for the specific control of the hemodynamic effects associated with the unregulated arginage activity.

EXAMPLE 5

Arginase-Boronic Acid Complex Highlights a Physiological Role in Erectile Function The crystal structure of the complex formed between the bi-nuclear manganese metalloenzyme arginase and 2(S)-amino-6-boronohexanoic acid (AB HA) has been determined at 1.7 angstrom resolution from a crystal perfectly twinned by hemihedry. ABHA binds as the tetrahedral boronate anion, with one hydroxyl oxygen symmetrically bridging the bi-nuclear manganese cluster and a second hydroxyl oxygen coordinating to $Mn^{2+}_A$. This binding mode mimics the transition state of a metal-activated hydroxide mechanism. This transition state structure differs from that occurring in NO biosynthesis, thereby explaining why AHA does not inhibit NO synthase. Arginase activity is present in the penis. ABHA causes significant enhancement of non-adrenergic, non-cholinergic (NANC0 nerve-mediated relaxation of penile corpus cavenosum smooth muscle, indicating that arginase inhibition sustains L-arginine concentration at a sufficiently high level in the muscle that NO synthase is active. Thus, the experiments presented in this Example demonstrate that human penile arginase is a target for therapeutic intervention in treatment of erectile dysfunction.

The materials and methods used in the experiments presented in this Example are now described.

Crstallization and Data Collection

Crystals of arginase-ABHA complex were prepared at room temperature (i.e. about 20° C.) by equilibrating a hanging drop containing 5 microliters of protein solution (11 milligrams per milliliter of arginase, 2 millimolar ABHA, 4 millimolar $MnCl_2$, 2 millimolar beta-mercaptoethanol, and 25 millimolar bicine {pH 8.5}, and 5 microliters of precipitant solution {26% polyethylene glycol 1500, 100 millimolar bicine <pH 8.1>}) against 1 milliliter of precipitant solution in the well reservoir. hexagonal rod-shaped crystals with approximate dimensions of 0.1×0.1×0.5 millimeters appeared within 2 weeks. Diffraction data were collected from a single flash-cooled crystal of the arginase-ABHA complex at CHESS (Cornell High Energy Synchotron Source) beamline A-1, and intensity data integration and reduction were performed using DENZO and SCALEPACK software, respectively, as described (Otwinowski et al., 1997, Meth. Enzymol. 276:307–326).

Phasing and Refinement of the Twinned Structure

Initial phasing by molecular replacement with AMoRe software (Navaza, 1994, Acta Crystallogr. A50:157–163) was achieved using the structure of the native rat liver arginase monomer (Kanyo et al., 1996, Nature 383:554–557) as a search probe. Using intensity data in the 20–3 angstrom shell with $I>3\sigma$, the cross rotation search yielded two equivalent $10.7\sigma$ peaks at $\alpha=34.9°$, $\beta=126.4°$, $\gamma=283.0°$ and $\alpha=94.9°$, $\beta=126.6°$, $\gamma=283.3°$ (next highest peak=$5.6\sigma$). Subsequent translation searches yielded $13.9\sigma$ and $10.8\sigma$ peaks corresponding to fractional coordinates x=0.2436, y=0.2756, z=0.0000 and x=0.3330, y=0.9348, z=0.5009 (next highest peak=$2.6\sigma$). Rigid body refinement of this solution lowered the crystallographic R factor from 0.503 to 0.379. Monomer positions in twin domain B were generated by applying the twin operation to the molecular replacement model.

Iterative rounds of refinement and rebuilding of the native model were performed using CNS and O, as described (Brünger et al., 1998, Acta Crystallogr. D49:375–380; Jones et al., 1991, Acta Crystallogr. A47:110–119). For refinement with CNS against the measured twinned structure factor amplitudes $|F_{obs}|$, the target residual was based on the numerator of $R_{twin}$ (Table 8) and implemented in CNS version 0.5. Each twin domain was defined as an 'alternate conformation' with occupancy set to ½, and interactions between mutually exclusive twin domains were disengaged.

After each round of CNS refinement, the in-progress atomic model was used to deconvolute each measured intensity $I_{obs}$ into estimated crystallographic intensities $I_{obs/A}$ and $I_{obs/B}$ corresponding to twin domains A and B. For omit map calculation, residues were deleted prior to the structure-based deconvolution of $I_{obs}$ in order to minimize model bias. A bulk solvent term was included in the model prior to calculation of structure factor amplitudes, which improved the quality of the electron density maps; map averaging across both twin domains additionally improved map quality. In the final stages of refinement, the inhibitor ABHA was built into clear and unbiased electron density when $R_{twin}$ decreased to 0.184. Strict non-crystallographic symmetry constraints were employed during refinement, and these were relaxed to appropriately weighted restraints as judged by $R_{twin/free}$. Data collection and refinement statistics are reported in Table 8.

Organ Bath Experiments Penile cavernosal tissue strips were obtained from male New Zealand white rabbits (3.0–3.5 kilogram body weight) and mounted in organ bath preparations, as described (Kim et al., 1991, J. Clin. Invest. 88:112–118). Tissues strips at optimal isometric tension were contracted using 40 nanomolar endothelin-1 and subjected to electrical field stimulation (EFS), by means of two platinum plate electrodes positioned on either side of the tissue and a current amplifier in series with a square pulse stimulator. Each stimulation period lasted 20 seconds with trains of square waves having a pulse duration of 0.5 milliseconds and a potential difference of 10 volts. Frequency was varied from 1 to 10 Hertz. For all experiments, NANC responses were isolated in tissue strips by treatment with indomethacin to inhibit vasoactive prostanoid synthesis, 10 micromolar bretylium to inhibit adrenergic neurotransmission, and 1 micromolar atropine to block muscarinic acetylcholine receptors. All tissues were first subject to EFS in the absence of ABHA, and then stimulations were repeated in the presence of increasing concentrations (0.1 to 1.0 millimolar) ABHA following a 20 minute incubation period. At the end of each experiment, all tissue strips were treated with 10 micromolar papaverine and to micromolar nitroprusside to induce maximal relaxation (100%). For each experiment, the response at each frequency in the presence of ABHA was compared to control responses using a paired t-test method. Responses were further analyzed by determining the ratios of the responses in the presence and absence of ABHA treatment. Comparisons were judged statistically significant if the two-tailed p-value$\leq$0.05.

Nitric Oxide Synthase-ABHA Assay

NADPH, FAD, FMN, L-arginine, N-(2-hydroxyethyl) piperazine-N-2-ethanesulfonic acid (HEPES) (6R)-5,6,7,8-tetrahydro-L-biopterin ($BH_4$), aminoguanidine, $CaCl_2$, and phosphodiesterase cyclic nucleotide activator (calmodulin) were purchased from Sigma Chemical Company (St. Louis, Mo.). Neuronal NO synthase was purchased from Biomol, dialyzed to remove beta-mercaptoethanol, and concentrated to 0.1 milligram per milliliter. The nitric oxide synthase colorimetric assay kit was purchased from Calbiochem. Materials were used without further purification. The effect of ABHA on NO synthesis was assayed by monitoring the sum of $NO_2^-$ and $NO_3^-$ production, as described (Verdon et al., 1995, Anal. Biochem. 224:502–508). The enzyme solution was shaken at 37° C. for 15 minutes with 50 millimolar HEPES (pH 7.5), 100 micromolar NADPH, 4 micromolar FAD, 4 micromolar FMN, 6 micromolar $BH_4$, 100 micromolar L-arginine, 0.0–1.0 millimolar ABHA, and 0.02 milligram per milliliter NO synthase in a final volume of 100 microliters. For experiments in which neuronal NO synthase was used, 1 millimolar $CaCl_2$ and 100 micrograms per milliliter calmodulin were also added. Reactions were stopped by incubating the reaction mixture at 100° C. for 3 minutes. Nitrate was reduced to nitrite using nitrate reductase (40 minutes at room temperature), and the remaining NADPH was depleted by incubation with lactate dehydrogenase and sodium pyruvate for 20 minutes at room temperature. Addition of the Greiss reagents, sulfanilamide and N-(1-naphthyl)-ethylenenediamine, converted all available nitrite into a deep purple azo compound. Absorbance at 540 nanometers was used to quantify the extent of $NO_x$ production.

Measurement of Arginase Activity

Human penile cavernosal tissue was obtained from patients undergoing implantation of penile prostheses, as described (Kim et al., 1991, J. Clin. Invest. 88:112–118). Human and rabbit cavernosal tissue was frozen in liquid nitrogen and pulverized. The resulting tissue powder was combined 1:4 (weight:volume) with ice-cold buffer comprising 20 millimolar HEPES (pH 7.4), and 0.25 molar sucrose. The mixture was homogenized on ice in the presence of protease inhibitors (PMSF, leupeptin, and aprotinin at protease-inhibiting concentrations) using a Brinkmann PT3000 polytron. The homogenate was centrifuged at 3000×g for 20 minutes, and the supernatant was used for enzyme assay. Arginase activity was assayed as described (Rüegg et al., 1980, Anal. Biochem. 102:206–212). Briefly, 10 microliter aliquots of tissue extract were incubated with increasing concentrations of non-labeled L-arginine and 100,000 dpm of [14C-guanidino]-L-arginine (obtained from NEN Life Science Products) in 90 microliters of buffer (74 millimolar glycine {pH9.7}, 0.25 millimolar $MnCl_2$) for 60 minutes at 25° C. To terminate the reaction, 400 microliters of 0.25 molar acetic acid (pH 4.5), 7 molar urea, and 10 millimolar L-arginine was added to each tube. After addition of 500 microliters of water, samples were passed through a 0.5-milliliter column of Dowex™ 50W-X8 resin (obtained from Bio-Rad Laboratories). Tubes were rinsed twice with 500 microliter aliquots of water, and both rinses were poured onto the column. Finally, columns were washed with 1 milliliter of water. All effluent was collected in 20 milliliter vials and combined with 16 milliliters of Liquiscint™ (obtained from National Diagnostics). Radioactivity was quantified by liquid scintillation spectroscopy using a Packard Tri-Carb™ 2300TR Analyzer. All measurements were performed in 6 replicate samples.

Crystallographic Coordinates

Coordinates of the arginase-ABHA complex were deposited in the Protein Data Bank, and were assigned accession code 1D3V.

The results of the experiments presented in this Example are now described.

Structure Determination from a Twinned Arginase Crystal

A single crystal of the arginase-ABHA complex diffracted to 1.7 angstrom resolution at CHESS. The data collection and refinement statistics for this crystal are listed in Table 8.

TABLE 8

| | |
|---|---|
| Resolution (Angstroms) | 1.7 |
| Total reflections | 126,870 |
| Unique reflections | 66,822 |
| Completeness | 91.7% |
| $R_{merge}$[1] | 0.053 |
| Reflections used in refinement (>2σ) | 64,734 |
| Protein atoms (N)[2] | 2,345 |
| Inhibitor atoms (N)[2] | 13 |
| Solvent atoms (N)[2] | 150 |
| Manganese ions (N)[2] | 2 |
| $R_{twin}$[3] | 0.157 |
| $R_{twin/free}$[3] | 0.179 |
| R.m.s. deviations: | |
| Bonds (angstroms) | 0.008 |
| Angles (degrees) | 1.4 |
| Dihedrals (degrees) | 23.1 |
| Impropers (degrees) | 0.9 |

[1]$R_{merge} = \Sigma |I_i - <I_i>|/\Sigma|<I_i>|$, where $I_i$ is the intensity measurement for reflection i, and $<I_i>$ is the mean intensity calculated for reflection i from replicate data.
[2]per monomer
[3]$R_{twin} = \Sigma(|F_{obs}| - [|F_{calc/A}|^2 + |F_{calc/B}|^2]^{1/2})/\Sigma|F_{obs}|$, where $|F_{obs}|$ is observed structure factor amplitude derived from twinned intensity $I_{obs}$, and $|F_{calc/A}|$ and $|F_{calc/B}|$ are structural factor amplitudes calculated for the separate twin domains A and B, respectively. $R_{twin}$ underestimates the residual error in the model by averaging the difference between observed and calculated structure factor amplitudes over the two twin-related reflections. The same expression describes $R_{twin/free}$, which was calculated for 3,331 test set reflections held aside during refinement.

Diffraction intensities exhibited symmetry consistent with space group P6 (unit cell parameters a=b=91,3 angstroms, c=69.6 angstroms; one monomer in the asymmetric unit), but this assignment was inconsistent wit the molecular symmetry of the arginase trimer. Subsequent analysis of measured intensities revealed deviations from Wilson statistics with $<I^2>/<I>^2$=about 1.5 for thin resolution shells, indicative of perfect hemihedral twinning that obscured the true crystallographic symmetry of space group P3. Two monomers (from two separate trimers) occupy the asymmetric unit.

Initial phasing was achieved by molecular replacement. Ultimately, four independent copies of the arginase monomer were accounted for—the two in the asymmetric unit and their two twins. For the calculation of electron density maps, structure factor amplitudes were calculated from deconvoluted intensities using the structure-based algorithm of Redinbo et al (1993, Acta Crystallogr. D49:375–380). The structure of the enzyme-inhibitor complex was refined against $|F_{obs}|$ simultaneously in both twin domains using CNS with a modified target residual, as described (Brünger et al., 1998, Acta Crystallogr. D54:905–921).

Mechanistic Inferences from Inhibitor Binding

Figure 29A:
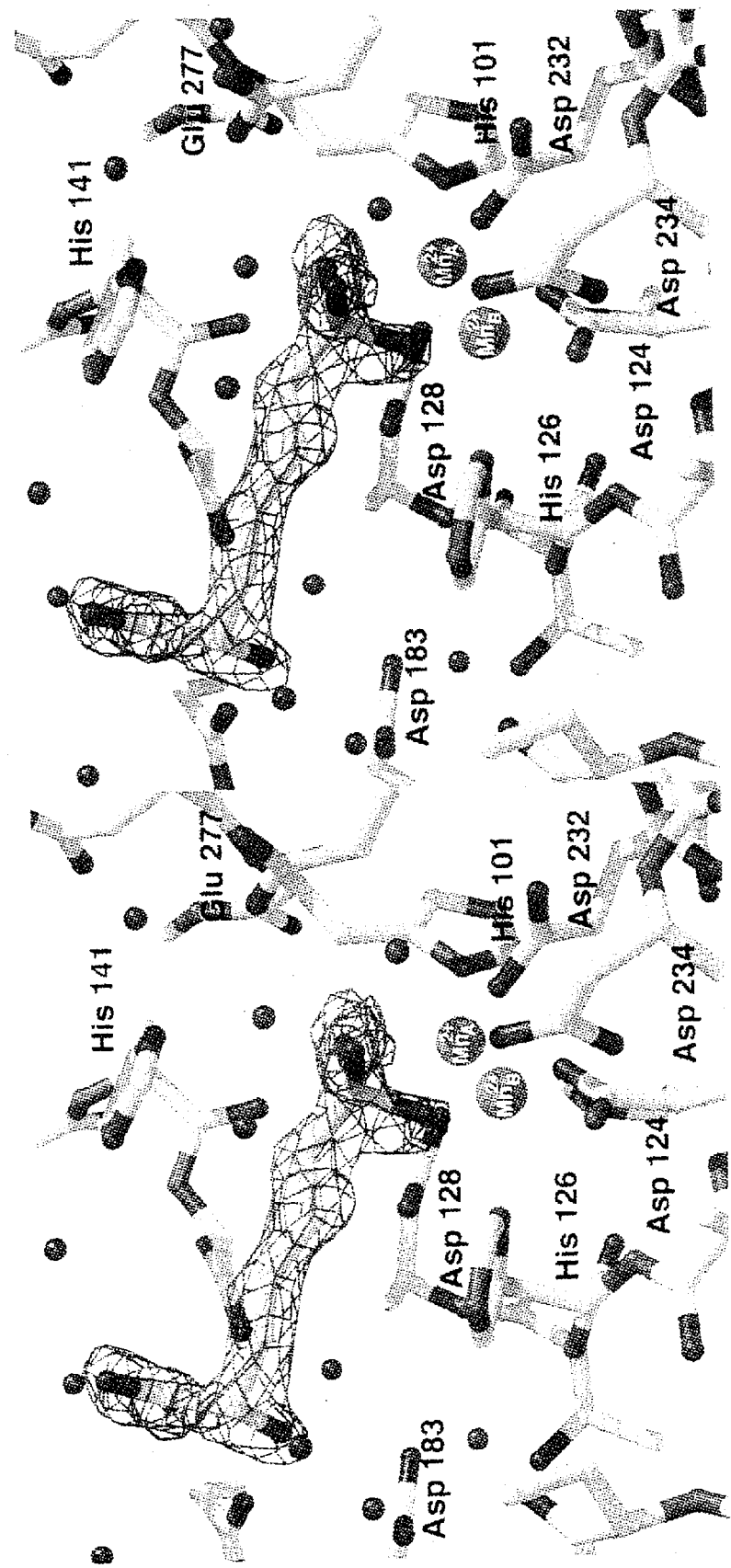
FIGS. 29A, 29B, and 29C is a trio of diagrams which depict the structure and arrangement of the arginase-ABHA complex.
Figure 29B:
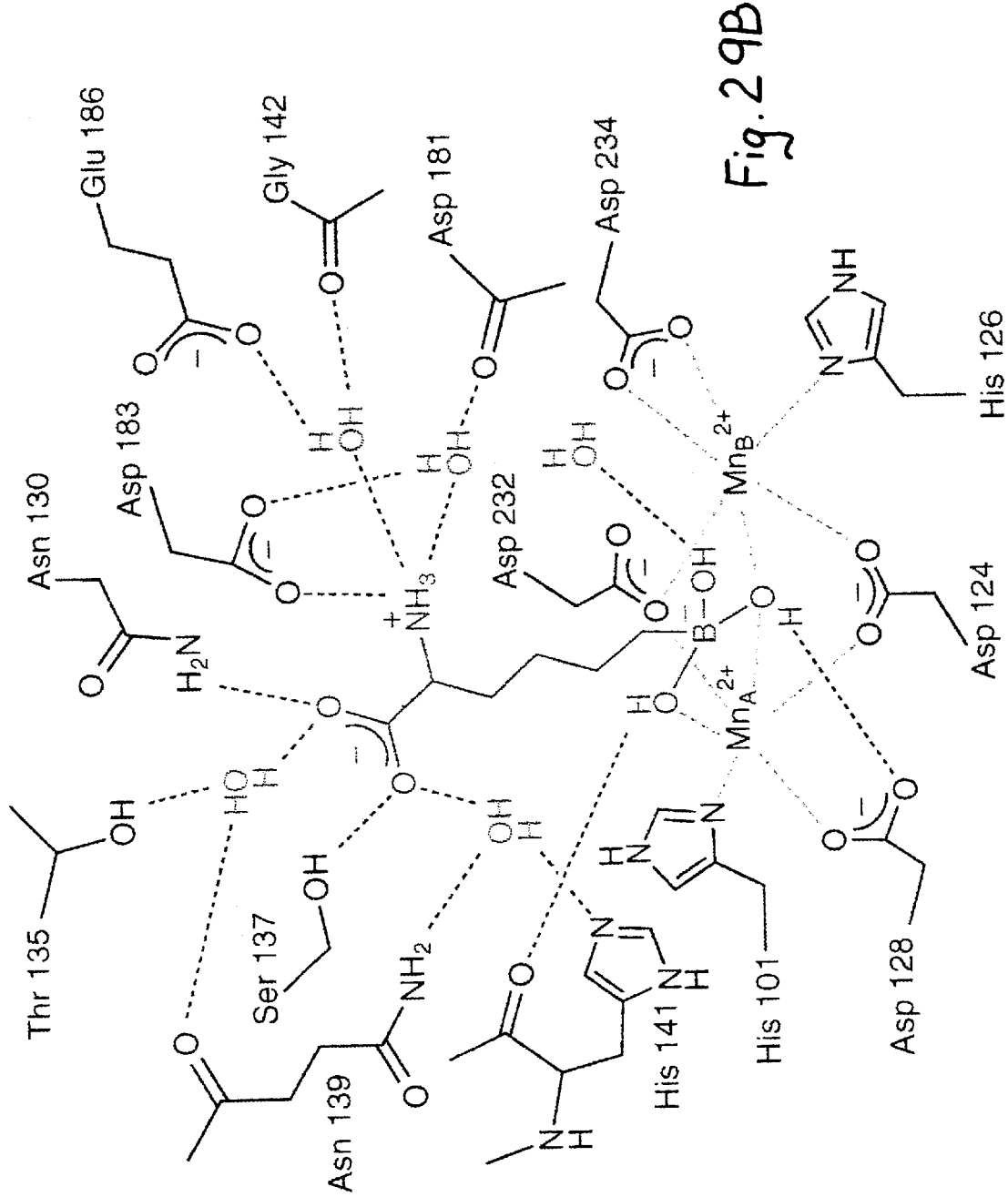
Figure 29C:
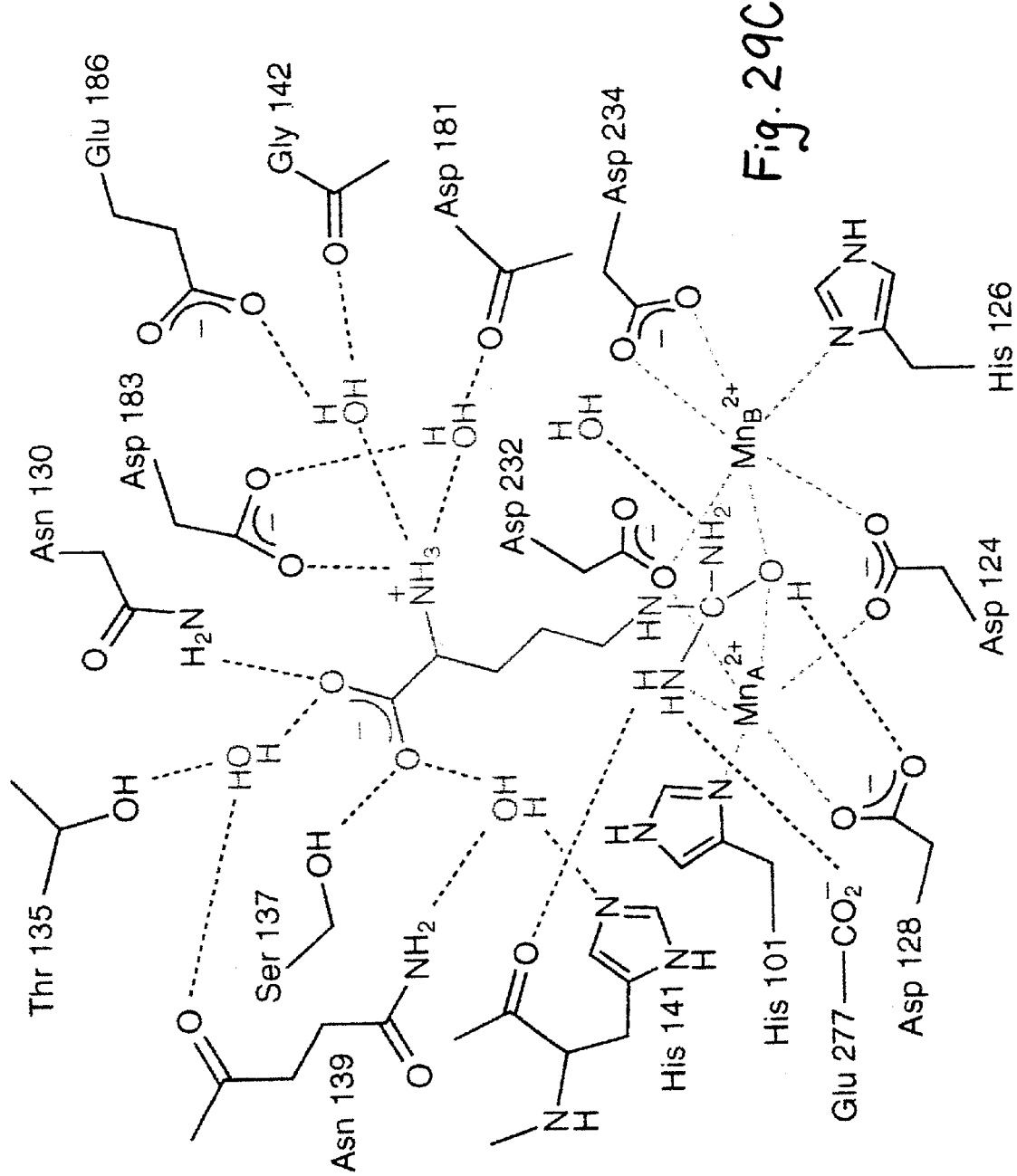

The trigonal planar boronic acid group of ABHA is hydrated to form the tetrahedral boronate anion in the arginase-ABHA complex, as illustrated in FIGS. 29A and 29B. A single boronate hydroxyl group (O1) symmetrically bridges the bi-nuclear manganese cluster ($Mn^{2+}_A$—O and $Mn^{2+}_B$—O separations=2.2 angstroms) and also donates a hydrogen bond to Oδ2 of Asp-128. This binding mode mimics the first step of the proposed arginase mechanism (see, e.g. Kanyo et al., 1996, Nature 383:554–557), in which a metal-bridging hydroxide ion attacks the trigonal planar guanidinium group of L-arginine to form a tetrahedral intermediate bridging both metal ions, as illustrated in FIG. 29C.

A second boronate hydroxyl group (O2) coordinates to $Mn^{2+}_A$ with a longer Mn—O separation of 2.4 angstroms. Therefore, inhibitor binding changes the geometry of the $Mn^{2+}_A$ coordination polyhedron from square pyramidal in the native enzyme to distorted octahedral in the enzyme-inhibitor complex. There is no net change in the coordination geometry of $Mn^{2+}_B$, which remains distorted octahedral. The $Mn^{2+}_A$—$Mn^{2+}_B$ separation increases slightly, from 3.3 angstroms in the native enzyme to 3.4 angstroms in the enzyme-inhibitor complex.

The negatively charged carboxylate group of Glu-277 does not hydrogen bond to both boronate hydroxyl groups O2 and O3 (O—O separations=3.4 angstroms and 3.8 angstroms), contrary to the expectations of Baggio et al. (1997, J. Amer. Chem. Soc. 119:8107–8108). However, modeling experiments indicate that a double salt link between Glu-277 and the substrate would place the scissile guanidinium group directly over metal-bridging hydroxide ion (Kanyo et al., 1996, Nature 383:554–557). Additionally, L-arginine hydrogen bonds with this glutamate residue in the inactivated arginase from B. caldovelox arginase (Bewley et al., 1999, Structure 7:435–448). The lack of a corresponding hydrogen bond in the arginase-ABHA complex may result from electrostatic repulsion with the negatively charged boronate anion. Such a repulsive interaction would not occur with the neutral tetrahedral intermediate occurring in the arginase mechanism (see FIG. 29C).

An extensive network of hydrogen bond interactions with the alpha-amino and alpha-carboxylate groups of ABHA reveal the structural and stereochemical basis for substrate specificity toward free L-arginine, as illustrated in FIG. 29B (see also Reczkowski et al., 1994 Arch. Biochem. Biophys. 312:31–37). Alteration of the alpha-amino or alpha-carboxylate groups of L-arginine would significantly compromise enzyme-substrate hydrogen boding, recognition, and catalysis. Notably, most of these hydrogen bond interactions are conserved in the complex of L-arginine with the inactivated arginase from B. caldovelox.

Arginase and the Physiology of Penile Erection

The arginase inhibitor ABHA is the most potent and most stable inhibitor of arginase reported to date. Because the tetrahedral intermediate in the NO synthase mechanism (see Stuehr et al., 1992, Adv. Enzymol. 65:287–346) cannot be mimicked by the ABHA boronate anion, ABHA does not inhibit NO synthase (e.g. no inhibition of NO synthase is observed, either at a concentration 0.1 millimolar or 1.0 millimolar ABHA). With the discovery, described herein, that arginase activity occurs in corpus cavenosum tissue extracts prepared from rabbit penis and human penis, it is now possible to probe the physiological relationship between arginase and NO synthase in penile corpus cavenosum.

Figure 30:
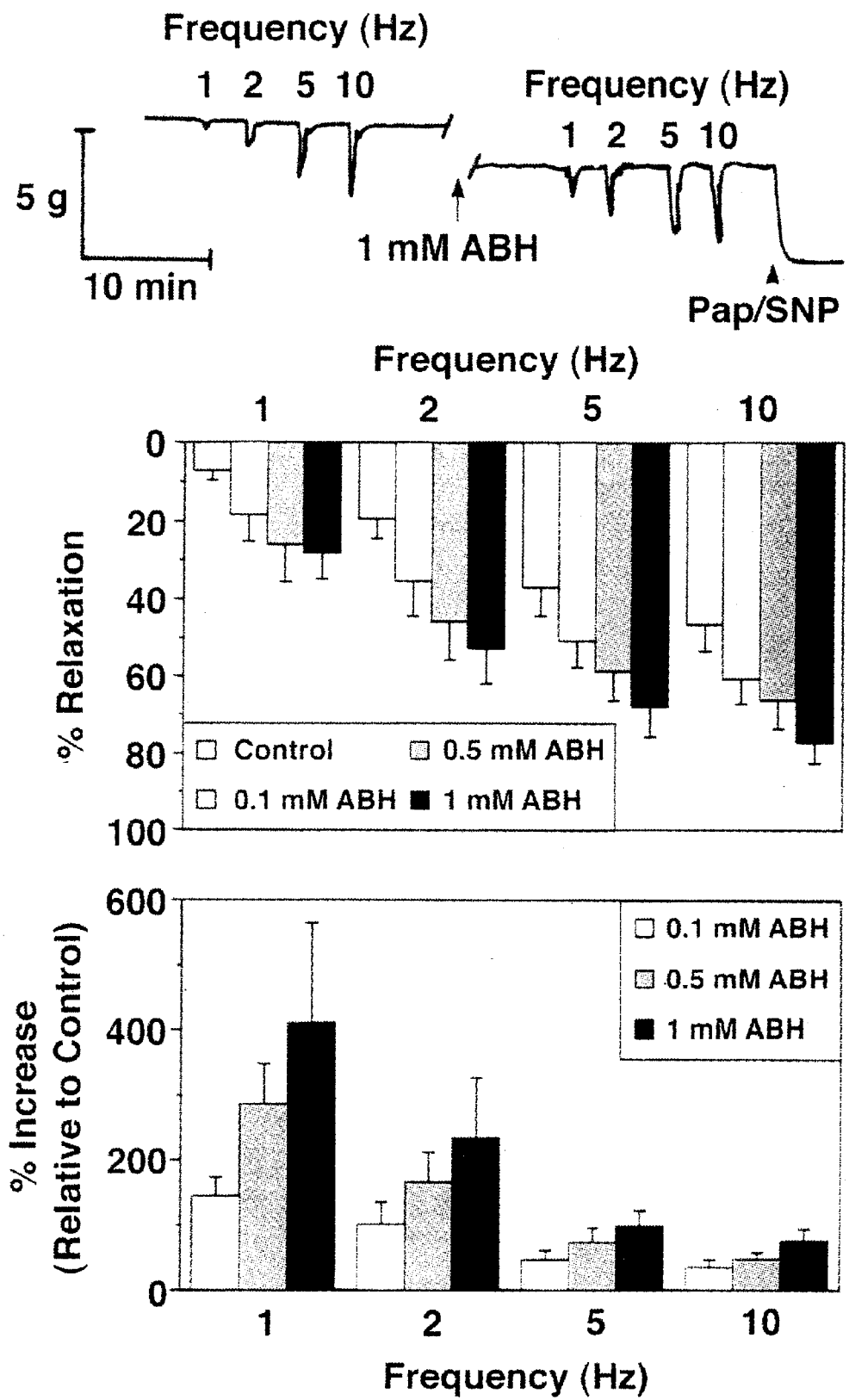
FIG. 30, comprising

The effects of ABHA on smooth muscle contractility was studied using organ bath preparations of rabbit penile corpus cavenosum. Tissue strips were procured and prepared, and NANC nerve-mediated responses were elicited by EFS at varying frequencies. These responses are sensitive to the neurotoxin tetrodotoxin, and are not dependent on the presence of the endothelium (Kim et al., 1991, J. Clin. Invest. 88:112–118; Saenz de Tejada et al., 1988, Amer. J. Physiol. 254:H459–H467). Electrical stimulation caused frequency-dependent relaxation. Addition of ABHA in the absence of electrical stimulation caused moderate relaxation due to basal activity of NO synthase, as shown in FIGS. 30A and 30B. ABHA significantly enhanced relaxation in response to electrical stimulation in a dose-dependent manner, as illustrated in FIG. 30C. This potentiation was more noticeable at lower frequencies (i.e. not greater than about 2 Hertz). These results indicate that arginase can modulate the production and availability of NO in penile corpus cavenosum.

Experiments described above using IAS muscle of opossum identify arginase as the specific receptor for ABHA. This enzyme is responsible for enhanced relaxation. Specifically, arginase causes attenuation of smooth muscle relaxation by NANC nerve stimulation, and such relaxation can be restored by addition of ABHA to tissue baths. In contrast, ABHA does not cause reversal of smooth muscle relaxation in the presence of an NO synthase inhibitor such as $N^\omega$-nitro-L-arginine. Taken together, these results indicate that arginase modulates production and availability of NO in gastrointestinal smooth muscle, and in penile corpus cavenosum.

Bioavailability of substrate L-arginine for NO biosynthesis can be a function of dietary intake. For instance, dietary supplementation with L-arginine in an animal model resulted in increased levels of NO synthase activity and enhanced erectile function without changing NO synthase expression, suggesting that L-arginine concentrations in the penis can be a substrate-limiting factor for NO synthase activity (see Moody et al., 1997, J. Urol. 158:942–947). Furthermore, long-term oral administration of L-arginine in patients with interstitial cystitis increased NO-related enzymes and metabolites (Wheeler et al., 1997, J. Urol. 158:2045–2050). Oral administration of 2,800 milligrams per day L-arginine improved erections in 40% of impotent but otherwise healthy patients in a pilot study (Zorgniotti et al., 1994, J. Impotence Res. 6:33–35).

Although the connection between L-arginine bioavailability and NO biosynthesis is complex, enhancement of NANC nerve-mediated smooth muscle tone effected by ABHA indicates that arginase has a role in modulating L-arginine bioavailability for NO biosynthesis in the penis. These experiments demonstrate that the activity of human penile arginase can be inhibited using ABHA or another arginase inhibitor described herein in order to alleviate or inhibit erectile dysfunction.

The disclosures of each and every patent, patent application, and publication cited herein are hereby incorporated herein by reference in their entirety.

While this invention has been disclosed with reference to specific embodiments, it is apparent that other embodiments and variations of this invention can be devised by others skilled in the art without departing from the true spirit and scope of the invention. The appended claims are intended to be construed to include all such embodiments and equivalent variations.

What is claimed is:

1. A method of inhibiting the activity of an arginase, the method comprising contacting the arginase with a compound having the structure

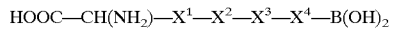

wherein each of $X^1$, $X^2$, $X^3$, and $X^4$ is selected from the group consisting of —(CH$_2$)—, —S—, —O—, —(NM)—, and —(N-alkyl)—.

2. The method of claim 1, wherein the arginase is yeast arginase.

3. The method of claim 1, wherein the compound hag a structure selected from the group consisting of

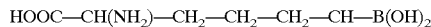

and

4. The method of claim 3, wherein the compound is 2(S)-amino-6-boronohexanoic acid.

5. The method of claim 1, wherein the arginase is a mammalian arginase.

6. The method of claim 5, wherein the arginase is a human arginase.

7. The method of claim 6, wherein the arginase is a human type II arginase.

8. A method of inhibiting the activity of an arginase in a mammal, the method comprising administering to the mammal a composition comprising a pharmaceutically acceptable carrier and an arginase inhibitor having the structure

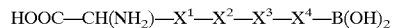

wherein each of $X^1$, $X^2$, $X^3$, and $X^4$ is selected from the group consisting of —(CH$_2$)—, —S—, —O—, —(NH)—, and —(N-alkyl)—.

9. The method of claim 8, wherein the compound has a structure selected from the group consisting of

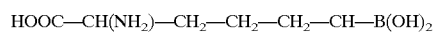

and

10. The method of claim 8, wherein the mammal is a human.

11. The method of claim 10, wherein the human comprises a tissue which exhibits an abnormally high level of arginase activity.

12. The method of claim 10, wherein the human comprises a tissue which exhibits an abnormally low level of nitric oxide synthase activity.

13. A method of treating a disorder associated with an abnormally low level of nitric oxide synthase activity in a tissue of a human, the method comprising administering to the human a composition comprising a pharmaceutically acceptable carrier and an arginase inhibitor having the structure

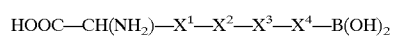

wherein each of $X^1$, $X^2$, $X^3$, and $X^4$ is selected from the group consisting of —(CH$_2$)—, —S—, —O—, —(NH)—, and —(N-alkyl)—.

14. The method of claim 13, wherein the inhibitor has a structure selected from the group consisting of

and

15. The method of claim 13, wherein the disorder is selected from the group consisting of heart disease, systemic hypertension, pulmonary hypertension, erectile dysfunction, autoimmune encephalomyelitis, chronic renal failure, a gastrointestinal motility disorder, a gastric cancer, reduced hepatic blood flow, and cerebral vasospasm.

16. A method of relaxing smooth muscle in a mammal, the method comprising administering to the mammal a composition comprising a pharmaceutically acceptable carrier and an arginase inhibitor having the structure

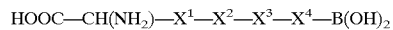

wherein each of $X^1$, $X^2$, $X^3$, and $X^4$ is selected from the group consisting of —(CH$_2$)—, —S—, —O—, —(NH)—, and —(N-alkyl)—.

17. The method of claim 16, wherein the inhibitor has a structure selected from the group consisting of

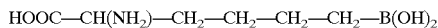

and

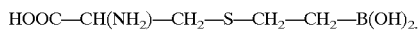

18. The method of claim 16, wherein the smooth muscle is selected from the group consisting of gastrointestinal smooth muscle, anal sphincter smooth muscle, esophageal sphincter muscle, corpus cavernosum, sphincter of Oddi, arterial smooth muscle, heart smooth muscle, pulmonary smooth muscle, kidney smooth muscle, uterine smooth muscle, vaginal smooth muscle, cervical smooth muscle, placental smooth muscle, and ocular smooth muscle.

19. A method of making a compound having the structure

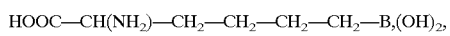

the method comprising contacting a molecule of the tert-butyl ester of 2(S)-N-(tert-butyloxycarbonyl)-6-[(1S,2S,3R,5S)-(+)-pinanedioxaboranyl]-hexanoic acid in an organic solvent with $BCl_3$.

20. The method of claim 19, wherein the organic solvent is $CH_2Cl_2$.

21. A method of making a compound having the structure

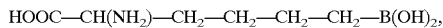

the method comprising the steps of
(a) mixing a solution of the tert-butyl ester of 2(S)-N-(tert-butyloxycarbonyl)-glutamic acid in tetrahydrofuran with triethylamine and ethyl chloroformate to produce a first mixture, removing the resulting triethylammonium hydrochloride salt by filtration, and treating the remaining mixture with an aqueous solution of sodium borohydride to provide a first compound, wherein the first compound is the tert-butyl ester of 2(S)-N-(tert-butyloxycarbonyl)-5-hydroxypentanoic acid;
(b) subjecting the first compound to Swern oxidation to produce a second compound;
(c) subjecting the second compound to a Wittig reaction in the presence of triphenylphosphonium methylide to produce a third compound;
(d) mixing a solution of $BH_3$ with the third compound in the presence of tetrahydrofuran to produce a second mixture;

(e) adding (1S,2S,3R,5S)-(+)-pinanediol to the second mixture to produce a fourth compound, wherein the fourth compound is the tert-butyl ester of 2(S)-N-(tert-butyloxycarbonyl)-6-[(1S,2S,3R,5S)-(+)-pinanedioxaboranyl]-hexanoic acid; and
(f) mixing the fourth compound with $BCl_3$ in the presence of $CH_2Cl_2$ to produce a compound having the structure

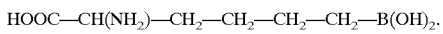

22. A method of alleviating erectile dysfunction in a human, the method comprising administering to the human a pharmaceutical composition comprising an arginase inhibitor having the structure

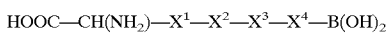

wherein each of $X^1$, $X^2$, $X^3$, and $X^4$ is selected from the group consisting of $-(CH_2)-$, $-S-$, $-O-$, $-(NH)-$, and $-(N\text{-alkyl})-$.

23. The method of claim 22, wherein the inhibitor is 2(S)-amino-6-boronohexanoic acid.

24. A method of treating a disorder associated with an abnormally high level of arginase activity in a tissue of a human, the method comprising administering to the human a composition comprising a pharmaceutically acceptable carrier and an arginase inhibitor having the structure

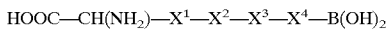

wherein each of $X^1$, $X^2$, $X^3$, and $X^4$ is selected from the group consisting of $-(CH_2)-$, $-S-$, $-O-$, $-(NH)-$, and $-(N\text{-alkyl})-$.

25. The method of claim 24, wherein the inhibitor has a structure selected from the group consisting of

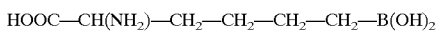

and

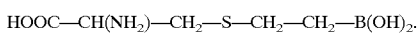

26. The method of claim 21, wherein the disorder is selected from the group consisting of heart disease, systemic hypertension, pulmonary hypertension, erectile dysfunction, autoimmune encephalomyelitis, chronic renal failure, a gastrointestinal motility disorder, a gastric cancer, reduced hepatic blood flow, and cerebral vasospasm.

* * * * *